(12) United States Patent
Kenedy et al.

(10) Patent No.: US 8,458,097 B2
(45) Date of Patent: *Jun. 4, 2013

(54) SYSTEM, METHOD AND SOFTWARE FOR HEALTHCARE SELECTION BASED ON PANGENETIC DATA

(75) Inventors: Andrew Alexander Kenedy, Sugar Land, TX (US); Charles Anthony Eldering, Furlong, PA (US)

(73) Assignee: Expanse Networks, Inc., Furlong, PA (US)

( * ) Notice: Subject to any disclaimer, the term of this patent is extended or adjusted under 35 U.S.C. 154(b) by 247 days.

This patent is subject to a terminal disclaimer.

(21) Appl. No.: 13/037,917

(22) Filed: Mar. 1, 2011

(65) Prior Publication Data

US 2011/0153356 A1  Jun. 23, 2011

Related U.S. Application Data

(63) Continuation of application No. 12/207,720, filed on Sep. 10, 2008, now Pat. No. 7,917,438.

(51) Int. Cl.
*G06F 21/00* (2006.01)
(52) U.S. Cl.
USPC .................. 705/51; 705/64; 705/67
(58) Field of Classification Search
USPC .............................. 705/51, 64, 67
See application file for complete search history.

(56) References Cited

U.S. PATENT DOCUMENTS

| | | | |
|---|---|---|---|
| 5,301,105 A | 4/1994 | Cummings, Jr. | |
| 5,446,886 A | 8/1995 | Li | |
| 5,551,880 A | 9/1996 | Bonnstetter et al. | |
| 5,649,181 A | 7/1997 | French et al. | |
| 5,660,176 A | 8/1997 | Iliff | |
| 5,715,451 A | 2/1998 | Marlin | |
| 5,724,567 A | 3/1998 | Rose et al. | |
| 5,752,242 A | 5/1998 | Havens | |
| 5,769,074 A | 6/1998 | Barnhill | |
| 5,860,917 A | 1/1999 | Comanor et al. | |
| 5,940,802 A | 8/1999 | Hidebrand | |
| 5,985,559 A | 11/1999 | Brown | |
| 6,063,028 A | 5/2000 | Luciano | |
| 6,108,647 A | 8/2000 | Poosala et al. | |
| 6,131,092 A | 10/2000 | Masand | |

(Continued)

FOREIGN PATENT DOCUMENTS

| | | |
|---|---|---|
| WO | WO01/27857 | 4/2001 |
| WO | WO02/10456 | 2/2002 |

(Continued)

OTHER PUBLICATIONS

Duell, E.J. et al. A population-based, case-control study of polymorphisms in carcinogen-metabolizing genes, smoking, and pancreatic adenocarcinoma risk. Journal of National Cancer Institute 94, 297-306 (2002).

(Continued)

*Primary Examiner* — Pierre E Elisca

(57) ABSTRACT

A system, method and software for healthcare selection are presented in which a user can authorize the comparison of their pangenetic (genetic and epigenetic) data with data profiles corresponding to health care products, services, and service providers to determine which are the most appropriate for a particular consumer. Data masks can be applied to limit the amount of pangenetic data transmitted for analysis.

14 Claims, 20 Drawing Sheets

U.S. PATENT DOCUMENTS

| | | |
|---|---|---|
| 6,203,993 B1 | 3/2001 | Shuber |
| 6,216,134 B1 | 4/2001 | Heckerman et al. |
| 6,253,203 B1 | 6/2001 | O'Flaherty et al. |
| 6,269,364 B1 | 7/2001 | Kennedy |
| 6,303,297 B1 | 10/2001 | Lincoln et al. |
| 6,317,700 B1 | 11/2001 | Bagne |
| 6,321,163 B1 | 11/2001 | Graham et al. |
| 6,363,399 B1 | 3/2002 | Maslyn et al. |
| 6,457,001 B1 | 9/2002 | Ishida |
| 6,493,637 B1 | 12/2002 | Steeg |
| 6,507,840 B1 | 1/2003 | Ioannidis et al. |
| 6,510,430 B1 | 1/2003 | Oberwager et al. |
| 6,519,604 B1 | 2/2003 | Acharya et al. |
| 6,596,488 B2 | 7/2003 | Pfeifer et al. |
| 6,601,059 B1 | 7/2003 | Fries |
| 6,629,097 B1 | 9/2003 | Keith |
| 6,629,935 B1 | 10/2003 | Miller et al. |
| 6,640,211 B1 | 10/2003 | Holden |
| 6,654,724 B1 | 11/2003 | Rubin |
| 6,687,696 B2 | 2/2004 | Hofmann et al. |
| 6,694,311 B1 | 2/2004 | Smith |
| 6,730,023 B1 | 5/2004 | Dodds |
| 6,738,762 B1 | 5/2004 | Chen et al. |
| 6,873,914 B2 | 3/2005 | Winfield |
| 6,912,492 B1 | 6/2005 | Johnson |
| 6,931,326 B1 | 8/2005 | Judson |
| 6,947,174 B1 | 9/2005 | Chen et al. |
| 6,988,075 B1 | 1/2006 | Hacker |
| 6,993,532 B1 | 1/2006 | Platt et al. |
| 7,054,758 B2 | 5/2006 | Gill-Garrison |
| 7,069,308 B2 | 6/2006 | Abrams |
| 7,107,155 B2 | 9/2006 | Frudakis |
| 7,127,355 B2 | 10/2006 | Cox |
| 7,162,471 B1 | 1/2007 | Knight |
| 7,260,480 B1 | 8/2007 | Brown et al. |
| 7,271,243 B2 | 9/2007 | Dumas Milne Edwards et al. |
| 7,305,348 B1 | 12/2007 | Brown |
| 7,406,484 B1 | 7/2008 | Srinivasan et al. |
| 7,426,472 B2 | 9/2008 | Fitzpatrick et al. |
| 7,572,603 B2 | 8/2009 | Small et al. |
| 7,592,910 B2 | 9/2009 | Tuck et al. |
| 7,668,738 B2 | 2/2010 | Wiggins |
| 7,720,855 B2 | 5/2010 | Brown |
| 7,739,247 B2 | 6/2010 | Mount et al. |
| 7,752,215 B2 | 7/2010 | Dettinger et al. |
| 7,769,740 B2 | 8/2010 | Martinez et al. |
| 7,809,716 B2 | 10/2010 | Wang et al. |
| 7,877,398 B2 | 1/2011 | Kroeschel et al. |
| 7,904,511 B2 | 3/2011 | Ryan et al. |
| 7,917,374 B2 | 3/2011 | Walker |
| 8,036,915 B2 | 10/2011 | Kremer et al. |
| 8,200,509 B2 | 6/2012 | Kenedy et al. |
| 8,239,455 B2 | 8/2012 | Wang |
| 2001/0000810 A1 | 5/2001 | Alabaster |
| 2001/0034023 A1 | 10/2001 | Stanton et al. |
| 2002/0010552 A1 | 1/2002 | Rienhoff |
| 2002/0048763 A1 | 4/2002 | Penn et al. |
| 2002/0052761 A1 | 5/2002 | Fey et al. |
| 2002/0059082 A1 | 5/2002 | Moczygemba |
| 2002/0064792 A1 | 5/2002 | Lincoln et al. |
| 2002/0080169 A1 | 6/2002 | Diederiks |
| 2002/0095585 A1 | 7/2002 | Scott |
| 2002/0107641 A1 | 8/2002 | Schaeffer et al. |
| 2002/0120623 A1 | 8/2002 | Vivier et al. |
| 2002/0126545 A1 | 9/2002 | Warren et al. |
| 2002/0128860 A1 | 9/2002 | Leveque |
| 2002/0133299 A1 | 9/2002 | Jacob |
| 2002/0137086 A1 | 9/2002 | Olek |
| 2002/0169793 A1 | 11/2002 | Sweeney |
| 2002/0179097 A1 | 12/2002 | Atkins |
| 2002/0183965 A1 | 12/2002 | Gogolak |
| 2003/0009295 A1 | 1/2003 | Markowitz et al. |
| 2003/0023387 A1 | 1/2003 | Gill-Garrison |
| 2003/0030637 A1 | 2/2003 | Grinstein et al. |
| 2003/0037041 A1 | 2/2003 | Hertz |
| 2003/0040002 A1 | 2/2003 | Ledley |
| 2003/0046114 A1 | 3/2003 | Davies |
| 2003/0065241 A1 | 4/2003 | Hohnloser |
| 2003/0065535 A1 | 4/2003 | Karlov |
| 2003/0069199 A1 | 4/2003 | Polansky |
| 2003/0099958 A1 | 5/2003 | McCarthy |
| 2003/0115193 A1 | 6/2003 | Okamoto et al. |
| 2003/0130873 A1 | 7/2003 | Nevin |
| 2003/0135391 A1 | 7/2003 | Edmundson et al. |
| 2003/0135488 A1 | 7/2003 | Amir et al. |
| 2003/0154104 A1 | 8/2003 | Koningsberg |
| 2003/0163340 A1 | 8/2003 | Fitzpatrick et al. |
| 2003/0167260 A1 | 9/2003 | Nakamura et al. |
| 2003/0171876 A1 | 9/2003 | Markowitz et al. |
| 2003/0195706 A1 | 10/2003 | Korenberg |
| 2003/0198970 A1 | 10/2003 | Roberts |
| 2003/0203008 A1 | 10/2003 | Gunasekaran |
| 2003/0212579 A1 | 11/2003 | Brown et al. |
| 2004/0006488 A1 | 1/2004 | Fitall et al. |
| 2004/0009495 A1 | 1/2004 | O'Malley et al. |
| 2004/0014097 A1 | 1/2004 | McGlennen et al. |
| 2004/0015337 A1 | 1/2004 | Thomas |
| 2004/0019688 A1 | 1/2004 | Nickerson et al. |
| 2004/0030697 A1 | 2/2004 | Cochran et al. |
| 2004/0034652 A1 | 2/2004 | Hofmann et al. |
| 2004/0078216 A1 | 4/2004 | Toto |
| 2004/0083123 A1 | 4/2004 | Kim et al. |
| 2004/0093331 A1 | 5/2004 | Garner |
| 2004/0111410 A1 | 6/2004 | Burgoon et al. |
| 2004/0158581 A1 | 8/2004 | Kotlyar |
| 2004/0172287 A1 | 9/2004 | O'Toole et al. |
| 2004/0172313 A1 | 9/2004 | Stein et al. |
| 2004/0177071 A1 | 9/2004 | Massey et al. |
| 2004/0193019 A1 | 9/2004 | Wei |
| 2004/0197799 A1 | 10/2004 | Williamson |
| 2004/0219493 A1 | 11/2004 | Phillips |
| 2004/0221855 A1 | 11/2004 | Ashton |
| 2004/0230440 A1 | 11/2004 | Malhotra |
| 2004/0242454 A1 | 12/2004 | Gallant |
| 2004/0243545 A1 | 12/2004 | Boone et al. |
| 2004/0254920 A1 | 12/2004 | Brill et al. |
| 2005/0021240 A1 | 1/2005 | Berlin |
| 2005/0026119 A1 | 2/2005 | Ellis et al. |
| 2005/0032066 A1 | 2/2005 | Heng |
| 2005/0037405 A1 | 2/2005 | Caspi |
| 2005/0060194 A1 | 3/2005 | Brown |
| 2005/0086260 A1 | 4/2005 | Canright et al. |
| 2005/0090718 A1 | 4/2005 | Dodds |
| 2005/0108067 A1 | 5/2005 | Chapman |
| 2005/0120019 A1 | 6/2005 | Rigoutsos et al. |
| 2005/0143928 A1 | 6/2005 | Moser |
| 2005/0154627 A1 | 7/2005 | Zuzek et al. |
| 2005/0160458 A1 | 7/2005 | Baumgartner |
| 2005/0170321 A1 | 8/2005 | Scully |
| 2005/0176057 A1 | 8/2005 | Bremer |
| 2005/0191678 A1 | 9/2005 | Lapointe |
| 2005/0203900 A1 | 9/2005 | Nakamura et al. |
| 2005/0208454 A1 | 9/2005 | Hall |
| 2005/0256649 A1 | 11/2005 | Roses |
| 2005/0256848 A1 | 11/2005 | Alpert et al. |
| 2005/0260610 A1 | 11/2005 | Kurtz |
| 2005/0278125 A1 | 12/2005 | Harwood et al. |
| 2006/0015369 A1 | 1/2006 | Bachus |
| 2006/0052945 A1 | 3/2006 | Rabinowitz |
| 2006/0059159 A1 | 3/2006 | Truong et al. |
| 2006/0064415 A1 | 3/2006 | Guyon et al. |
| 2006/0099597 A1 | 5/2006 | Kaneda et al. |
| 2006/0129034 A1 | 6/2006 | Kasabov |
| 2006/0184521 A1 | 8/2006 | Ponte |
| 2006/0184557 A1 | 8/2006 | Pollack et al. |
| 2006/0195335 A1 | 8/2006 | Christian et al. |
| 2006/0195442 A1 | 8/2006 | Cone et al. |
| 2006/0206483 A1 | 9/2006 | Knepper et al. |
| 2006/0206569 A1 | 9/2006 | Heidloff et al. |
| 2006/0218111 A1 | 9/2006 | Cohen |
| 2006/0235881 A1 | 10/2006 | Masarie et al. |
| 2006/0240862 A1 | 10/2006 | Neven et al. |
| 2006/0253427 A1 | 11/2006 | Wu et al. |
| 2006/0293921 A1 | 12/2006 | McCarthy et al. |
| 2007/0016568 A1 | 1/2007 | Amir et al. |
| 2007/0027636 A1 | 2/2007 | Rabinowitz |
| 2007/0027720 A1 | 2/2007 | Hasan et al. |

| | | | |
|---|---|---|---|
| 2007/0027850 | A1 | 2/2007 | Chan et al. |
| 2007/0050354 | A1 | 3/2007 | Rosenberg |
| 2007/0061085 | A1 | 3/2007 | Fernandez |
| 2007/0061166 | A1 | 3/2007 | Ramasubramanian et al. |
| 2007/0067297 | A1 | 3/2007 | Kublickis |
| 2007/0106536 | A1* | 5/2007 | Moore .............................. 705/3 |
| 2007/0106754 | A1* | 5/2007 | Moore .............................. 709/217 |
| 2007/0116036 | A1* | 5/2007 | Moore .............................. 370/462 |
| 2007/0122824 | A1 | 5/2007 | Tucker |
| 2007/0220017 | A1 | 9/2007 | Zuzarte et al. |
| 2007/0260128 | A1 | 11/2007 | Hogan et al. |
| 2007/0294109 | A1 | 12/2007 | Costello |
| 2008/0004848 | A1 | 1/2008 | Avey |
| 2008/0004912 | A1 | 1/2008 | Niwa |
| 2008/0040151 | A1* | 2/2008 | Moore .............................. 705/2 |
| 2008/0059431 | A1 | 3/2008 | Aoki et al. |
| 2008/0108881 | A1 | 5/2008 | Stupp et al. |
| 2008/0162555 | A1 | 7/2008 | Schuler et al. |
| 2008/0195594 | A1 | 8/2008 | Gerjets et al. |
| 2008/0199853 | A1 | 8/2008 | Wohlgemuth et al. |
| 2008/0201327 | A1 | 8/2008 | Seth |
| 2008/0208840 | A1 | 8/2008 | Zhang et al. |
| 2008/0228706 | A1 | 9/2008 | Kenedy et al. |
| 2008/0228797 | A1 | 9/2008 | Kenedy et al. |
| 2008/0235046 | A1 | 9/2008 | Fitzpatrick et al. |
| 2008/0256023 | A1 | 10/2008 | Nair |
| 2008/0256052 | A1 | 10/2008 | Kar et al. |
| 2008/0294607 | A1 | 11/2008 | Partovi et al. |
| 2008/0301128 | A1 | 12/2008 | Gandert et al. |
| 2008/0306919 | A1 | 12/2008 | Iwayama et al. |
| 2008/0320021 | A1 | 12/2008 | Chan et al. |
| 2009/0048997 | A1 | 2/2009 | Aoki et al. |
| 2009/0083654 | A1 | 3/2009 | Nickerson et al. |
| 2009/0094261 | A1 | 4/2009 | Jung et al. |
| 2009/0209270 | A1 | 8/2009 | Gutierrez et al. |
| 2009/0234878 | A1 | 9/2009 | Herz et al. |
| 2009/0271375 | A1 | 10/2009 | Hyde et al. |
| 2010/0027780 | A1 | 2/2010 | Jung et al. |
| 2010/0041958 | A1 | 2/2010 | Leuthardt et al. |
| 2010/0063930 | A1 | 3/2010 | Kenedy et al. |
| 2010/0287213 | A1 | 11/2010 | Rolls et al. |
| 2011/0137944 | A1 | 6/2011 | Rolls |

FOREIGN PATENT DOCUMENTS

| | | |
|---|---|---|
| WO | WO02/080079 | 10/2002 |
| WO | WO2004/031912 | 4/2004 |
| WO | WO2004/051548 | 6/2004 |
| WO | WO2004/075010 | 9/2004 |
| WO | WO2004/097577 | 11/2004 |
| WO | WO2005/086891 | 9/2005 |
| WO | WO2006/052952 | 5/2006 |
| WO | WO2006/084195 | 8/2006 |
| WO | WO2007/061881 | 5/2007 |

OTHER PUBLICATIONS

"Unimobile Launches Advanced Wireless Data Platform and Services to Extend the Reach of Enterprise Applications—PRNewswire, Feb. 13, 2001".
"Syed Sibte Raza Abidi; Leveraing XML-Based electronic medical records to extract experiental clinical knowledge. Anautomated approach to generate cases for medical case-based reasoning systems; Syed Sibte Raza Abidi; 2002; InformationJournal of Medical Information; 68; pp. 187-203".
Prakash M. Nadkarni, et al. "Data Extraction and Ad Hoc Query of an Entity-Attribute-Value Database", Journal of the American Medical Informatics Association, vol. 5, No. 6, Nov./Dec. 1998, pp. 511-527.
Mani et al., Causal Discover From Medical Textual Data, Fall 2000, Hanley and Belfus Publishers, pp. 542-546.
Roddick et al., Exploratory Medical Knowledge Discover: Experiences and Issues, Jul. 2003, ACM, vol. 5, Issue 1, pp. 94-99.
Prather et al., Medical data mining: knowledge discovery in a clinical data warehouse, Fall 1997, Proceedings of the AMIA Annual Fall Symposium, pp. 101-105.
Cespivova et al., Roles of Medical Ontology in Association Mining CRISP-DM Cycle, Proceedings of the ECML/PKDD04 Workshop on Knowledge Discovery and Ontologies, PISA 2004, 12 pages.
Abe et al., Implementing an Integrated Time-Series Data Mining Environment Based on Temporal Pattern Extraction Methods: A Case Study of an Interferon Therapy Risk Mining for Chronic Hepatitis, 2006, New Frontiers in Artificial Intelligence, Lecture Notes in Computer Science, vol. 4012/2006, pp. 425-435.
Hitsch et al., "What Makes You Click?—Mate Preference and Matching Outcomes in Online Dating", MIT Sloan Research Paper No. 4603-06, Apr. 2006. 62 pages.
Vrbsky, S.V. & Liu, J.W.S. "Approximate—A Query Processor That Produces Monotonically Improving Approximate Answers." IEEE Transactions on Knowledge and Data Engineering 5, 1056-1068 (1993).
Anonymous, "Frequency" (Web Definition), Feb. 24, 2011, Wikipedia, p. 1.
Miyamoto et al., "Diagnostic and Therapeutic Applications of Epigenetics", Japanese Journal of Clinical Oncology, Jun. 1, 2005, pp. 293-301, 35 (6), Keigakul Publishing Company, Japan.
Peedicayil, "Epigenetic Therapy—a New Development in Pharmacology", Indian Journal of Medical Research, Jan. 2006, pp. 17-24, 123 (I), Council of Medical Research, India.
Glaser et al., "Advancing Personalized Health Care through Health Information Technology: An Update from the American Health Information Community's Persoanlized Health Care Workgroup", Journal of the Maerican Medical Informatics Association, Jul. 2008, pp. 391-396, 15 (4), American Medical Informatics Association, USA.
Jiawei Han; Discovery of Multiple-Level Association Rules from Large Database' 1995; pp. 1-12.
Serafim Batzoglou, Lior Pachter, Jill P. Mesirov, et al. "Human and Mouse Gene Structure: Comparative Analysis and Application to Exon Prediction." Genome Research. 2000 10: 950-958. Copyright 2000, Cold Spring Harbor Laboratory Press.
Klein, T. E. et al. Integrating genotype and phenotype information: an overview of the PharmGKB project. The Pharmacogenomics Journal 1, 167-1 70 (2001).
Das, S. Filters, wrappers and a boosting-based hybrid for feature selection. In Proceedings of the Eighteenth International Conference on Machine Learning, 74-81 (Morgan Kaufmann Publishers Inc., San Francisco, CA, USA, 2001).
Duan, K.-B. B., Rajapakse, J. C., Wang, H. & Azuaje, F. Multiple svm-rfe for gene selection in cancer classification with expression data. IEEE transactions on nanobioscience 4, 228-234 (2005).
Nielsen, T. et al. Molecular characterisation of soft tissue tumours: a gene expression study. The Lancet 359, 1301-1307 (2002).
Cooper, D. N. & Krawczak, M. The mutational spectrum of single base-pair substitutions causing human genetic disease: patterns and predictions. Human Genetics 85, 55-74 (1990).
Wagner, SF. Introduction to Statistics. Harper Collins Publishers (1992). pp. 23-30.

* cited by examiner

| Consumer Disorder | Consumer Pangenetic Combination | Service (provide treatment) | % Success | Success Level |
|---|---|---|---|---|
| Hypertension | Rs4961 = (T;T) Rs5186 = (C;C) Rs3865418 = (T;C) | Exercise therapy | 47 | 5 |
| Hypertension | Rs6997709 = (G;G) Rs11110912 = (G;C) Rs1937506 = (G;G) | Exercise therapy | 35 | 4 |
| Hypertension | Rs3755351 = (C;A) Rs3794260 = (G;G) Rs1805762 = (G;G) | Exercise therapy | 88 | 9 |
| Hypertension | Rs4961 = (T;T) Rs5186 = (C;C) Rs3865418 = (T;C) | Dietary counseling | 16 | 2 |
| Hypertension | Rs6997709 = (G;G) Rs11110912 = (G;C) Rs1937506 = (G;G) | Dietary counseling | 91 | 9 |
| Hypertension | Rs3755351 = (C;A) Rs3794260 = (G;G) Rs1805762 = (G;G) | Dietary counseling | 54 | 5 |
| Hypertension | Rs4961 = (T;T) Rs5186 = (C;C) Rs3865418 = (T;C) | Drug E | 96 | 10 |
| Hypertension | Rs6997709 = (G;G) Rs11110912 = (G;C) Rs1937506 = (G;G) | Drug E | 63 | 6 |
| Hypertension | Rs3755351 = (C;A) Rs3794260 = (G;G) Rs1805762 = (G;G) | Drug E | 23 | 2 |

| Consumer Disorder | Consumer Pangenetic Combination | Service (provide treatment) | % Success | Success Level | Rank |
|---|---|---|---|---|---|
| Hypertension | Rs4961 = (T;T)<br>Rs5186 = (C;C)<br>Rs3865418 = (T;C) | Drug E | 96 | 10 | 1 |
| Hypertension | Rs4961 = (T;T)<br>Rs5186 = (C;C)<br>Rs3865418 = (T;C) | Exercise therapy | 47 | 5 | 2 |
| Hypertension | Rs4961 = (T;T)<br>Rs5186 = (C;C)<br>Rs3865418 = (T;C) | Dietary counseling | 16 | 2 | 3 |

B.

| Consumer Disorder | Consumer Pangenetic Combination | Service (provide treatment) | % Success | Success Level | Rank |
|---|---|---|---|---|---|
| Hypertension | Rs6997709 = (G;G)<br>Rs11110912 = (G;C)<br>Rs1937506 = (G;G) | Dietary counseling | 91 | 9 | 1 |
| Hypertension | Rs6997709 = (G;G)<br>Rs11110912 = (G;C)<br>Rs1937506 = (G;G) | Drug E | 63 | 6 | 2 |
| Hypertension | Rs6997709 = (G;G)<br>Rs11110912 = (G;C)<br>Rs1937506 = (G;G) | Exercise therapy | 35 | 4 | 3 |

C.

| Consumer Disorder | Consumer Pangenetic Combination | Service (provide treatment) | % Success | Success Level | Rank |
|---|---|---|---|---|---|
| Hypertension | Rs3755351 = (C;A)<br>Rs3794260 = (G;G)<br>Rs1805762 = (G;G) | Exercise therapy | 88 | 9 | 1 |
| Hypertension | Rs3755351 = (C;A)<br>Rs3794260 = (G;G)<br>Rs1805762 = (G;G) | Dietary counseling | 54 | 5 | 2 |
| Hypertension | Rs3755351 = (C;A)<br>Rs3794260 = (G;G)<br>Rs1805762 = (G;G) | Drug E | 23 | 2 | 3 |

*Fig. 3*

| Provider ID | ZIP Code | Patient Disorder | Patient SNP Combination | Prescribed Treatment | % Success | % Satisfied | Score |
|---|---|---|---|---|---|---|---|
| Shirley Able, M.D. | 19131 | Diabetes II | Rs6679677 = (A;A)<br>Rs9272346 = (A;G)<br>Rs11171739 = (C;C) | Drug A | 84 | 59 | 72 |
| Shirley Able, M.D. | 19131 | Diabetes II | Rs17696736 = (G;A)<br>Rs12708716 = (A;A)<br>Rs2639703 = (C;C) | Drug A | 6 | 4 | 5 |
| Shirley Able, M.D. | 19131 | Diabetes II | Rs17388568 = (A;A)<br>Rs2544677 = (G;G)<br>Rs2104286 = (A;G) | Drug A | 91 | 64 | 78 |
| Farley Mediocre, M.D. | 19203 | Diabetes II | Rs6679677 = (A;A)<br>Rs9272346 = (A;G)<br>Rs11171739 = (C;C) | Drug D | 58 | 41 | 50 |
| Farley Mediocre, M.D. | 19203 | Diabetes II | Rs17696736 = (G;A)<br>Rs12708716 = (A;A)<br>Rs2639703 = (C;C) | Drug D | 46 | 32 | 39 |
| Farley Mediocre, M.D. | 19203 | Diabetes II | Rs17388568 = (A;A)<br>Rs2544677 = (G;G)<br>Rs2104286 = (A;G) | Drug D | 90 | 63 | 77 |
| Shirley Able, M.D. | 19131 | Hypertension | Rs4961 = (T;T)<br>Rs5186 = (C;C)<br>Rs3865418 = (T;C) | Drug H and Exercise therapy | 62 | 43 | 53 |
| Shirley Able, M.D. | 19131 | Hypertension | Rs6997709 = (G;G)<br>Rs11110912 = (G;C)<br>Rs1937506 = (G;G) | Drug H and Exercise therapy | 73 | 51 | 62 |
| Shirley Able, M.D. | 19131 | Hypertension | Rs3755351 = (C;A)<br>Rs3794260 = (G;G)<br>Rs1805762 = (G;G) | Drug H and Exercise therapy | 56 | 39 | 48 |
| Farley Mediocre, M.D. | 19203 | Hypertension | Rs4961 = (T;T)<br>Rs5186 = (C;C)<br>Rs3865418 = (T;C) | Drug R and Dietary counseling | 63 | 44 | 54 |
| Farley Mediocre, M.D. | 19203 | Hypertension | Rs6997709 = (G;G)<br>Rs11110912 = (G;C)<br>Rs1937506 = (G;G) | Drug R and Dietary counseling | 82 | 57 | 70 |
| Farley Mediocre, M.D. | 19203 | Hypertension | Rs3755351 = (C;A)<br>Rs3794260 = (G;G)<br>Rs1805762 = (G;G) | Drug R and Dietary counseling | 27 | 19 | 23 |

*Fig. 4*

| Establishment ID | ZIP Code | Patient Disorder | Patient SNP Combination | Prescribed Treatment | % Success | % Satisfied | Score |
|---|---|---|---|---|---|---|---|
| Maxcare Clinic | 19131 | Diabetes II | Rs6679677= (A;A)<br>Rs9272346 = (A;G)<br>Rs11171739 = (C;C) | Drug A | 84 | 59 | 72 |
| Maxcare Clinic | 19131 | Diabetes II | Rs17696736 = (G;A)<br>Rs12708716 = (A;A)<br>Rs2639703 = (C;C) | Drug A | 6 | 4 | 5 |
| Maxcare Clinic | 19131 | Diabetes II | Rs17388568 = (A;A)<br>Rs2544677 = (G;G)<br>Rs2104286 = (A;G) | Drug A | 91 | 64 | 78 |
| Wellness Clinic | 19203 | Diabetes II | Rs6679677= (A;A)<br>Rs9272346 = (A;G)<br>Rs11171739 = (C;C) | Drug D | 58 | 41 | 50 |
| Wellness Clinic | 19203 | Diabetes II | Rs17696736 = (G;A)<br>Rs12708716 = (A;A)<br>Rs2639703 = (C;C) | Drug D | 46 | 32 | 39 |
| Wellness Clinic | 19203 | Diabetes II | Rs17388568 = (A;A)<br>Rs2544677 = (G;G)<br>Rs2104286 = (A;G) | Drug D | 90 | 63 | 77 |
| Maxcare Clinic | 19131 | Hypertension | Rs4961 = (T;T)<br>Rs5186 = (C;C)<br>Rs3865418 = (T;C) | Drug H and Exercise therapy | 62 | 43 | 53 |
| Maxcare Clinic | 19131 | Hypertension | Rs6997709 = (G;G)<br>Rs11110912 = (G;C)<br>Rs1937506 = (G;G) | Drug H and Exercise therapy | 73 | 51 | 62 |
| Maxcare Clinic | 19131 | Hypertension | Rs3755351 = (C;A)<br>Rs3794260 = (G;G)<br>Rs1805762 = (G;G) | Drug H and Exercise therapy | 56 | 39 | 48 |
| Wellness Clinic | 19203 | Hypertension | Rs4961 = (T;T)<br>Rs5186 = (C;C)<br>Rs3865418 = (T;C) | Drug R and Dietary counseling | 63 | 44 | 54 |
| Wellness Clinic | 19203 | Hypertension | Rs6997709 = (G;G)<br>Rs11110912 = (G;C)<br>Rs1937506 = (G;G) | Drug R and Dietary counseling | 82 | 57 | 70 |
| Wellness Clinic | 19203 | Hypertension | Rs3755351 = (C;A)<br>Rs3794260 = (G;G)<br>Rs1805762 = (G;G) | Drug R and Dietary counseling | 27 | 19 | 23 |

*Fig. 5*

Data Mask # 1:  U U U M M M U U U M M M M M U U U U U U U M M U M M U U U M M M M U M U U Data Mask # 2:  U U U U U U U M M M M M U U M M U U U M M M M M U U U U U U U U U U Data Mask # 3:  U U U M M M U U U M M U M M U U U U U U M U M M U M M U U U M M M M U U U Consensus :  U U U M M M U U M M M M M U U M M U U M U M M M M M U U U M M M M U M U U

*Fig. 14*

SYSTEM, METHOD AND SOFTWARE FOR HEALTHCARE SELECTION BASED ON PANGENETIC DATA

This application in a continuation of U.S. patent application Ser. No. 12/207,720, filed Sep. 10, 2008, entitled System for Secure Mobile Healthcare Selection, the disclosure of which is incorporated herein by reference in its entirety.

BRIEF DESCRIPTION OF THE DRAWINGS

The following detailed description will be better understood when read in conjunction with the appended drawings, in which there is shown one or more of the multiple embodiments of the present invention. It should be understood, however, that the various embodiments are not limited to the precise arrangements and instrumentalities shown in the drawings.

FIG. 2 illustrates pangenetic profiles for pangenetic based selection of healthcare services;

FIG. 3 illustrates pangenetic based rank-ordered tabulations of services;

FIG. 4 illustrates pangenetic profiles for pangenetic based selection of healthcare providers;

FIG. 5 illustrates pangenetic profiles for pangenetic based selection of healthcare establishments;

FIG. 14 illustrates abstract representations of data masks;

DETAILED DESCRIPTION

Figure 1:
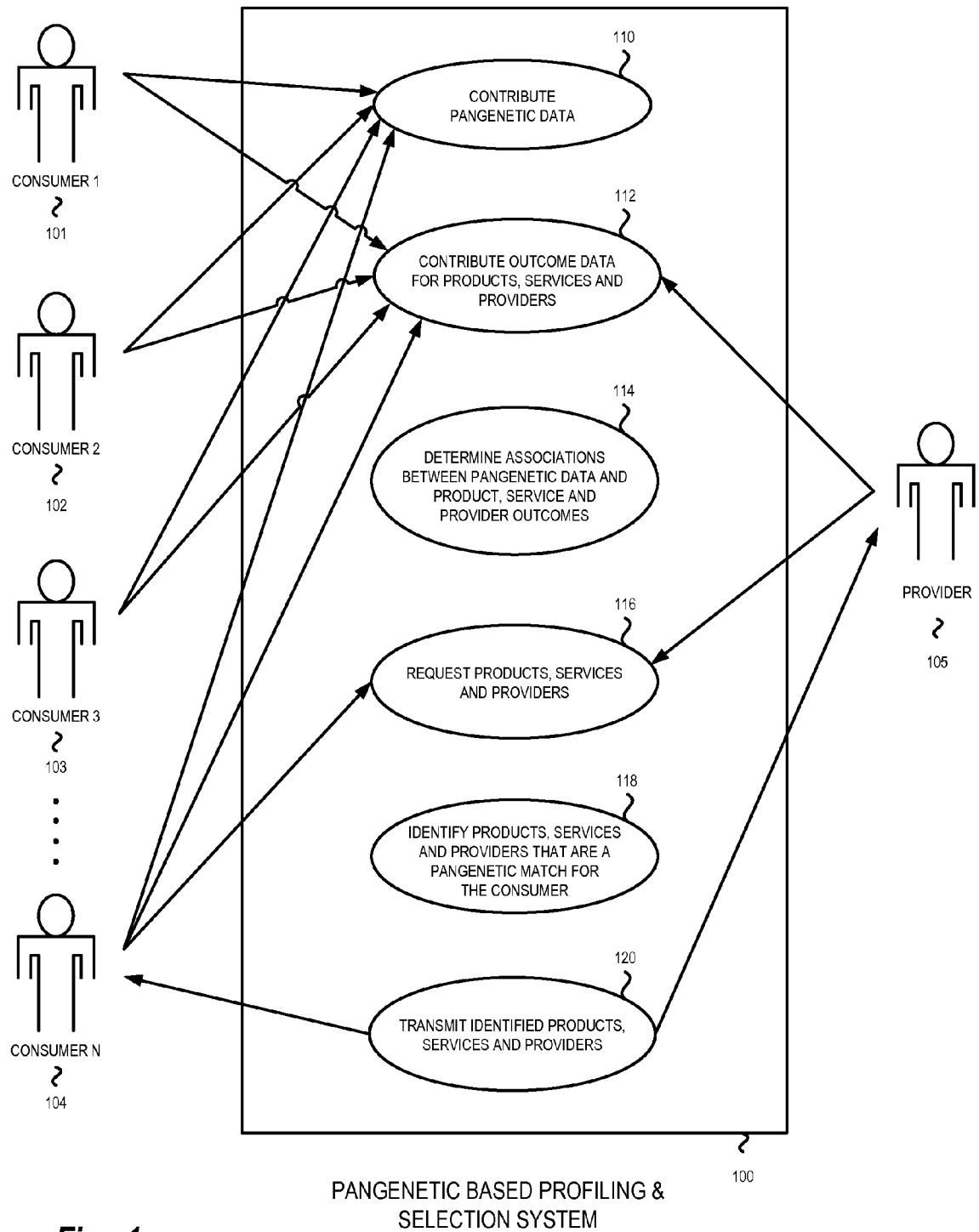
FIG. 1 illustrates a pangenetic based profiling & selection system.

With the recent introduction and successes of single nucleotide polymorphism (SNP) sequencing, full genomic sequencing and epigenetic sequencing in humans, wide ranging applications that utilize individuals' pangenetic (genetic and epigenetic) information become possible. Herein we disclose methods, systems, software and databases for personalized pangenetic based selection of products, services, service providers and establishments to facilitate efficient selection and recommendation of the most appropriate products and services for individual consumers and to improve the efficiency and quality of delivery of those products and services to consumers by providers and provider establishments. The disclosed inventions can also be used by industries such as the insurance industry to facilitate the selection and approval of covered products and services for plan members, and to facilitate the processing of financial transactions such as insurance claims.

In one embodiment, pangenetic based selection of products, services, service providers and establishments for an individual (e.g., a consumer) is accomplished in part by determining and utilizing associations between combinations of pangenetic features—also referred to in this disclosure as pangenetic data—and particular historical outcomes (i.e., successful outcome or customer satisfaction) experienced with specific products, services, service providers and establishments. These associations can be predetermined and stored in a database, or they can be determined in real time upon receiving a query (i.e., a request for information).

One aspect of the present invention is designed to determine and utilize associations between pangenetic features (genetic and epigenetic attributes) and non-pangenetic features of consumers and the outcomes they experience with particular products, services, service providers and establishments to improve selection of these entities for future consumers. Within the healthcare field for example, we expect it will be of tremendous benefit, as pangenetic data becomes more widely available and utilized in the near future, for patients to allow access and evaluation of their pangenetic data as part of treatment and provider selection. Applying the disclosed invention for this purpose has the potential to vastly improve the efficacy and efficiency achieved by the healthcare industry.

With respect to the healthcare industry it is known that medical providers such as physicians and hospitals, in part because of their relationships with pharmaceutical and medical device companies and their sales representatives, favor the prescription of a certain subset of drugs and medical devices for a targeted set of health conditions. For example, one group of physicians and hospitals may favor therapy regimen A which uses medication B and device C to treat a specific health condition, whereas a different group of physicians and hospitals may favor administration of therapy regimen X which uses medication Y and device Z to treat the same health condition. Because certain medications and therapies may have different success rates for individuals with different pangenetic makeups, this can lead to more successful treatment of a particular subgroup of patients by a particular subgroup of physicians and hospitals that administer medications and therapies which favor the particular pangenetic makeup of that subgroup of patients. For example, a first pangenetic subgroup of individuals may achieve more successful results with the therapy regimen A above, while a second pangenetic subgroup of individuals may achieve more successful treatment outcome by physicians and hospitals administering therapy regimen X above. By using pangenetic data to select products, services, providers and establishments that will achieve the best results for specific individuals, better treatment success rates can be readily achieved in the healthcare industry. This approach is equally applicable to other industries in which the compatibility of consumers with the products, services, service providers and establishments is strongly influenced by consumers' individual pangenetic characteristics.

Both the consumer (e.g., patient), the healthcare professional (e.g., clinician), and the healthcare insurer desire consistent excellent outcomes and high satisfaction levels with healthcare products and services that are delivered. By evaluating consumers' pangenetic features in the selection of products, services, service providers and establishments, consistently better outcomes and higher levels of satisfaction can be achieved, thereby reducing waste and increasing efficiency in the healthcare industry as well as potentially minimizing adverse reactions, complications and deaths. To accomplish this, pangenetic data shared in common between individuals that experience a good treatment outcome using a particular healthcare product, service, service provider, or establishment can be stored in association with an identifier (i.e., ID) representing that particular product, service, service provider, or establishment in a database. The relationships between particular combinations (i.e., patterns) of pangenetic data and particular outcomes can be identified and determined through the use of statistical methods to determine statistical correlations between those data, which can be recorded in datasets and databases as stored associations (correlations) between data representing those entities, for example. Later, these stored associations can be accessed by the consumer or healthcare professional using methods and systems disclosed herein which enable the user to query the database and conduct an automated comparison of the consumer's pangenetic makeup with pangenetic data contained in the database in order to select the medical product, service, service provider and/or establishment that is optimal for that consumer. Pangenetic based associations can be used simultaneously and in conjunction with (e.g., in combinatorial association with) non-pangenetic features of the customer such as age, gender, ethnicity, diet, lifestyle, and zip code (i.e., location), as well as non-pangenetic features of products and services such as recommended age for usage and adverse interactions with other products and services, and non-pangenetic features of service providers and establishments such as relative pricing and location, for example, to further refine potential selections.

Pangenetic data for an individual can be generated through SNP sequencing and/or genomic sequencing of an individual's cellular and mitochondrial DNA by a genetic sequencing facility. SNP sequencing provides a partial glimpse of an individual's pangenetic makeup by determining the identity of nucleotides at common polymorphic sites scattered throughout the genome. These polymorphic sites can be associated with disease and health related phenotypes, as well as other phenotypes (i.e., physical and behavioral outcomes and features) of interest.

Pangenetic data can also be generated for an individual using genomic sequencing which provides contiguous stretches of genomic nucleotide sequence that may encompass portions of genes, entire genes, or the entire genome comprising 46 chromosomes and approximately 6 billion nucleotide base pairs (approximately 3 billion from maternal contribution and 3 billion from paternal contribution). The greater resolution and coverage of the genome provided by genomic sequencing can potentially provide stronger and more statistically significant correlations with specific products, services, service providers and establishments. Further, SNP sequence data can be easily obtained from contiguous genomic sequence data, while the reverse is not possible since SNPs typically represent non-contiguous nucleotide locations in the genome. Therefore, methods that are designed to use the SNP information can be designed to extract SNP information from genomic sequence data as well. Pangenetic data representing epigenetic modifications of genomic DNA in the form of methylated cytosine nucleotides can be determined through similar methods employed in SNP and genomic sequencing after chemically treating the DNA with bisulfite for example, as is known to those skilled in the art.

There are several ways to represent pangenetic data in the present invention. For example, SNPs can be represented in datasets of the present invention by their unique numerical identifiers (for example, those listed in the NCBI's reference SNP database) and the identity of the nucleotide(s) present at each SNP position, potentially for both the maternal and paternal alleles. For example, homozygous A/A at SNP Rs6679677 indicates an individual possesses adenosine (A) nucleotides at the SNP Rs6679677 location on both the maternal and paternal alleles. Genomic sequence information on the other hand, can be represented by a combination of nucleotide position within the genome (usually with respect to a specific chromosome) and nucleotide identity (i.e., A, T, C, G). Epigenomic modification involving methylated cytosine residues in genomic DNA can be represented by a combination of nucleotide position and methylation status, where methylation status can be represented as a binary value (e.g., methylated (1) and unmethylated (0)). A descriptor which distinguishes whether a particular genetic or epigenetic feature lies on the maternal or paternal chromosome can also be included.

A significant advantage of incorporating pangenetic data into the selection of products, services, service providers and establishments is that pangenetic data are not susceptible to a variety of bias errors including misclassification bias, interview bias, surveillance bias, recall bias and reporting bias, which routinely affect other data collected and reported with respect to consumers. Further, quality control methods and multi-pass approaches used in modern genetic sequencing can ensure that measurement errors associated with the sequencing technology are nearly eliminated.

In one embodiment, an individual (i.e., consumer or patient) submits a bodily tissue or fluid sample to a genetic sequencing facility for SNP sequencing, or full or partial genomic and epigenomic sequencing. The genetic facility performs sequencing of DNA present in the sample and stores the resulting pangenetic data of the individual as an Electronic Medical Record (EMR) or equivalent. An EMR containing primarily pangenetic data associated with the individual can be termed a pangenetic EMR. Similar to the existing characteristics of EMRs, the pangenetic EMR would be an authenticated record produced by a licensed or certified health care facility or service provider, for example a genetic sequencing facility. The individual can request download of the pangenetic EMR from the genetic sequencing facility to their Electronic Health Record (EHR), which is a essentially a compilation of EMRs generated by medical providers (e.g., physicians, therapists) and medical establishments (e.g., hospitals, clinics, laboratories, pharmacies) that the individual received medical products or services from over time. The individual controls access to the data contained in their EHR, and as such, the individual can initiate and record authorizations in the EHR system for each medical provider or medical establishment that the individual would like to have access pangenetic data in their EHR. In another embodiment the EHR may alternatively exist in the form of a Personal Health Record (PHR), which is an Electronic Health Record which includes data from EMRs as well as data entered by the individual themself. Similarly to an EHR, the individual must provide authorization in order for others to be able to access the pangenetic and other data contained in their PHR.

Within this disclosure, the term 'medical' can be interpreted to encompass the term 'surgical'. The term 'healthcare', when used in reference to products, services, service providers and establishments, can be interpreted to encompass those products, services, service providers and establishments used within the medical industry as well as those used outside the medical industry for health related purposes. When used with respect to the healthcare industry, the term 'establishments' can refer to clinics, hospitals, inpatient centers, outpatient centers, transient care facilities, rehabilitation centers, therapeutic centers, nursing homes, convalescent homes, palliative care centers, hospices, pharmacies, healthcare product vendors, medical teaching facilities, biomedical research facilities, clinical research centers, biotechnology companies and pharmaceutical companies, for example. While the products, services, service providers and establishments of the present disclosure may be related to medical care or healthcare, if not so specified, they can also be related to other markets, fields and industries.

Within this disclosure the term 'service' can be interpreted in one or more embodiments to encompass the manufacture, modeling, formulation, prescription, ordering, delivery, advertising, promotion, sale, distribution, transportation, administration, evaluation, recommendation, representation, description, transformation, packaging, receipt, disposal, storage or use of a product. Within this disclosure the terms 'provider' and 'service provider' can also be interpreted in one or more embodiments to encompass establishments which provide a service, and if used with a descriptor such as 'healthcare' (e.g., healthcare service provider, healthcare provider), can be interpreted to encompass establishments that provide a service within the market, field or industry indicated by the descriptor.

The terms 'database server' and 'server' are often used interchangeably within this disclosure. The terms 'pangenetic database', 'pangenetic database server' and 'pangenetic server' can be interpreted in one or more embodiments to encompass the respective database, database server and server of either an EMR, EHR or PHR. Within this disclosure the term 'features', as for example in pangenetic features and non-pangenetic features, can refer to the identities and values of characteristics and parameters such as nucleotides in a genomic sequence or a customer's zip code, and it can refer to data items (attributes) and data item values (attribute values) contained in a dataset (set of data), database (e.g., relational database) or database record.

Within this disclosure the term 'pangenetic' refers to genetic and epigenetic features. A genetic feature refers to any genome, genotype, haplotype, chromatin, chromosome, chromosome locus, chromosomal material, deoxyribonucleic acid (DNA), allele, gene, gene cluster, gene locus, genetic polymorphism, genetic mutation, genetic mutation rate, nucleotide, nucleotide base pair, single nucleotide polymorphism (SNP), restriction fragment length polymorphism (RFLP), variable tandem repeat (VTR), microsatellite sequence, genetic marker, sequence marker, sequence tagged site (STS), plasmid, transcription unit, transcription product, gene expression level, genetic expression (i.e., transcription) state, ribonucleic acid (RNA), and copy DNA (cDNA), including the nucleotide sequence and encoded amino acid sequence associated with any of the above. An epigenetic feature is any feature of genetic material - all genomic, vector and plasmid DNA and chromatin—that affects gene expression in a manner that is heritable during somatic cell divisions and sometimes heritable in germline transmission, but that is nonmutational to the DNA sequence and is therefore fundamentally reversible, including but not limited to methylation of DNA nucleotides and acetylation of chromatin-associated histone proteins. Within this disclosure the term 'non-pangenetic' refers to features other than genetic and epigenetic features.

FIG. 1 illustrates a Unified Modeling Language (UML) use case diagram for an embodiment of a pangenetic based profiling & selection system 100 which allows a plurality of consumers—consumer 1 (101), consumer 2 (102), consumer 3 (103) through consumer N (104)—to contribute pangenetic data to the system through contribute pangenetic data use case 110 which, in one embodiment, can be accomplished through transfer of pangenetic data associated with the individuals from electronic files such as those stored in the form of an electronic EMR, EHR PHR, or a portable genetic profile stored in computer readable form. Data indicating outcomes (e.g., subjective and objective measures of success and satisfaction) with respect to products, services and providers (including establishments) can be provided to the system through contribute outcome data for products, services and providers use case 112, in which data indicating success and satisfaction experienced by consumers 101-104 and success and satisfaction reported by provider 105, for example, can be contributed directly from those individuals or indirectly through records or profiles associated with those individuals. In determine associations between pangenetic data and product, service and provider outcomes use case 114, associations between subcombinations of the consumers' pangenetic data and outcomes experienced with each of the products, services and providers are computed by the system using the contributed pangenetic data associated with the consumers as well as the contributed outcome data regarding those products, services and providers. In request products, services and providers use case 116, consumer N 104 and provider 105 are able to individually request selection of one or more products, services and/or providers that will provide a desired outcome or outcome degree (i.e., high level of success and satisfaction) for consumer N 104. In identify products, services and providers that are a pangenetic match for the consumer use case 118, the system compares the pangenetic data associated with consumer N 104 against the subcombinations of pangenetic data that were previously determined through use case 114 to be associated with particular products, services and providers and the desired outcome, and identifies those that are an appropriate pangenetic match and outcome match for consumer N 104. In transmit products, services and providers use case 120, the identities of products, services and/or providers identified by the system as being appropriate for the consumer are transmitted to consumer N 104 and/or provider 105 to fulfill their request.

In one embodiment, use case 114 generates a dataset or database containing subcombinations of pangenetic data correlated with outcomes for particular products, services and/or providers by determining statistical associations (i.e., correlations) between subcombinations of pangenetic data and those entities. Pattern discovery methodology is designed for identifying patterns in large amounts of data such as genetic sequence data, and can therefore be used as part of the process of generating a database containing pangenetic based associations (correlations). With respect to the present invention, such pattern discovery methodology can be used to determine patterns within an individuals' pangenetic makeup that may be associated with successful outcome (e.g., a high level of success, a high level of satisfaction) with respect to particular products, services and providers. And, for example, once a pangenetic pattern associated with successful outcome with respect to one particular product is identified, that particular pangenetic pattern can be evaluated with respect to levels of success achieved by individuals having that particular pangenetic pattern that used alternative products. The set of pangenetic feature combinations (i.e., pangenetic patterns comprising genetic and/or epigenetic variations) corresponding to a particular product, service, provider or establishment can be considered to be a pangenetic based profile (or more simply 'pangenetic profile') of that product, service, provider or establishment.

One approach to determining associations between combinations of pangenetic data and outcomes experienced with products, services, providers and establishments is to first compute the average outcome achieved for each product, service, provider or establishment without regard to the associated pangenetic data. Then subsets of individuals that achieved higher or lower than average outcomes can be analyzed with respect to their pangenetic features to identify pangenetic feature combinations associated with those subsets of individuals. This enables the generation of pangenetic profiles which indicate pangenetic feature combinations that are correlated with combinations of particular outcome and particular product, service, provider or establishment. Products, services, providers and establishments can be then selected for another individual by comparing their pangenetic features (contained in their personal pangenetic profile) with the pangenetic patterns contained in the pangenetic profiles associated with the products, services, provider or establishments. Such a comparison can involve determining the strength of correlation between the pangenetic features of the individual and the pangenetic feature combinations contained in the pangenetic profiles. When making the comparison, partial matches of pangenetic data (e.g., a subset of pangenetic feature combinations) can be recorded and the best partial matches can be used to make a selection in instances when no complete or perfect match of pangenetic attributes is achieved. In one embodiment, determining the correlation between two sets of pangenetic data provides a correlation result that indicates the degree of identity (i.e., degree of matching/correlation) between the two sets of pangenetic data in the form of a quantitative or qualitative value. If a selection comprising a plurality of products, services, providers or establishments is desired, each of the plurality can also be scored (e.g., ranked) and/or ordered based on the extent of matching achieved between the individual's pangenetic data and the pangenetic feature combinations associated with each product, service, provider, or establishment. If certain pangenetic features are considered to have greater importance, those features can be more highly weighted in the scoring and ordering of the products, services, providers or establishments selected. The selected products, services, providers or establishments can be considered to be a match (i.e., appropriate) for the consumer if the result of the correlation between the individual's pangenetic data and the pangenetic feature combinations associated with each product, service, provider, or establishment exceeds a predetermined threshold, for example. The predetermined threshold for determining a match can require 100% identity or equivalence between a set of pangenetic feature combinations contained in the pangenetic profile of a product, service, provider or establishment and the individual's pangenetic data in order for the correlation between the two to be considered a match (thus requiring a complete set of the pangenetic feature combinations to be contained within the pangenetic data profile associated with the individual). Alternatively, the predetermined threshold for determining a match can specify a lower degree (less than 100%) of identity or equivalence between a set of pangenetic feature combinations contained in the pangenetic profile of a product, service, provider or establishment and the individual's pangenetic data in order for the resulting correlation between the two to be considered a match. The predetermined threshold can comprise a quantitative value, qualitative value, conditional statement or conditional expression (e.g., if-then construct), and/or mathematical statement (e.g., equality statement, inequality statement) to indicate the actual value and boundary characteristic of the threshold. The predetermined threshold can be predetermined by the method or system, or it can be predetermined by a user or administrator of the method or system.

In one embodiment of a computer based method for profiling a product, service, provider, or establishment, the system can access pangenetic data and outcome data associated with a plurality of consumers that received products or services, or interacted with service providers and establishments (the service providers can be establishments). The identities of the consumers can be masked or anonymized for privacy or security purposes. The service provider can be a healthcare provider, a non-healthcare provider, a medical provider, a non-medical provider, a clinical provider, and a non-clinical provider.

First, the pangenetic data and outcome data can be accessed in one database or across multiple databases. Further, the pangenetic data and outcome data may be contained in a single dataset (e.g., EHR, EMR or PHR containing pangenetic data) associated with each of the consumers, or the data may be contained across multiple datasets for each of the consumers. For example, the pangenetic data can be contained in datasets that are separate and distinct from the datasets containing the outcome data. The pangenetic data can be, for example, SNPs, nucleotides, base pairs, nucleotide sequences, gene sequences, genomic sequences, gene mutations, epigenetic modifications, epigenetic sequence patterns, and pangenetic based disorders, traits and conditions. Outcome data, which can be non-pangenetic data associated with the consumers, may include data such as consumer survey feedback, medical test results, clinical and non-clinical symptom gradings, success ratings, and satisfaction ratings, chemical measurements, physical measurements, physiological measurements, and psychological measurements, for example, which can be used directly as measures of success, or can be used to derive other measures of success. Measures of success can take the form of various types of scores (e.g., success levels) or values (e.g., symptom remediation percentages), as will be known to those of skill in the art, that provide at least some indication of the degree (level or magnitude) of success associated with an outcome. Measures of success can be based on subjective outcome data, such as success as judged by a service provider or satisfaction as rated by a customer, or they can be based on objective outcome data such as physiological measurements taken using a calibrated medical device. Success levels, which can take the form of standardized values and serve as measures of success, can be derived from other measures of success and may be represented as numerical/quantitative success levels (e.g., values on a scale of 1-10) or categorical/qualitative success levels (e.g., poor, fair, good, excellent). Outcomes as referred to in this disclosure can represent and be derived from various kinds of measures of success and have a range of values, including different levels of success (i.e., success levels). The range of outcomes utilized in developing correlations for the methods disclosed herein can be limited to 1) positive (i.e., successful) outcomes, 2) positive outcomes and neutral outcomes, or 3) positive outcomes, neutral outcomes and negative (i.e., unsuccessful) outcomes.

Next, based on the pangenetic data and outcome data the system can determine correlations between combinations of pangenetic data (i.e., pangenetic features) and outcomes experienced by the consumers with respect to each of the products, services, and service providers, to generate pangenetic based profiles of those products, services, and service providers. The determination of these correlations can be achieved by first comparing the pangenetic data associated with each of the plurality of consumers to identify pangenetic data combinations (combinations of pangenetic features) shared by subgroups of the consumers and then employing statistical measures known to those of skill in the art to compute the values for statistical correlations between the pangenetic data combinations and outcomes. Various statistical measures can be used to provide results which indicate the strength of the correlations as well as the statistical significance (confidence) of the correlations. Examples of statistical measures that provide values indicating the strength of correlations include probability, likelihood (odds), likelihood ratio (odds ratio), absolute risk and relative risk. Examples of statistical measures that provide values indicating statistical significance of correlations include standard deviation, standard error, confidence intervals, and p values. Values produced by statistical measures that provide an indication of probability of success/satisfaction can be also be used as outcomes, and provide the advantage of inherently indicate the chance of success associated with providing a particular product, service or provider for an individual with a particular pangenetic makeup.

As mentioned previously, there are algorithms known to those of skill in the art for identifying large patterns of genetic and epigenetic features shared between individuals, after which statistical measures can be applied to determine the strength of correlation with outcomes. The determination of shared (i.e., matching) pangenetic features requires determining the equivalence between features at the level of individual features and/or at the level of subcombinations of features. The determination of equivalence (i.e., a match, matching) between features can be an inflexible process that requires features to be identical, or it can be a flexible process that allows features to be non-identical if it is known that the difference between two non-identical features, or two non-identical combinations of features, does not significantly affect an outcome such as a particular phenotype (e.g., trait, response) or success level. For example, pangenetic data can be identified as being equivalent if the pangenetic data are epigenetic or genetic variations that are silent with respect to their effect on outcome or phenotype (e.g., gene sequences which differ by one or more silent nucleotide substitutions, mutations, or polymorphisms). Pangenetic data can also be identified as being equivalent if the pangenetic data are conservative genetic variations (e.g., conservative nucleotide substitutions, mutations, or polymorphisms occurring within the protein encoding 'open reading frame' of a gene sequence) that have no effect on the outcome or phenotype of interest. Pangenetic data can also be identified as being equivalent if the pangenetic data are non-conservative genetic variations (e.g., non-conservative nucleotide substitutions, mutations, or polymorphisms) that have the same effect on the outcome (e.g., phenotype) of interest. The above variations may occur within one or more gene coding regions or they may occur outside of gene coding regions (e.g., in non-coding 'junk DNA' regions of the genome).

Next, the system can transmit the pangenetic profiles containing the pangenetic data combinations correlated with outcomes experienced by the consumers in association with unique identifiers of the corresponding products, services and providers to provide pangenetic based profiles for those entities. The system can automatically chose, or be directed, to transmit the generated pangenetic profiles to at least one destination—a user, a database, a dataset, a computer readable memory, a computer readable medium, a computer processor, a computer network, a printout device, a visual display, and a wireless receiver—for the purpose of display, storage, or further processing and evaluation.

An embodiment of a computer database system for profiling a product, service or provider can comprise a memory having a first data structure containing pangenetic data and outcome data associated with a plurality of consumers that received products or services, or interacted with a service provider. The system can further comprise a processor for 1) generating, based on the pangenetic data and the outcome data, a pangenetic profile containing pangenetic data correlated with outcomes experienced by the consumers with respect the products, services or interaction with the service provider, and 2) transmitting the pangenetic profile in association with an identifier of the services, products or providers to provide a pangenetic based profile of the services, products or providers.

In a further embodiment, the method and system can utilize pangenetic profiles to rank or score the products, services and providers which correspond to those pangenetic profiles. This can be achieved, for example, by ranking or scoring based solely on the values of the success level correlations contained in the pangenetic profiles, without comparing the values of those correlations for different pangenetic profiles to one another. Alternatively, a plurality of pangenetic based profiles associated with a plurality of products, services and providers can be used to rank and score those products, services and providers based on a relative comparison of the corresponding success level correlations to one another with respect to a particular pangenetic feature combination (for example a particular pangenetic feature combination known to be associated with a particular health condition of interest such as cardiovascular disease). Based on the comparison, a normalized scoring and ranking system can be determined and used to assign scores and ranks to each of the products, services or providers.

In a further embodiment, the method and system can receive a request for recommendation of a product, service or provider for a consumer. The system can then access pangenetic data associated with the consumer and determine the correlation between that pangenetic data and the pangenetic data contained in the pangenetic profiles associated with relevant products, services or providers. When the correlation exceeds a predetermined threshold which can be determined by the system or designated by the user, the system can transmit an indication (i.e., output a notification) identifying the particular product, service or provider achieving that correlation as being recommended for the consumer. As discussed previously with respect to determining correlations for the purpose of generating pangenetic profiles, the comparison of pangenetic profiles to determine correlations can comprise identifying pangenetic data associated with the consumer that is equivalent (a match) to pangenetic data contained in pangenetic profiles associated with products, services or providers. Determining the correlation can further comprise identifying the amount and/or type of pangenetic data that is equivalent, if the match is imperfect, in order to further determine the degree of correlation (i.e., extent of correlation).

In one embodiment, the selection or recommendation of services or providers by the system can be used in the generation of pre-authorizations, pre-certifications or pre-determinations issued by an insurer. As described by the American Medical Association (AMA) for example, a pre-authorization is a preliminary authorization issued by an insurer "to establish that the insurer's medical necessity guidelines have been met for the proposed service", the service being "in-office and/or outpatient diagnostic tests and surgical procedures".

Currently, a service code (e.g., Current Procedural Terminology (CPT) codes) for the proposed service and a primary diagnosis code (e.g., International Classification of Diseases, 9th Revision, Clinical Modification (ICD-9-CM) code) must be submitted to the insurer along with identifying information of both the patient (e.g., patient's name, ID and plan/group name or number) and the healthcare provider (i.e., provider tax ID, provider Personal Identification Number (PIN)), a brief history of the current illness, and the date, type and place of the proposed service. As described by the AMA, a pre-certification is a preliminary certification to "verify that the service meets the health insurer's medical necessity criteria", the service being a "hospital admission and/or surgical procedure". The additional information described above for a pre-authorization is also required for a pre-certification. As described by the AMA, a pre-determination is a preliminary "determination of a patient's coverage for a specific service or procedure", and "pre-determinations are the only payment guarantee that a physician practice might receive from a health insurer" further "subject to the member's benefits and eligibility at the time of service, as well as subject to whether the member has exceeded the health insurer's maximum benefits". In addition to the information required above for a pre-authorization, a pre-determination further requires the submission of the estimated cost of the proposed service, the "length of time the patient has been under the physician's care", and a "detailed history of the patient's present illness, including subjective and objective findings, previous treatment, exam finding and outcome (if applicable), and medical necessity". In one embodiment, the recommendation of a service provider for a consumer can be used by the pangenetic based system or another system to generate an approval for rendering payment to the service provider. In addition to being used to generate a payment approval, the indicated recommendation can also be used to generate a payment approval request, or to generate a financial transaction or insurance claim, for example.

FIG. 2 illustrates one embodiment of pangenetic profiles for pangenetic based selection of services for treating consumers with hypertension (high blood pressure). Three different services are included in the table of FIG. 2. as 'provide treatment' service options. The first three records (i.e., rows) constitute a pangenetic based profile of a 'provide exercise therapy' service option. The middle three records constitute a pangenetic based profile of a 'provide dietary counseling' service option. The last three records constitute a pangenetic based profile of a 'provide drug E' service option. The pangenetic based profiles include consumer pangenetic feature combinations correlated with outcomes in the form of two types of measures of success, namely percent success (% success) and success level. In this example, percent success is a measure of success which indicates the percentage of consumers (patients) with the indicated pangenetic feature combination that received the service and then experienced remediation of their hypertension symptoms. For example, the table indicates that providing exercise therapy to a consumer possessing pangenetic combination {Rs4961=(T;T); Rs5186=(C;C); Rs3865418=(T;C)} will have a 47% chance of success of eliminating their hypertension condition/symptoms. It should be noted that non-pangenetic data, such as recommended age range for the services or adverse interactions, can be included in the dataset to filter out potential services that are not compatible or appropriate for non-pangenetic features associated with a consumer. For example, Drug E may not be appropriate for use in the very elderly or in those taking certain medications that interact adversely with Drug E.

As will be apparent to those skilled in the art, many different measures of success can potentially be derived including success ratings computed by combining a plurality of numerical (i.e., quantitative) or categorical (i.e., qualitative) values for a plurality of factors. For example, a panel of various clinical test results and/or a set of symptom evaluations (gradings) associated with a health condition before and after providing a service can be used to derive a combined computational measure or an overall verdict indicating success or failure, or even the degree of success or failure, of the provided service in treating the health condition. Further, the determination of success may be based on evaluations provided by the customer, provider or establishment, or a combination thereof. Where evaluations of the success of a service or provider are obtained from multiple sources (e.g., from customer, provider and/or a third party), the results of the evaluations can be indicated separately in the dataset, or they can be used to derive a single value for outcome by averaging or weighted averaging of the evaluations, for example. Success level is a measure of success that can take the form of standardized score, for example on a scale of 1 to 10 (10 being the best). With respect to FIG. 2, success level is derived from percent success data by rounding percent success values to the nearest whole multiple of ten, and then dividing by ten. As such, the pangenetic combination in the first record of the table is correlated with a success level of 5, which in this case is a medium success level, for successful treatment of hypertension by providing exercise therapy. In one embodiment, success level can directly indicate how appropriate (how good of a match) a service or provider is for a consumer having the corresponding pangenetic feature combination.

As disclosed elsewhere in this application, the outcome data used to derive outcomes such as success levels can include considerably more varied and complicated measures of success than percentage satisfaction or percent success. Even a satisfaction rating can be derived from a complex computation which combines a plurality of ratings for factors such as product cost, ease of product usage, number of side effects, severity of side effects, number of symptoms resolved and speed of symptom resolution, each of which can contribute to the result calculated for a combined computational measure or overall verdict regarding satisfaction or dissatisfaction, or even the degree of satisfaction or dissatisfaction with the product. While the types of outcome data presented in the above example are limited to percent success and success level, other types of outcome data can be collected, computed and used to indicate outcomes experienced with products, services, providers and establishments, as will be apparent to those skilled in the art.

FIGS. 3A-C illustrate pangenetic based rank-ordered tabulations (listings) of services for consumers that can be generated for transmission as output by one or more embodiments of the methods and systems disclosed herein. In general, ranks can be assigned to simplify the selection of one or more services or providers from a plurality of services or providers correlated with a particular pangenetic combination. Tabulations such as rank listings can then be created with services or products presented in order of rank (i.e., rank-ordered). Rank can derived directly from outcomes or measures of success such as success levels. In the current example presented in FIG. 3A with respect to a consumer having pangenetic SNP combination {Rs4961=(T;T); Rs5186=(C;C); Rs3865418= (T;C)}, providing drug E ranks as the first choice (i.e., best choice), providing exercise therapy ranks as the second choice, and providing dietary counseling ranks as the third choice. Similarly, tabulations for consumers having two other pangenetic feature combinations along with corresponding measures of success are illustrated in FIGS. 3B and 3C. A tabulation of services for a consumer possessing one of the indicated pangenetic combinations can be transmitted with the services ordered according to rank. While the tabulations illustrated in FIGS. 3A-C contain a wide variety of information, such tabulations can contain only a portion of the information shown, and can also contain other types of pangenetic and non-pangenetic information that are not described or shown in these examples. In these three tabulations, ranks were assigned based on success level, however they also correspond to the relative values of percent success because percent success was the only outcome data used for computing success levels in this example. However, if the example had relied on two different measures of success to compute success levels, for example percent satisfaction (e.g., feedback from consumers) in addition to percent success of treatment (e.g., evaluations from providers), success levels computed by averaging the two types of data may have indicated a different rank order of the services than what would be indicated based on either percent satisfaction or percent success alone. Other data such as pricing or recommended age range can be included in the determination of rank so that services that are more appropriate (a better match) for an individual's non-pangenetic characteristics/preferences are assigned a higher rank or lower rank than that determined based on pangenetic correlations alone.

FIG. 4 illustrates one embodiment of an example of pangenetic profiles for pangenetic based selection of healthcare providers for treating diabetes and hypertension. The data are organized into pangenetic combination records associated with different services administered by the providers. While it is not essential to include the services in pangenetic profiles of providers, this example demonstrates how both data can be integrated within the same pangenetic profiles. The providers are identified by their provider IDs, which in this case are their actual names but could be, for example, numeric codes keyed (i.e., linked) to their actual identities contained in a separate dataset or database. Pangenetic feature combinations, listed in the form of SNP combinations, are shown along with corresponding outcomes. The corresponding outcomes that are indicated include percent success, percent satisfied and overall scores for each of the provider/service/disorder/patient SNP combination records. While the types of outcome data presented in the above example and the following example are limited to percent success, percent satisfied and score, other types of outcome data can be collected, computed and used to indicate outcomes experienced with products, services, providers and establishments, as will be apparent to those skilled in the art. In the present example, the individual scores for each provider/SNPs combination were computed by adding the value for percent success to the value for percent satisfied for a particular provider/SNPs combination and then dividing by two to obtain an average value. However, as will be apparent to those skilled in the art, values for scores can be based on a scale of 1 to 10, or they can be normalized to other score values in the dataset, for example. The score values can also be based on additional parameters such as undesirable product or service interactions in circumstances where product and services are relevant to provider selection (or product, service or establishment selection). Score values can also be designed to represent outcome ranking of a particular provider/pangenetic combination with respect to all provider/pangenetic combinations, or with respect to only those provider/pangenetic feature combinations having the same pangenetic features in common, or with respect to only those provider/pangenetic combinations having the same provider in common (and this concept generally applies to the selection of products, services and establishments as well). Additionally, zip codes for the providers are indicated and can be used to either filter out a provider from being a potential selection for an individual, or alternatively, can be used to filter out a provider that was initially selected for an individual based on pangenetic data alone but is deemed undesirable because they have an office location which will be inconvenient for the patient. The particular services provided, as indicated in the each of the records, can also be used for filtering, for example to restrict selection to providers which tend to either favor or avoid the use of particular treatments. Similarly, other data associated with the providers such as average service charge and insurance plan participation information could be included in the attribute profiles to further filter potential selections.

FIG. 5 illustrates one embodiment of an example of pangenetic profiles for pangenetic based selection of healthcare establishments for the treatment of diabetes and hypertension. To demonstrate how pangenetic based profiles for establishments can be essentially the same as for individual providers, the only difference of this table from that of FIG. 3 is the substitution of provider IDs with establishment IDs. A set of pangenetic profiles containing both individual provider IDs and provider establishment IDs can also be created where both types of information are contained within the same records, for example. The establishments are identified by establishment IDs, which in this case are their actual names but could be, for example, numeric codes keyed (i.e., linked) to their actual identities contained in a separate dataset or database. Groups of patients having each disorder are indicated and are divided into subgroups based on patients' pangenetic features, listed in the form of SNP combinations for this example, that were determined to be associated with a particular outcome (e.g., higher or lower than average outcome) experienced with respect to the indicated healthcare establishments. The indicated outcome data include percent success, percent satisfied and overall scores for each of the establishment/disorder/patient SNP combination subgroups, with scores computed as in the previous example with respect to FIG. 4. Additionally, zip codes for the healthcare establishments are indicated and can be used to either filter out a particular establishment from being a potential selection for an individual, or alternatively, can be used to filter out an establishment that was initially selected for an individual based on pangenetic data alone but is deemed undesirable because it's location will be inconvenient for the patient or patient's family to access. The identities of the treatments received by each subgroup are indicated and can also be used for filtering, for example to restrict selection to providers which tend to either favor or avoid the use of particular treatments. Similarly, other data associated with the healthcare establishments such as average service prices and insurance plan participation information can be included to further filter potential selections.

Of many possible embodiment of a system for selecting products, services, providers and establishments, the two embodiments that follow differ from each other primarily with respect to intended user types. One system embodiment is designed for the individual (i.e., consumer or patient) as the user and can be implemented on a Personal Computer (PC) or wireless computing device connected to the internet, through which communication with the system's applications and databases is made possible, for example via the world wide web. A second system embodiment is designed for a provider as the user. For example, in the healthcare field a medical provider or an administrator at a medical establishment can be the user and can interact with the system through a PC or workstation computer located in an office, clinic or hospital, or through a wireless computing device. The PC, workstation, or wireless computing device can be connected to a WAN or the internet, through which communication with the system's applications and databases is enabled.

With regard to the first system embodiment, ratings of success or failure of particular products and services, as well as ratings of satisfaction or dissatisfaction with particular service providers and establishments, can be provided through voluntary feedback by the consumer, preferably entered as input into the system by the consumer. With regard to the second system embodiment, such rating information can be provided by medical professionals through, for example, results of phase III clinical trials with respect to new therapies, drugs and devices. With respect to established therapies, drugs and devices, such information can be provided by medical professionals through medical examinations and records generated during the course of therapy, doctor-patient interviews, patient follow up studies, and patient surveys. Alternatively, customer ratings of treatment success and satisfaction with service providers and establishments can also be collected and entered into the system by one or more third parties.

Figure 6:
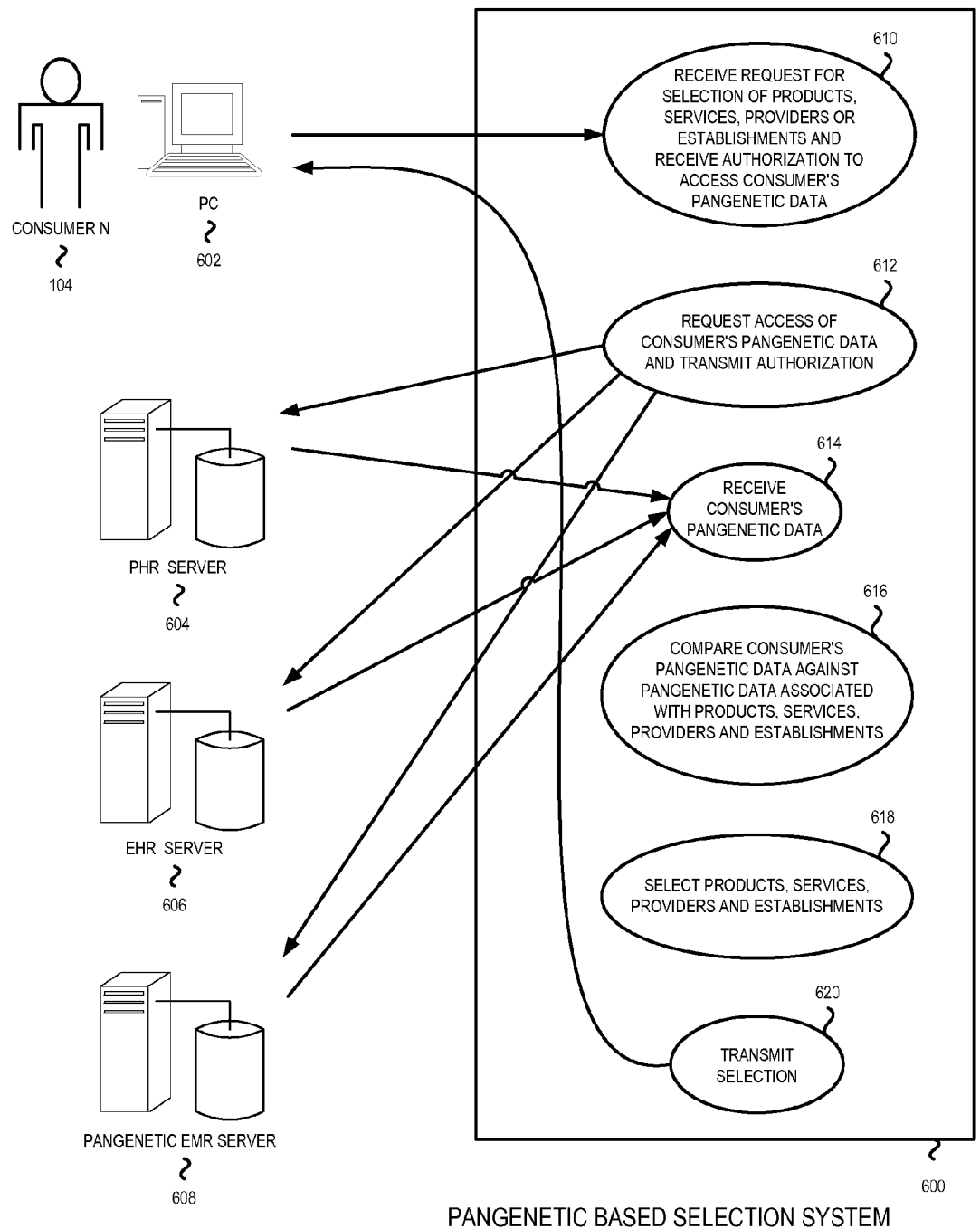
FIG. 6 illustrates a pangenetic based selection system for use by a consumer.

FIG. 6 illustrates a UML use case diagram depicting a first system embodiment in which a pangenetic based selection system 600 allows a consumer N 104 to request selection of products, services, service providers and establishments. In receive request for selection of products, services, providers or establishments and receive authorization to access consumer's pangenetic data use case 610, using the PC 602 the consumer N 104 inputs a query request and an authorization to enable the pangenetic based selection system 600 to access their pangenetic data. The request can also include parameters such as zip code and age that can be used to filter potential selections. The pangenetic based selection system 600 transmits a request for pangenetic data and authorization to the database server where the pangenetic data of the consumer N 104 is stored, for example to PHR server 604, EHR server 606 or Pangenetic EMR server 608, and either receives a copy of the pangenetic data from the database server or is granted access to read the pangenetic data directly on the database server which contains the pangenetic data. In compare consumer's pangenetic data against pangenetic data associated with products, services, providers and establishments use case 616, the pangenetic data of consumer N 104 is compared against one or more datasets stored in one or more databases of the pangenetic based selection system 600 which contain combinations of pangenetic data associated with the products, services, providers or establishments that are relevant to the request by consumer N 104 and are therefore potential candidates for selection. In select products, services, providers and establishments use case 618, the best matches obtained by the comparison (e.g., the largest number of pangenetic features in common between consumer N 104 and combinations of pangenetic features associated with relevant products, services, providers or establishments) can be selected, or can be further subjected to filtering according to specified parameters to obtain a final selection. Once one or more products, services, providers or establishments are selected to fulfill the query request, in transmit selection use case 620 the identifiers of the one or more selections can be transmitted to the PC 602 for storage, printout and/or display, or for further transmission to other individuals, establishments or devices as dictated by consumer N 104.

Figure 7:
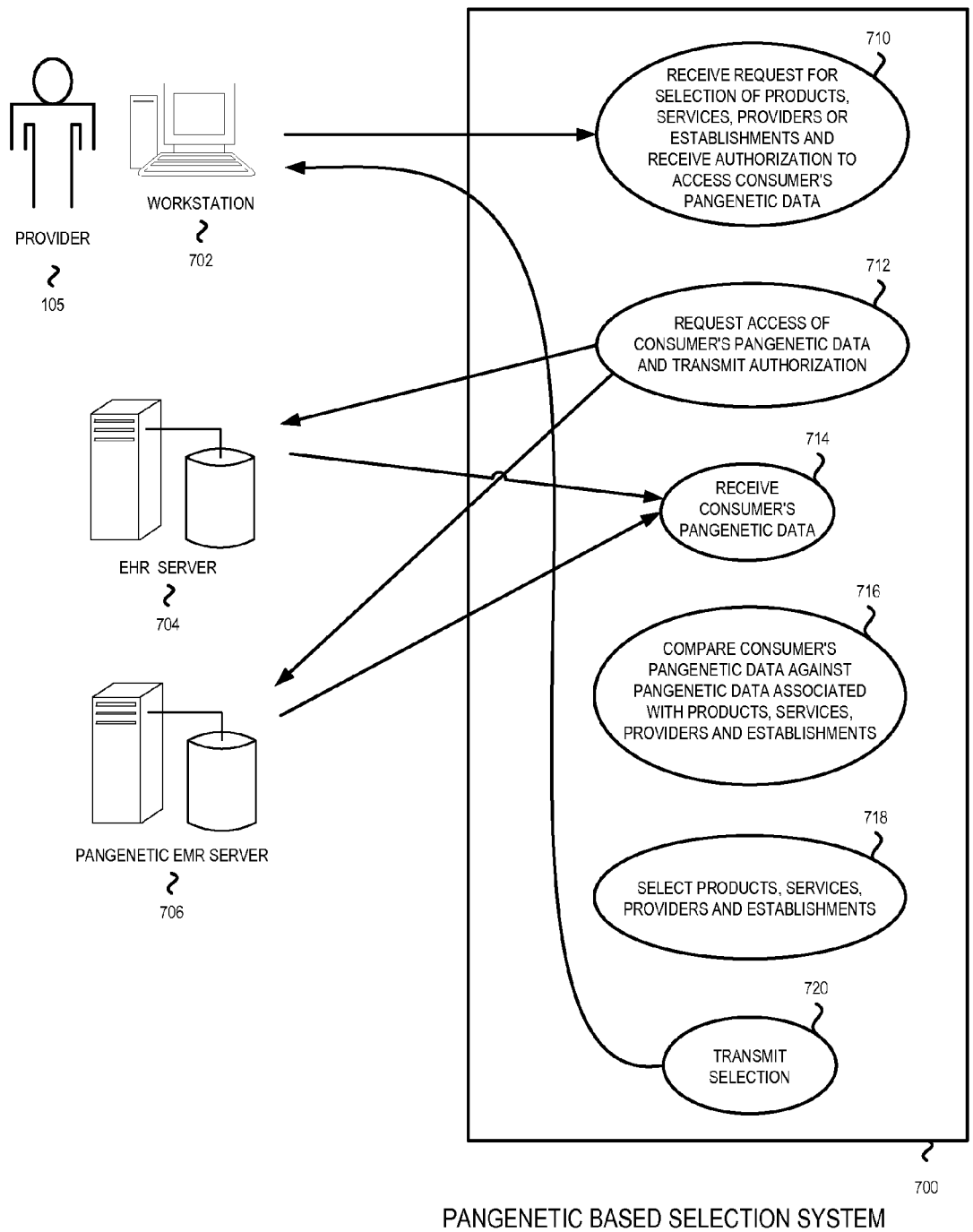
FIG. 7 illustrates a pangenetic based selection system for use by a provider.

FIG. 7 illustrates a UML use case diagram depicting a second system embodiment in which a pangenetic based selection system 700 allows the provider 105 to request selection of products, services, service providers and establishments for a consumer. In receive request for selection of products, services, providers or establishments and receive authorization to access consumer's pangenetic data use case 710, using workstation 702 the provider 105 inputs a query request and an authorization to enable the pangenetic based selection system 700 to access the consumer's pangenetic data. The request can also include parameters such as zip code and age that can be used to filter potential selections. The pangenetic based selection system 700 transmits a request for pangenetic data and authorization to the database server where the pangenetic data of the consumer is stored, for example to EHR server 704 or Pangenetic EMR server 706, and either receives a copy of the pangenetic data from the database server or is granted access to read the pangenetic data directly on the database server which contains the pangenetic data. In compare consumer's pangenetic data against pangenetic data associated with products, services, providers and establishments use case 716, the pangenetic data of the consumer is compared against one or more datasets stored in one or more databases of the pangenetic based selection system 700 which contain combinations of pangenetic data associated with the products, services, providers or establishments that are relevant to the request by the provider 105 and are therefore potential candidates for selection. In select products, services, providers and establishments use case 718, the best matches obtained by the comparison (e.g., the largest number of pangenetic features in common between the consumer and combinations of pangenetic features associated with relevant products, services, providers or establishments) can be selected, or can be further subjected to filtering according to specified parameters to obtain a final selection. Once one or more products, services, providers or establishments are selected to fulfill the query request, in transmit selection use case 720 the identifiers of the one or more selections can be transmitted to workstation 702 for storage, printout and/or display, or for further transmission to other individuals, establishments or devices as dictated by the provider 105.

The transmitted selections of products, services, providers and establishments can be used directly by the consumer or provider to purchase, prescribe, recommend or sell a product or service, or schedule an appointment, for example. The selections can also be used to reference the associated combination of pangenetic features of the consumer that resulted in the selection, and both the selection and the associated combination of pangenetic features can be subsequently transmitted to another party or another system for further processing and evaluation. For example, the pangenetic features of a patient that matched pangenetic data associated with a particular medication, medical device, or medical service selected by the system for that patient can be transmitted by their physician to an insurance company to request approval for payment for that medication, medical device, or medical service. The information can also be transmitted for the purpose of other financial transactions such as billing and pricing for example.

Figure 8:
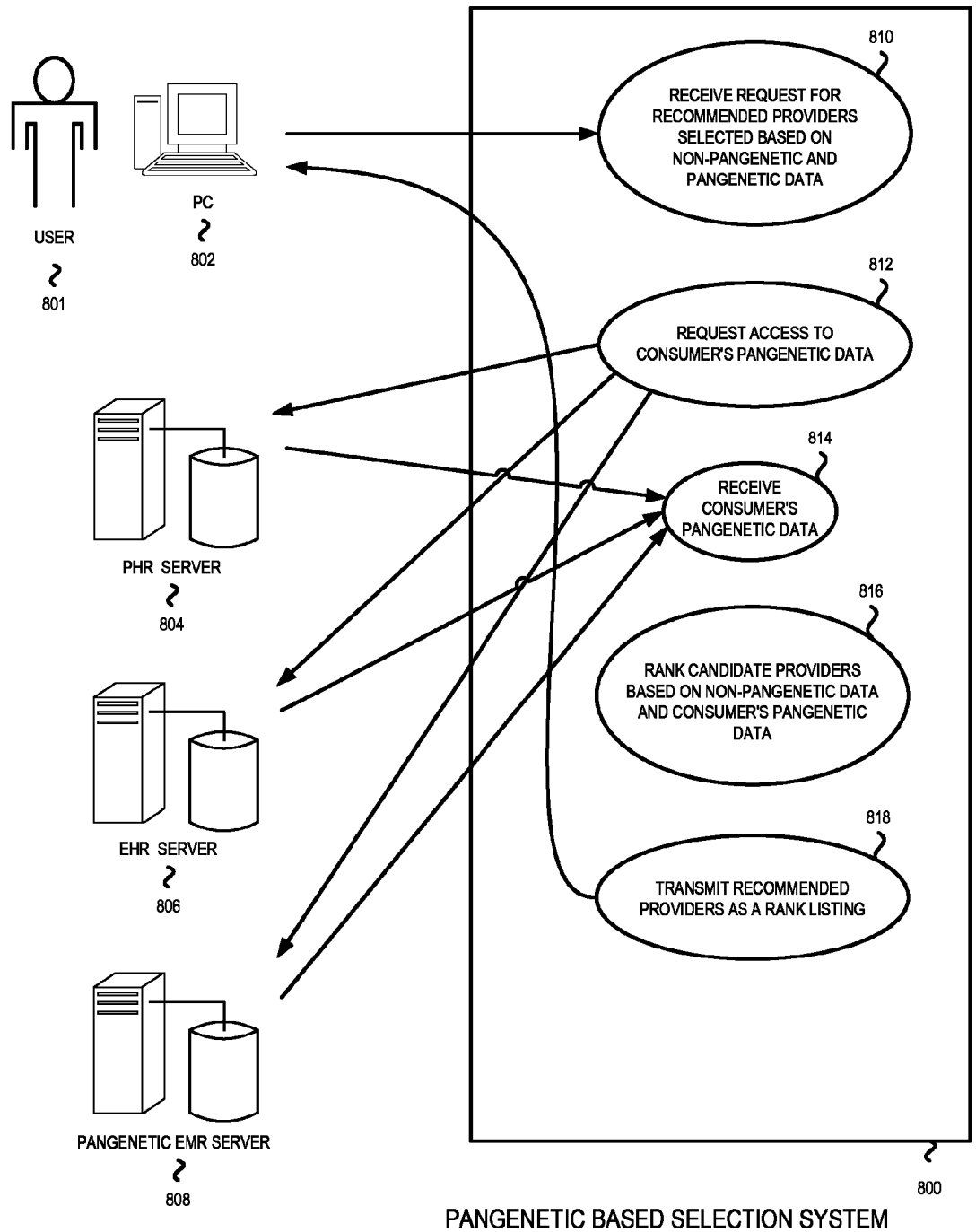
FIG. 8 illustrates a pangenetic based selection system incorporating non-pangenetic selection.

FIG. 8 illustrates a UML use case diagram depicting a system embodiment in which pangenetic based selection system 800 allows User 802 via PC 804 to enter a request for recommended service providers for a consumer based on pangenetic and non-pangenetic information. This embodiment allows for pangenetic based selection system 800 to reside in any number of locations including PHR server 804, EHR server 806, or pangenetic EMR server 808, and any of the preceding can be hosted and operated by an insurer or other party. In receive request for recommended providers selected based on non-pangenetic and pangenetic data use case 810, the system receives the user's query including user specified non-pangenetic features such as zip code and gender of the preferred service provider. In request access to consumer's pangenetic data use case 812, the system either prompts the user to supply an authorization to access a consumer's pangenetic data profile which is then passed to the respective server which contains the pangenetic information, for example PHR server 804, EHR server 806, or pangenetic EMR server 808, or alternatively the system passes on a stored pre-authorization, in either case to receive access to the consumer's pangenetic data. In one embodiment, the system and pangenetic server are hosted together or integrated such that no request for access to the consumer's pangenetic data is required, only an initial logon preceding the request use case 810 in which the user is authenticated and access by the system to pangenetic data of one or more consumers automatically granted upon authentication of the user by the system. In receive consumer's pangenetic data use case 814, the system receives access to at least a portion of the consumer's pangenetic data, either by accessing and reading a database or file containing the pangenetic data, or alternatively, by receiving a file, packet of data, or data mask containing the relevant pangenetic data necessary to enable the recommendation of a service provider for the consumer. In rank candidate providers based on non-pangenetic data and consumer's pangenetic data use case 816, a list of potential providers for the consumer are filtered and ranked based on non-pangenetic features and pangenetic features. In this example, non-pangenetic features such as zip code and gender are used to filter and rank a list of providers in an attempt to satisfy the preferences of the user or consumer for the preferred characteristics of the provider. Other non-pangenetic features for potentially filtering service providers can be insurer networks, field of specialty, years in business/practice (i.e., experience), number of malpractice/law suits, work schedule and availability, and relative price bracket, for example. When one or more providers meet the preferred provider features specified by the user, providers which do not those preferences may be filtered out completely or may be included on a list of providers in which they receive a lower rank that the providers which better met the preferred features. The providers are also filtered based on pangenetic features by comparing their provider pangenetic profiles, which contain pangenetic data (combinations of pangenetic features, pangenetic data patterns) associated with outcome measures, against pangenetic data associated with the consumer. While in other embodiments the selection of recommended providers can be performed with only a pangenetic data comparison, or only non-pangenetic data comparison, when utilizing both types of evaluations it is possible for the comparison of pangenetic data to be performed before, after, or simultaneously with the non-pangenetic data comparison to achieve potentially different selection results. In transmit recommended providers as a rank listing use case 818, the providers selected as a result of pangenetic and non-pangenetic filtering and comparison are transmitted as a list (i.e., tabulation) of potential providers for the consumer in which the providers are ordered or numbered based on a simple numerical rank or scored based on the extent (i.e., degree, percentage) of non-pangenetic and/or pangenetic data matching between the consumer and each of the providers. The scoring can be a normalized score, a simple rank, or an actual percentage indicating the degree of identity (i.e., match) between compared features, for example. If the filtering and comparison are non-stringent so that non-optimal providers are included in the list, the included ranking can enable the user to then select the most appropriate providers. A final selection by the user can be aided by making features of the included providers a visible or accessible (e.g., hyperlink accessible) part of the list, in addition to the scoring, ranking or rank ordering the providers. Alternatively, the filtering and comparison can be made sufficiently stringent or a threshold for rank imposed such that only the most appropriate providers are transmitted in the recommendation. For example, only one provider (i.e., the most appropriate/suitable provider, the highest ranking provider) or a small subset of providers (e.g., the top five optimal providers by rank) may be transmitted. The preference of how many providers should be returned by the system in response to the user's query can be specified by the user or the system and can be based on criteria such as the total number of providers that are initially identified as suitable matches for the consumer, or alternatively, the disparity or spread between respective scores or degree of matching of the providers. If only the highest scoring/ranking provider is selected by the system for transmission as output, then the list that is transmitted would contain only that single provider. While FIG. 8 describes the recommendation/selection of one or more service providers, it is also applicable to the recommendation/selection of products, services, and establishments.

Figure 9:
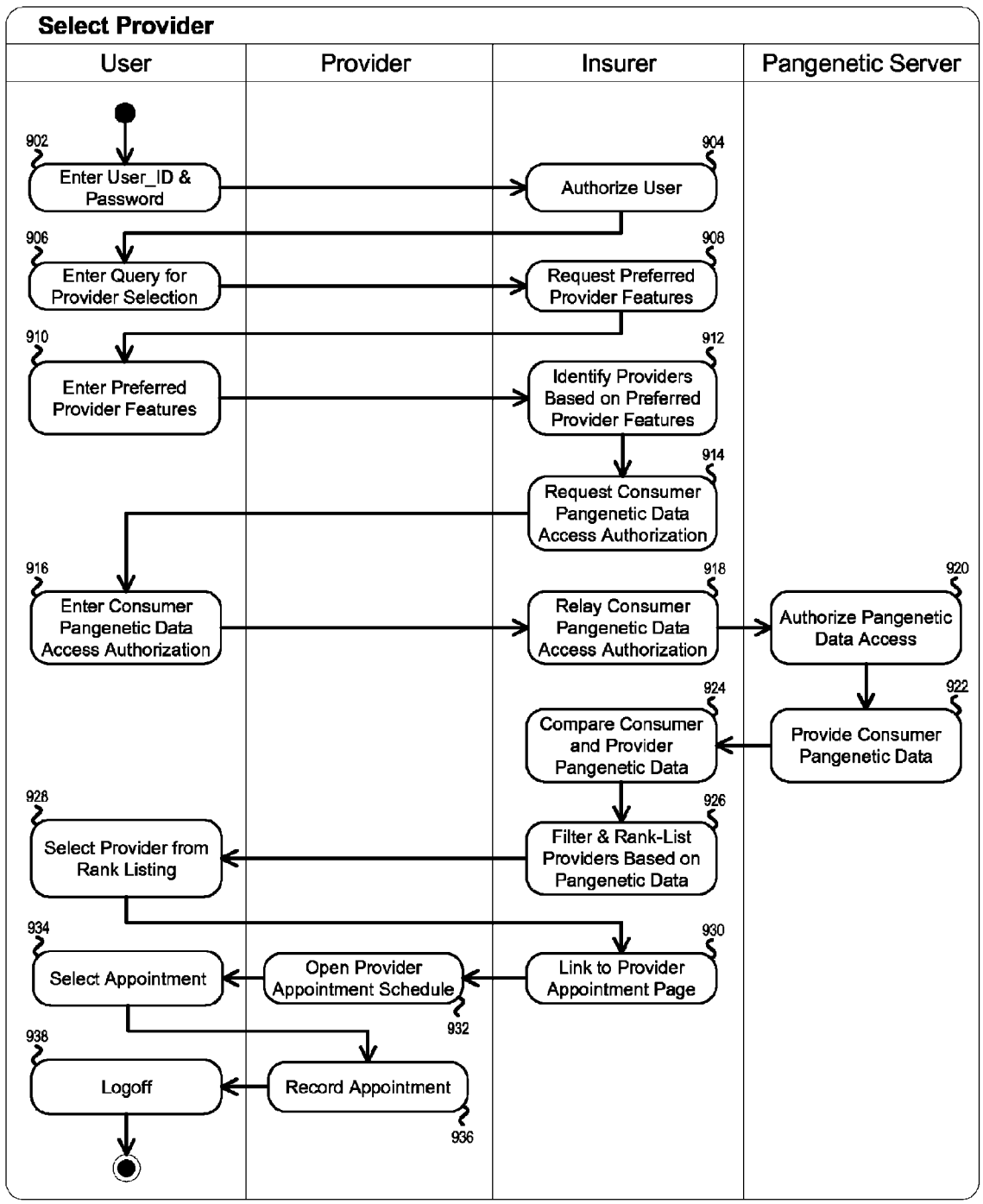
FIG. 9 illustrates a first activity diagram depicting pangenetic based selection of a provider.

FIG. 9 illustrates a UML activity diagram for one embodiment of service provider selection. In the particular embodiment of 'select provider' represented in this figure, the insurer hosts the portion of the pangenetic based selection system which performs comparisons between the pangenetic data of the consumer and candidate providers. In enter user_ID & password step 902, a user such as a patient (i.e., consumer), healthcare professional, or insurer representative gains secure access to the system by logging on to the system with their secure personal login identifiers. This login information can alternatively be in the form of other secure login procedures such as retinal or fingerprint scan, or a personal identification card that is based on magnetic or radio frequency identification (RFID) technology. In authorize user step 904, the user logon information is verified and access is granted if the security information passes verification. In enter query for provider selection step 906, the user enters a request for selection of one or more providers. In request preferred provider features step 908, the system queries the user for desired features of the provider, particularly non-pangenetic features. In enter preferred provider features step 910, the user can enter preferences for location, price bracket, specialty and gender of providers, for example. In a further embodiment, these preferences may be specified by the user to be inflexible requirements for selection of a provider, so that a provider must match these specified preferences in order to be a candidate for further pangenetic based selection. Alternatively, these preferences can be treated as flexible so that in circumstances when only a small number (or none) of the providers in the system database match all of the user's preferences, then providers that meet (or approximately meet) some of the preferences are also included to provide at least some viable choices for the user to select from. In identify providers based on preferred provider features step 912, the system identifies (i.e., flags, stores or tabulates) candidate providers for the customer based on the user specified set of preferred provider features. As an example in the healthcare field, a user request for a female general practitioner located within a particular zip code invokes the system to identify candidate providers for the consumer that match the desired gender, subspecialty and location. The preference for specialty may be an inflexible requirement. However, flexibility can be incorporated with respect to the other preferred features. For example, if a request for a female general practitioner located in a specific zip code would return a null result, then the system may identify candidate providers comprising 1) male general practitioners located within the desired zip code, and 2) female general practitioners located within reasonably close proximity to the desired zip code. This example exemplifies how flexibility can be incorporated with respect to multiple desired features as when no providers meet all the preferred features or when a provider matches some of the features (e.g., specialty) but not others (e.g., gender and location). This step of identifying providers can include, for example, scoring, ranking or ordering the providers based on the preferred features (i.e., based on the extent to which the preferred features are possessed by each candidate provider). In a further embodiment, the user or system can be allowed to decide which preferred features are inflexible, which are flexible (and to what extent they are flexible, such as the maximum allowable distance of a provider from a desired zip code location), and which have priority in scoring, ranking and/or ordering of the results. It should be noted that the above step of identifying providers based on user specified preferred features precedes the following steps of pangenetic based comparison and selection, and can therefore serve as a pre-selection step if used to filter out providers from further consideration by the steps that follow. However, this step can also be relocated in the activity diagram sequence to follow the pangenetic based comparison and selection steps if, for example, the user, customer, providers, insurer or system deem pangenetic based selection to be the more important determinant for selection of the best provider for the customer.

In request consumer pangenetic data access authorization step 914, the user is queried by the insurer's system to identify the consumer for whom the selection is intended as well as to provide authorization/permission to access that consumer's pangenetic information. In enter consumer pangenetic data access authorization step 916, the user responds to the system's request for access to consumer pangenetic data by inputting an identifier of the consumer, access code, and/or user_ID and password security information associated with the user or consumer in order to allow the system to access at least a portion of the pangenetic data associated with the particular consumer for whom a provider is being selected. In relay consumer pangenetic data access authorization step 918, the system receives the identifier information and/or access authorization needed to access the pangenetic data of the consumer and passes at least a portion of that information along with a request for access to the relevant pangenetic data of the consumer to a pangenetic server (e.g., an EMR, EHR or PHR database server) where that pangenetic data is stored. In authorize pangenetic data access step 920, the pangenetic server verifies the validity of the access request. This verification can include authenticating the insurer database server submitting the request to ensure the request is coming from a valid or pre-authorized entity. In provide consumer pangenetic data step 922, the pangenetic based selection system hosted by the insurer can either be granted access to read one or more pangenetic data files associated with the consumer (e.g., a genetic profile of the consumer), or alternatively, all or a portion of the pangenetic data files associated with the consumer can be transmitted to the pangenetic based selection system on the insurer's server. In compare consumer and provider pangenetic data step 924, the pangenetic based selection system compares provider associated pangenetic data contained in a database of the system (the provider associated pangenetic data having been previously correlated with one or more measures of success) with the consumer associated pangenetic data that was provided by the pangenetic server. The comparison is designed to determine matches between pangenetic features contained in the two sets of pangenetic data. Matching pangenetic features can be defined as pangenetic features that are identical between the two sets of data, or they can be defined non-stringently as pangenetic features that are equivalent between the two sets of data. As disclosed previously, pangenetic features that are not identical can be considered equivalent if they have the same or essentially the same effect on relevant outcomes, responses or phenotypes. In filter & rank-list providers based on pangenetic data step 926, the system filters and ranks candidate providers based on the results of the pangenetic comparison and can transmit the providers as a list or tabulation. With respect to filtering the providers, if the consumer's pangenetic features are a poor match to those associated with a particular provider, then that provider can be eliminated (i.e., filtered out) during this step. Providers which match a considerable portion of pangenetic features of the consumer can be evaluated with respect to the degree of similarity (i.e., percent identity of the set of features) shared with the consumer and then scored, ranked and/or ordered relative to each other, for example. Matching between certain pangenetic features can be given greater weight for the purpose of scoring, ranking and/or ordering, for example in circumstances where certain pangenetic features are known to have greater influence on the customer's condition or needs, or the desired outcome. The list can indicate categories or types of pangenetic features that matched and to what degree, and can also indicate the values of non-pangenetic features for providers in the list and the extent of matching with the consumer's preferences with respect to those features. In one embodiment, the user can be provided with options to adjust parameters such as weighting and priority of features to influence the values for scores and ranks of the individual providers or the order of the providers as listed in the tabulation. In select provider from rank listing step 928, the user selects one or more of the providers presented to them by the system based simply on rank or score, or based on a further evaluation of the type and extent of pangenetic and non-pangenetic features which matched between the consumer and each of the providers. In link to provider appointment page step 930, the provider selected by the user is used to direct the user to a scheduling page on a webpage hosted by the provider or another party on behalf of that provider. In open provider appointment schedule step 932, the provider website opens the scheduling page so that available appointment dates and times are displayed or otherwise presented to the user. Alternatively, the page may request contact information that will be used by the provider to contact the user or customer in response to a request to schedule an appointment with the provider. In select appointment step 934, the user selects an appointment, if a suitable appointment is available, or otherwise sends a request to the provider indicating that an appointment or consultation is desired. In record appointment step 936, the appointment or request for an appointment entered by the user is recorded on the provider's server or on the server of the party acting on behalf of the provider. In logoff step 938, the user logs out to end the session and terminates secure access to the system. This logoff step can be automated based on closing the application or moving out of range of an optical sensor or RFID sensor which detects the presence of the authorized user to ensure that an unauthorized user does not inadvertently gain access the consumer's pangenetic data or pangenetic based results, thereby ensuring that strict doctor-patient privacy can be maintained in a healthcare setting, or ensuring in a public setting that others do not gain access to an individual's pangenetic data through an easily captured mobile device for example.

Figure 10:
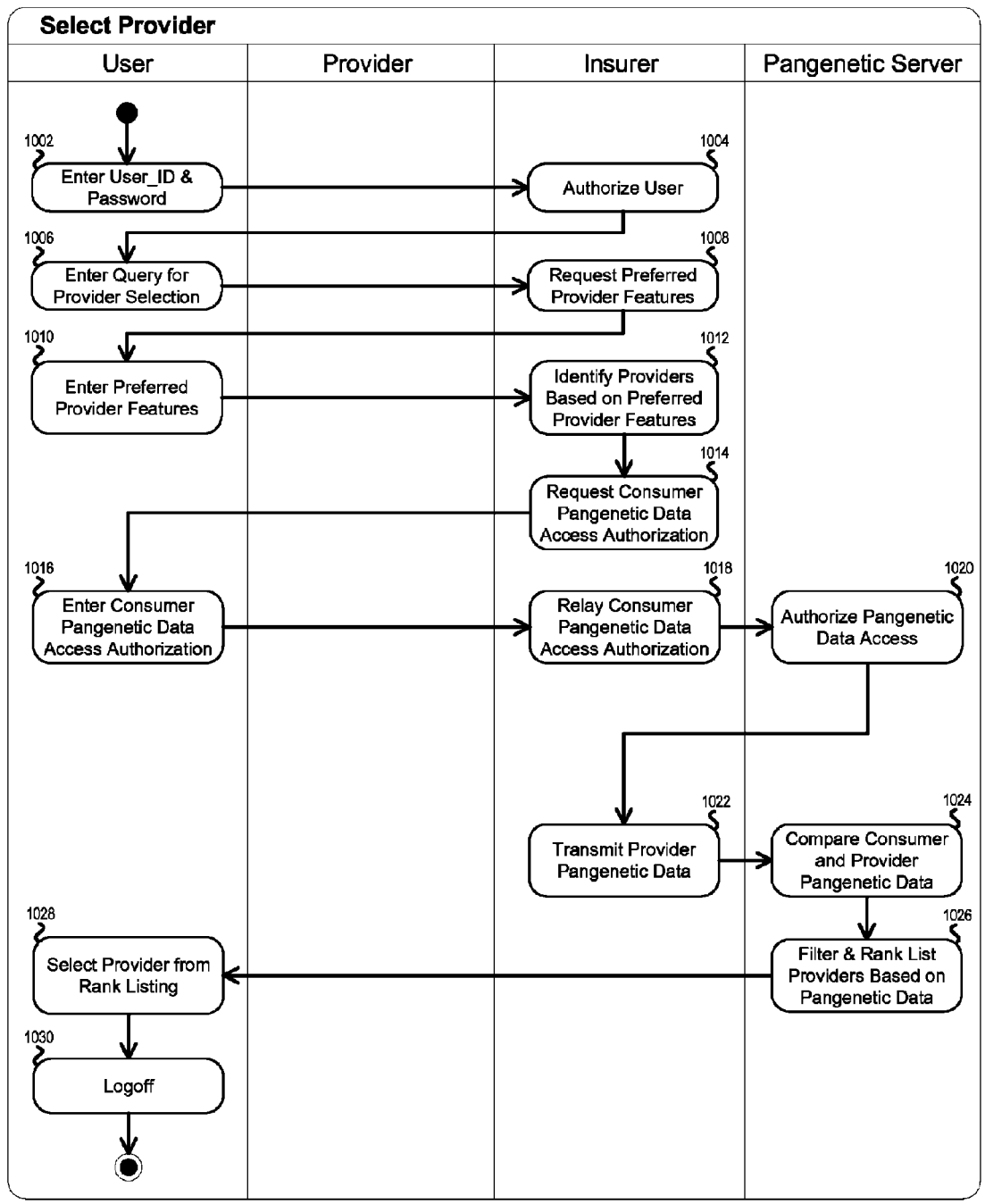
FIG. 10 illustrates a second activity diagram depicting pangenetic based selection of a provider.

FIG. 10 illustrates a UML activity diagram for another embodiment of service provider selection. In the particular embodiment of 'select provider' represented in this diagram, the pangenetic server hosts the portion of the pangenetic based selection system which performs comparisons between the pangenetic data of the consumer and candidate providers. In enter user_ID & password step 1002, a user such as a patient (i.e., consumer), healthcare professional, or insurer representative gains secure access to the system by logging on to the system with their secure personal login identifiers. This login information can alternatively be in the form of other secure login procedures such as retinal or fingerprint scan, or a personal identification card that is based on magnetic or RFID technology. In authorize user step 1004, the user logon information is verified and access is granted if the security information passes verification. In enter query for provider selection step 1006, the user enters a request for selection of one or more providers. In request preferred provider features step 1008, the system queries the user for desired features of the provider, particularly non-pangenetic features. For example, in enter preferred provider feature step 1010, the user can enter preferences for location, price bracket, specialty and gender of providers, for example. In a further embodiment, these preferences may be specified by the user to be inflexible requirements for selection of a provider, so that a provider must match these specified preferences in order to be a candidate for further pangenetic based selection. Alternatively, these preferences can be treated as flexible so that in circumstances when only a small number (or none) of the providers in the system database match all of the user's preferences, then providers that meet (or approximately meet) some of the preferences are also included to provide at least some viable choices for the user to select from. In identify providers based on preferred provider features step 1012, the system identifies (i.e., flags, stores or tabulates) candidate providers for the customer based on the user specified set of preferred provider features. As an example in the healthcare field, a user request for a female general practitioner located within a particular zip code invokes the system to identify candidate providers for the consumer that match the desired gender, subspecialty and location. The preference for specialty may be an inflexible requirement. However, flexibility can be incorporated with respect to the other preferred features. For example, if a request for a female general practitioner located in a specific zip code would return a null result, then the system may identify candidate providers comprising 1) male general practitioners located within the desired zip code, and 2) female general practitioners located within reasonably close proximity to the desired zip code. This example exemplifies how flexibility can be incorporated with respect to multiple desired features as when no providers meet all the preferred features or when a provider matches some of the features (e.g., specialty) but not others (e.g., gender and location). This step of identifying providers can include, for example, scoring, ranking or ordering the providers based on the preferred features (i.e., based on the extent to which the preferred features are possessed by each candidate provider). In a further embodiment, the user or system can be allowed to decide which preferred features are inflexible, which are flexible (and to what extent they are flexible, such as the maximum allowable distance of a provider from a desired zip code location), and which have priority in scoring, ranking and/or ordering of the results. It should be noted that the above step of identifying providers based on user specified preferred features precedes the following steps of pangenetic based comparison and selection, and can therefore serve as a preselection step if used to filter out providers from further consideration by the steps that follow. However, this step can also be relocated in the activity diagram sequence to follow the pangenetic based comparison and selection steps if, for example, the user, customer, providers, insurer or system deem pangenetic based selection to be the more important determinant for selection of the best provider for the customer.

In request consumer pangenetic data access authorization step 1014, the user is queried by the insurer's system to identify the consumer for whom the selection is intended as well as to provide authorization/permission to access that consumer's pangenetic information. In enter consumer pangenetic data access authorization step 1016, the user responds to the system's request for access to consumer pangenetic data by inputting an identifier of the consumer, access code and/or user_ID and password security information associated with the user or consumer in order to allow the system to access at least a portion of the pangenetic data associated with the particular consumer for whom a provider is being selected. In relay consumer pangenetic data access authorization step 1018, the insurer's system receives the identifier information and/or access authorization needed to access the pangenetic data of the consumer and passes at least a portion of that information along with a request for access to the relevant pangenetic data of the consumer to a pangenetic server (e.g., an EMR, EHR or PHR database server) where that pangenetic data is stored. In authorize pangenetic data access step 1020, the pangenetic server verifies the validity of the access request. This verification can include authenticating the insurer database server submitting the request to ensure the request is coming from a valid or pre-authorized entity. In transmit provider pangenetic data step 1022, the insurer system sends the pangenetic data associated with one or more providers to the pangenetic server (the provider associated pangenetic data having been previously correlated with one or more measures of success). In compare consumer and provider pangenetic data step 1024, the pangenetic based selection system compares the provider associated pangenetic data with the consumer associated pangenetic data contained on the pangenetic server. The comparison is designed to determine matches between features contained in the two sets of pangenetic data. Matching features can be defined as features that are identical between the two sets of data, or they can be defined somewhat more non-stringently as features that are equivalent between the two sets of data. Features that are equivalent can be those that are not identical, but have the same or essentially the same impact on an outcome, response or phenotype. In filter & rank-list providers based on pangenetic data step 1026, the system filters and ranks candidate providers based on the results of the pangenetic comparison and can transmit the providers as a list or tabulation. With respect to filtering the providers, if the consumer's pangenetic features are a poor match to those associated with a particular provider, then that provider can be eliminated (i.e., filtered out) during this step. Providers which match a considerable portion of pangenetic features of the consumer can be evaluated with respect to the degree of similarity (i.e., percent identity of the set of features) shared with the consumer and then scored, ranked and/or ordered relative to each other, for example. Matching between certain pangenetic features can be given greater weight for the purpose of scoring, ranking and/or ordering, for example in circumstances where certain pangenetic features are known to have greater influence on the customer's condition or needs, or the desired outcome. The list can indicate categories or types of pangenetic features that matched and to what degree, and can also indicate the values of non-pangenetic features for providers in the list and the extent of matching with the consumer's preferences with respect to those features. In one embodiment, the user can be provided with options to adjust parameters such as weighting and priority of features to influence the values for scores and ranks of the individual providers or the order of the providers as listed in the tabulation. In select provider from rank listing step 1028, the user selects one or more of the providers presented to them by the system based simply on rank or score, or based on a further evaluation of the type and extent of pangenetic and non-pangenetic features which matched between the consumer and each of the providers. While not shown in the embodiment represented in this activity diagram, a step linking the user to a provider scheduling/appointment page or a step requesting final approval of the user's selection can be included. In logoff step 1030, the user logs out to end the session and terminates secure access to the system. This logoff step can be automated based on closing the application or moving out of range of an optical sensor or RFID sensor which detects the presence of the authorized user to ensure that an unauthorized user does not inadvertently gain access the consumer's pangenetic data or pangenetic based results, thereby ensuring that strict doctor-patient privacy can be maintained in a healthcare setting, or ensuring in a public setting that others do not gain access to an individual's pangenetic data through an easily captured mobile device for example.

Figure 11:
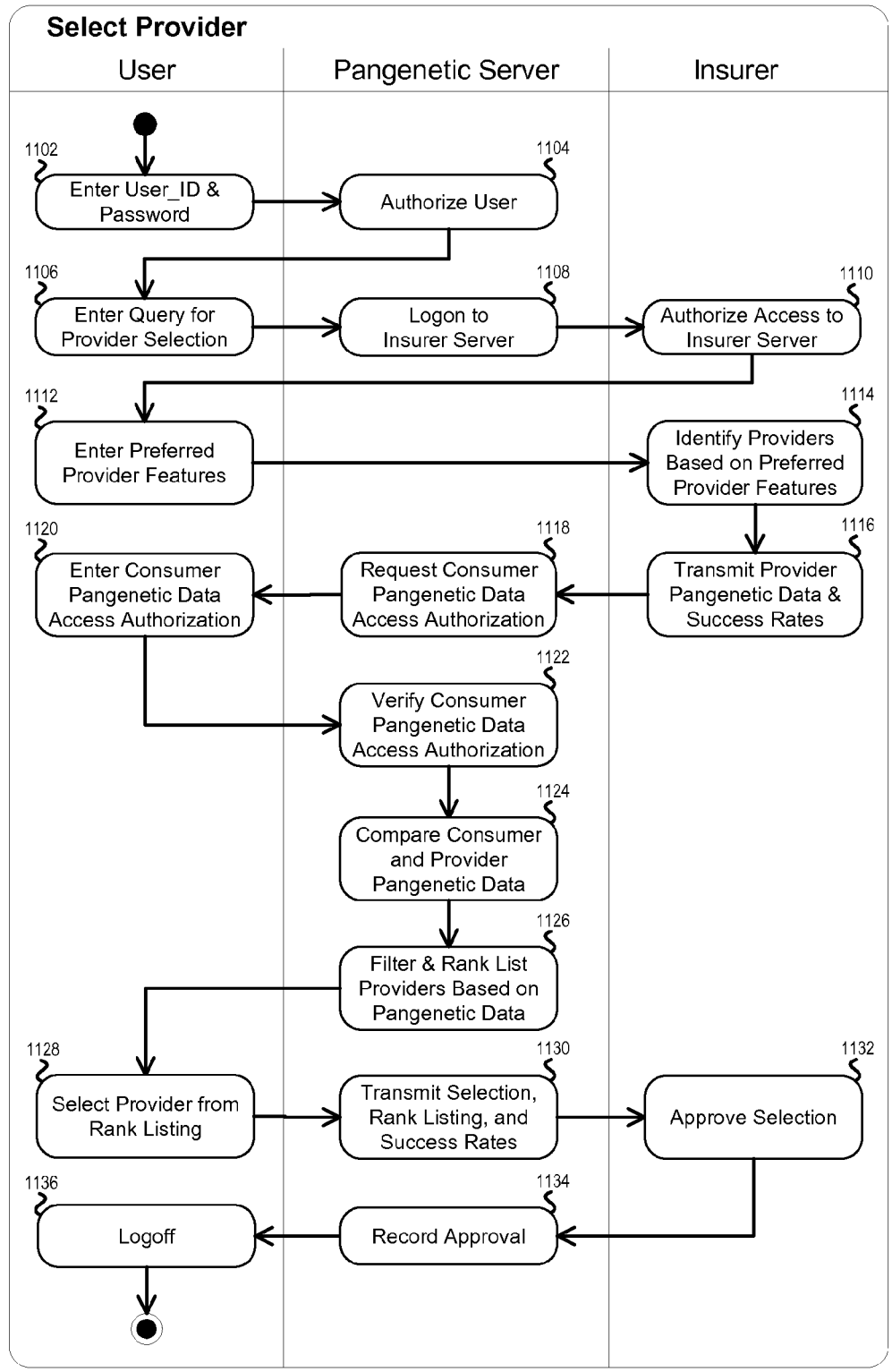
FIG. 11 illustrates a third activity diagram depicting pangenetic based selection of a provider.

FIG. 11 illustrates a UML activity diagram for another embodiment of service provider selection. In the particular embodiment of 'select provider' represented in this figure, the pangenetic server (e.g., an EMR, EHR or PHR database server) hosts the portion of the pangenetic based selection system which performs comparisons between the pangenetic data of the consumer and candidate providers. In enter user_ID & password step 1102, a user such as a patient (i.e., consumer), healthcare professional, or insurer representative gains secure access to the system by logging on to the system with their secure personal login identifiers. This login information can alternatively be in the form of other secure login procedures such as retinal or fingerprint scan, or a personal identification card that is based on magnetic or RFID technology. In authorize user step 1104, the user logon information is verified and access is granted if the security information passes verification. In enter query for provider selection step 1106, the user enters a request for selection of one or more providers. In logon to insurer account step 1108, the pangenetic server logs on to the insurer server and may pass information to the insurer regarding the user or consumer, such as their unique identifier or insurance plan number, so that data for the appropriate providers (i.e., in network providers covered by the consumer's particular insurance plan) will be accessed. In authorize access to insurer server step 1110, the insurer server verifies the authenticity of the pangenetic server and/or user attempting to gain access. In enter preferred provider features step 1112, the user can enter preferences for location, price bracket, specialty and gender of providers, for example. In a further embodiment, these preferences may be specified by the user to be inflexible requirements for selection of a provider, so that a provider must match these specified preferences in order to be a candidate for further pangenetic based selection. Alternatively, these preferences can be treated as flexible so that in circumstances when only a small number (or none) of the providers in the system database match all of the user's preferences, then providers that meet (or approximately meet) some of the preferences are also included to provide at least some viable choices for the user to select from. In identify providers based on preferred provider features step 1114, the system identifies (i.e., flags, stores or tabulates) candidate providers for the customer based on the user specified set of preferred provider features. As an example in the healthcare field, a user request for a female general practitioner located within a particular zip code invokes the system to identify candidate providers for the consumer that match the desired gender, subspecialty and location. The preference for specialty may be an inflexible requirement. However, flexibility can be incorporated with respect to the other preferred features. For example, if a request for a female general practitioner located in a specific zip code would return a null result, then the system may identify candidate providers comprising 1) male general practitioners located within the desired zip code, and 2) female general practitioners located within reasonably close proximity to the desired zip code. This example exemplifies how flexibility can be incorporated with respect to multiple desired features as when no providers meet all the preferred features or when a provider matches some of the features (e.g., specialty) but not others (e.g., gender and location). This step of identifying providers can include, for example, scoring, ranking or ordering the providers based on the preferred features (i.e., based on the extent to which the preferred features are possessed by each candidate provider). In a further embodiment, the user or system can be allowed to decide which preferred features are inflexible, which are flexible (and to what extent they are flexible, such as the maximum allowable distance of a provider from a desired zip code location), and which have priority in scoring, ranking and/or ordering of the results. It should be noted that the above step of identifying providers based on user specified preferred features precedes the following steps of pangenetic based comparison and selection, and can therefore serve as a pre-selection step if used to filter out providers from further consideration by the steps that follow. However, this step can also be relocated in the activity diagram sequence to follow the pangenetic based comparison and selection steps if, for example, the user, customer, providers, insurer or system deem pangenetic based selection to be the more important determinant for selection of the best provider for the customer. In transmit provider pangenetic data and success rates step 1116, pangenetic data and one or more measures of success correlated with the pangenetic data are sent to the pangenetic server for those providers that were identified in step 1114. In another embodiment, the pangenetic data and measures of success can be contained (i.e., previously stored) on the pangenetic server, thereby eliminating the need for the insurer server to execute steps 1114 and 1116 and having the pangenetic server perform those steps instead.

In request consumer pangenetic data access authorization step 1118, the user is queried by the insurer's system to identify the consumer for whom the selection is intended as well as to provide authorization/permission to access that consumer's pangenetic information. In enter consumer pangenetic data access authorization step 1120, the user responds to the system's request for access to consumer pangenetic data by inputting information such as a customer identifier, access code and/or access authorization (e.g., user_ID and password) necessary to allow the system to access pangenetic data of the consumer. In verify consumer pangenetic data access authorization step 1122, the pangenetic server authenticates the user based on the information they provided. In compare consumer and provider pangenetic data step 1124, the pangenetic based selection system compares provider associated pangenetic data contained in a database of the system (the provider associated pangenetic data having been previously correlated with one or more measures of success) with the consumer associated pangenetic data that was provided by the pangenetic server. The comparison is designed to determine matches between features contained in the two sets of pangenetic data. Matching features can be defined as features that are identical between the two sets of data, or they can be defined somewhat more non-stringently as features that are equivalent between the two sets of data. Features that are equivalent can be those that are not identical, but have the same or essentially the same impact on an outcome, response or phenotype. In filter & rank-list providers based on pangenetic data step 1126, the system filters and ranks candidate providers based on the results of the pangenetic comparison and can transmit the providers as a list or tabulation. With respect to filtering the providers, if the consumer's pangenetic features are a poor match to those associated with a particular provider, then that provider can be eliminated (i.e., filtered out) during this step. Providers which match a considerable portion of pangenetic features of the consumer can be evaluated with respect to the degree of similarity (i.e., percent identity of the set of features) shared with the consumer and then scored, ranked and/or ordered relative to each other, for example. Matching between certain pangenetic features can be given greater weight for the purpose of scoring, ranking and/or ordering, for example in circumstances where certain pangenetic features are known to have greater influence on the customer's condition or needs, or the desired outcome. The list can indicate categories or types of pangenetic features that matched and to what degree, and can also indicate the values of non-pangenetic features for providers in the list and the extent of matching with the consumer's preferences with respect to those features. In one embodiment, the user can be provided with options to adjust parameters such as weighting and priority of features to influence the values for scores and ranks of the individual providers or the order of the providers as listed in the tabulation. In select provider from rank listing step 1128, the user selects one or more of the providers presented to them by the system based simply on rank or score, or based on a further evaluation of the type and extent of pangenetic and non-pangenetic features which matched between the consumer and each of the providers. In another embodiment, the user can allow the system to make an automated selection of one or more providers from the list (e.g., automated selection of the highest ranking or scoring provider). In transmit selection, rank listing, and success rates step 1130, the one or more providers selected by the user (or alternatively the system), along with the scores or ranks of the providers and the success rates associated with the degree of pangenetic match of each provider with the consumer, are transmitted to the insurer for approval. In approve selection step 1132, the insurer server can approve (or alternatively reject) one or more of the selected providers. In record approval step 1134, the pangenetic server can save and/or transmit the insurer's approval (or rejection/denial) of providers to the user. In logoff step 1136, the user logs out to end the session and terminates secure access to the system. This logoff step can be automated based on closing the application or moving out of range of an optical sensor or RFID sensor which detects the presence of the authorized user to ensure that an unauthorized user does not inadvertently gain access the consumer's pangenetic data or pangenetic based results, thereby ensuring that strict doctor-patient privacy can be maintained in a healthcare setting, or ensuring in a public setting that others do not gain access to an individual's pangenetic data through an easily captured mobile device for example.

Figure 12:
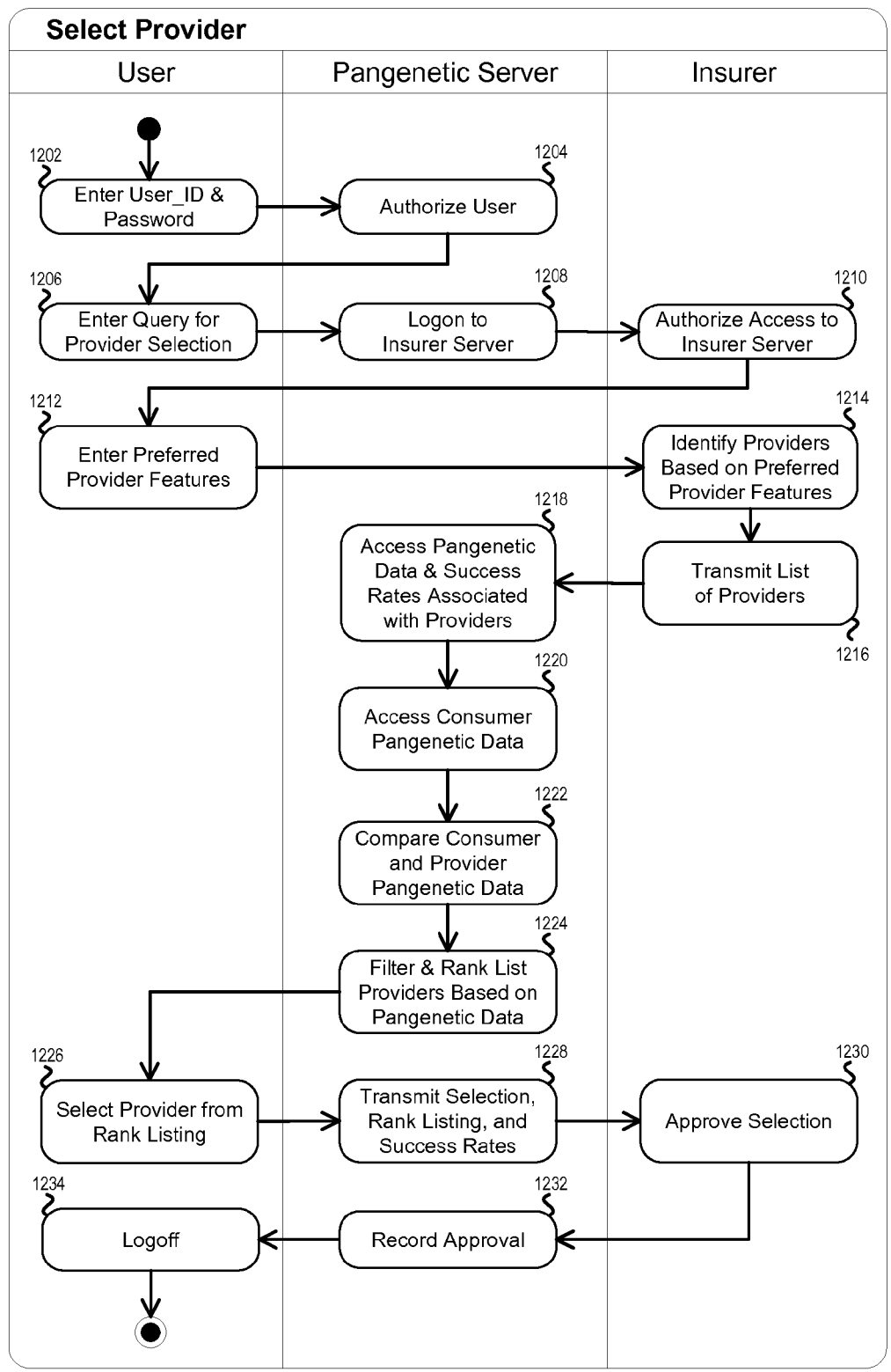
FIG. 12 illustrates a fourth activity diagram depicting pangenetic based selection of a provider.

FIG. 12 illustrates a UML activity diagram for another embodiment of service provider selection. In the particular embodiment of 'select provider' represented in this figure, the pangenetic server (e.g., an EMR, EHR or PHR database server) hosts the portion of the pangenetic based selection system which performs comparisons between the pangenetic data of the consumer and candidate providers. In enter user_ID & password step 1202, a user such as a patient (i.e., consumer), healthcare professional, or insurer representative gains secure access to the system by logging on to the system with their secure personal login identifiers. This login information can alternatively be in the form of other secure login procedures such as retinal or fingerprint scan, or a personal identification card that is based on magnetic or RFID technology. In authorize user step 1204, the user logon information is verified and access is granted if the security information passes verification. In enter query for provider selection step 1206, the user enters a request for selection of one or more providers. In logon to insurer account step 1208, the pangenetic server logs on to the insurer server and may pass information to the insurer regarding the user or consumer, such as their unique identifier or insurance plan number, so that data for the appropriate providers (i.e., in network providers covered by the consumer's particular insurance plan) will be accessed. In authorize access to insurer server step 1210, the insurer server verifies the authenticity of the pangenetic server and/or user attempting to gain access. In enter preferred provider features step 1212, the user can enter preferences for location, price bracket, specialty and gender of providers, for example. In a further embodiment, these preferences may be specified by the user to be inflexible requirements for selection of a provider, so that a provider must match these specified preferences in order to be a candidate for further pangenetic based selection. Alternatively, these preferences can be treated as flexible so that in circumstances when only a small number (or none) of the providers in the system database match all of the user's preferences, then providers that meet (or approximately meet) some of the preferences are also included to provide at least some viable choices for the user to select from. In identify providers based on preferred provider features step 1214, the system identifies (i.e., flags, stores or tabulates) candidate providers for the customer based on the user specified set of preferred provider features. As an example in the healthcare field, a user request for a female general practitioner located within a particular zip code invokes the system to identify candidate providers for the consumer that match the desired gender, subspecialty and location. The preference for specialty may be an inflexible requirement. However, flexibility can be incorporated with respect to the other preferred features. For example, if a request for a female general practitioner located in a specific zip code would return a null result, then the system may identify candidate providers comprising 1) male general practitioners located within the desired zip code, and 2) female general practitioners located within reasonably close proximity to the desired zip code. This example exemplifies how flexibility can be incorporated with respect to multiple desired features as when no providers meet all the preferred features or when a provider matches some of the features (e.g., specialty) but not others (e.g., gender and location). This step of identifying providers can include, for example, scoring, ranking or ordering the providers based on the preferred features (i.e., based on the extent to which the preferred features are possessed by each candidate provider). In a further embodiment, the user or system can be allowed to decide which preferred features are inflexible, which are flexible (and to what extent they are flexible, such as the maximum allowable distance of a provider from a desired zip code location), and which have priority in scoring, ranking and/or ordering of the results. It should be noted that the above step of identifying providers based on user specified preferred features precedes the following steps of pangenetic based comparison and selection, and can therefore serve as a pre-selection step if used to filter out providers from further consideration by the steps that follow. However, this step can also be relocated in the activity diagram sequence to follow the pangenetic based comparison and selection steps if, for example, the user, customer, providers, insurer or system deem pangenetic based selection to be the more important determinant for selection of the best provider for the customer. In transmit list of providers step 1216, the one or more providers that were identified in step 1214 are transmitted to the pangenetic server for further evaluation based on pangenetic features. In another embodiment, non-pangenetic provider information can be contained (i.e., previously stored) on the pangenetic server, thereby eliminating the need for the insurer server to execute steps 1214 and 1216 and having the pangenetic server perform those steps instead.

In access pangenetic data and success rates associated with providers step 1218, the pangenetic server accesses provider associated pangenetic information and one or more correlated measures of success contained in a database of the pangenetic server. In access consumer pangenetic data step 1220, the system accesses pangenetic data associated with the consumer, for example at least a portion of a pangenetic profile of the consumer. In compare consumer and provider pangenetic data step 1222, the pangenetic based selection system compares provider associated pangenetic data contained in the pangenetic database with the consumer associated pangenetic data. The comparison is designed to determine matches between features contained in the two sets of pangenetic data. Matching features can be defined as features that are identical between the two sets of data, or they can be defined somewhat more non-stringently as features that are equivalent between the two sets of data. Features that are equivalent can be those that are not identical, but have the same or essentially the same impact on an outcome, response or phenotype. In filter & rank-list providers based on pangenetic data step 1224, the system filters and ranks candidate providers based on the results of the pangenetic comparison and can transmit the providers as a list or tabulation. With respect to filtering the providers, if the consumer's pangenetic features are a poor match to those associated with a particular provider, then that provider can be eliminated (i.e., filtered out) during this step. Providers which match a considerable portion of pangenetic features of the consumer can be evaluated with respect to the degree of similarity (i.e., percent identity of the set of features) shared with the consumer and then scored, ranked and/or ordered relative to each other, for example. Matching between certain pangenetic features can be given greater weight for the purpose of scoring, ranking and/or ordering, for example in circumstances where certain pangenetic features are known to have greater influence on the customer's condition or needs, or the desired outcome. The list can indicate categories or types of pangenetic features that matched and to what degree, and can also indicate the values of non-pangenetic features for providers in the list and the extent of matching with the consumer's preferences with respect to those features. In one embodiment, the user can be provided with options to adjust parameters such as weighting and priority of features to influence the values for scores and ranks of the individual providers or the order of the providers as listed in the tabulation. In select provider from rank listing step 1226, the user selects one or more of the providers presented to them by the system based simply on rank or score, or based on a further evaluation of the type and extent of pangenetic and non-pangenetic features which matched between the consumer and each of the providers. In another embodiment, the user can allow the system to make an automated selection of one or more providers from the list (e.g., automated selection of the highest ranking or scoring provider). In transmit selection, rank listing, and success rates step 1228, the one or more providers selected by the user (or alternatively the system), along with the scores or ranks of the providers and the success rates associated with the degree of pangenetic match of each provider with the consumer, are transmitted to the insurer for approval. In approve selection step 1230, the insurer server can approve (or alternatively reject) one or more of the selected providers. In record approval step 1232, the pangenetic server can save and/or transmit the insurer's approval (or rejection/denial) of providers to the user. In logoff step 1234, the user logs out to end the session and terminates secure access to the system. This logoff step can be automated based on closing the application or moving out of range of an optical sensor or RFID sensor which detects the presence of the authorized user to ensure that an unauthorized user does not inadvertently gain access the consumer's pangenetic data or pangenetic based results, thereby ensuring that strict doctor-patient privacy can be maintained in a healthcare setting, or ensuring in a public setting that others do not gain access to an individual's pangenetic data through an easily captured mobile device for example.

The embodiments of provider selection represented in FIGS. 9-12 can be adapted with minor modification for selection of products, services and establishments. As mentioned previously, establishments can be considered, in one or more embodiments to be service providers, and therefore the embodiments represented in FIGS. 9-12 can be directly interpreted for selecting establishments. An example of how the method steps of FIG. 12 can be easily adapted for the selection of services is exemplified by FIG. 13, and can be similarly accomplished for the methods illustrated in FIGS. 9-11.

Figure 13:
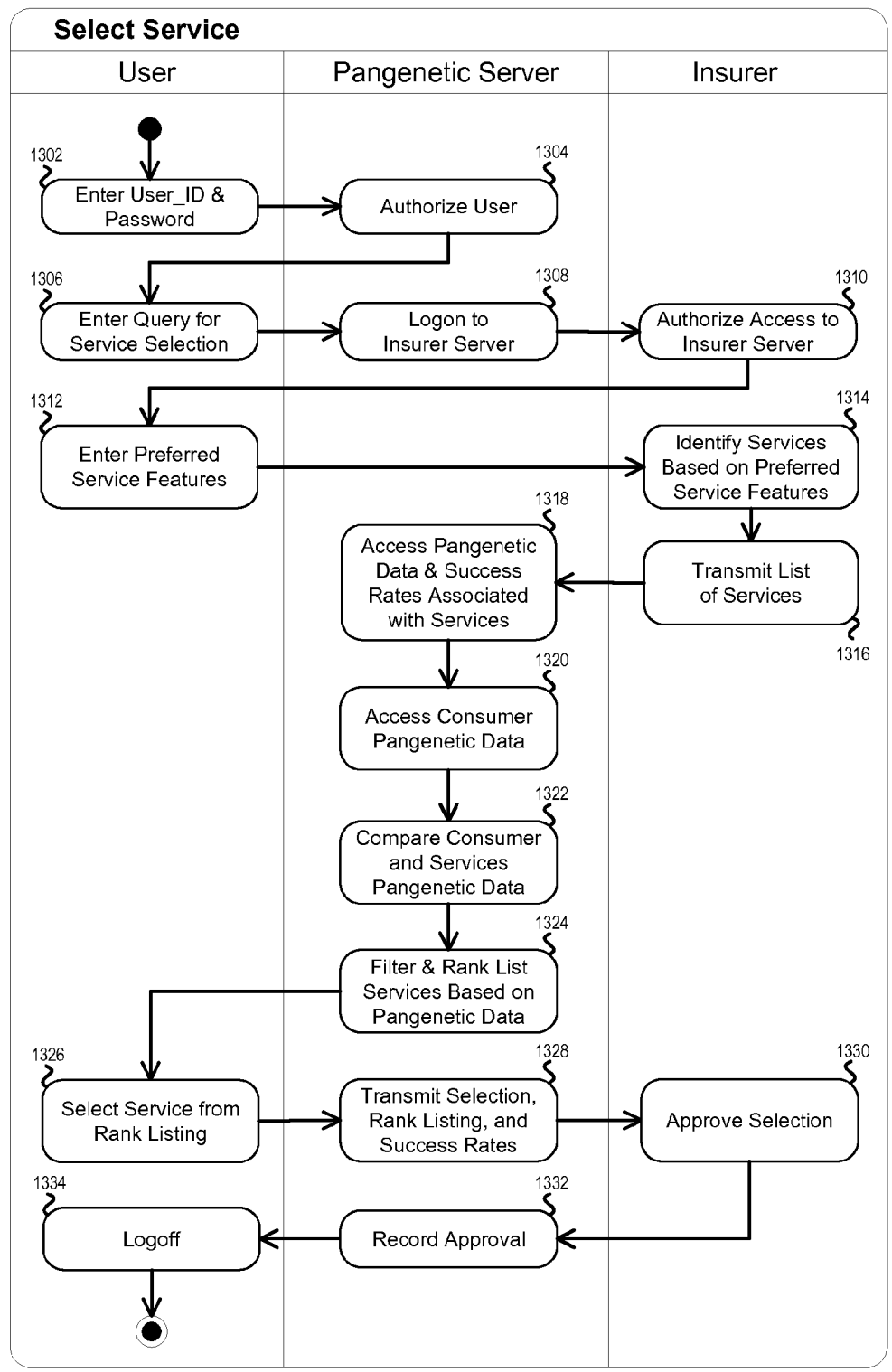
FIG. 13 illustrates an activity diagram depicting pangenetic based selection of a service.

FIG. 13 illustrates a UML activity diagram for one embodiment of service selection. In the particular embodiment of 'select service' represented in this figure, the pangenetic server (e.g., an EMR, EHR or PHR database server) hosts the portion of the pangenetic based selection system which performs comparisons between the pangenetic data of the consumer and candidate services. In enter user_ID & password step 1302, a user such as a patient (i.e., consumer), healthcare professional, or insurer representative gains secure access to the system by logging on to the system with their secure personal login identifiers. This login information can alternatively be in the form of other secure login procedures such as retinal or fingerprint scan, or a personal identification card that is based on magnetic or RFID technology. In authorize user step 1304, the user logon information is verified and access is granted if the security information passes verification. In enter query for service selection step 1306, the user enters a request for selection of one or more services. In logon to insurer server step 1308, the pangenetic server logs on to the insurer server and may pass information to the insurer regarding the user or consumer, such as their unique identifier or insurance plan number, so that data for the appropriate services (i.e., services covered by the consumer's particular insurance plan) will be accessed. In authorize access to insurer server step 1310, the insurer server verifies the authenticity of the pangenetic server and/or user attempting to gain access. In enter preferred provider features step 1312, the user can enter preferences for category/type, brand, and price range of products, for example. In a further embodiment, these preferences may be specified by the user to be inflexible requirements for selection of a service, so that a service must match these specified preferences in order to be a candidate for further pangenetic based selection. Alternatively, these preferences can be treated as flexible so that in circumstances when only a small number (or none) of the services in the system database match all of the user's preferences, then services that meet (or approximately meet) some of the preferences are also included to provide at least some viable choices for the user to select from. In identify services based on preferred service features step 1314, the system identifies (i.e., flags, stores or tabulates) candidate services for the customer based on the user specified set of preferred service features. This step of identifying services can include, for example, scoring, ranking or ordering the services based on the preferred features (i.e., based on the extent to which the preferred features are possessed by each candidate service). In a further embodiment, the user or system can be allowed to decide which preferred features are inflexible, which are flexible, and which have priority in scoring, ranking and/or ordering of the results. It should be noted that the above step of identifying services based on user specified preferred features precedes the following steps of pangenetic based comparison and selection, and can therefore serve as a preselection step if used to filter out services from further consideration by the steps that follow. However, this step can also be relocated in the activity diagram sequence to follow the pangenetic based comparison and selection steps if, for example, the user, customer, services, insurer or system deem pangenetic based selection to be the more important determinant for selection of the best service for the customer. In transmit service list step 1316, the one or more services that were identified in step 1314 are transmitted to the pangenetic server for further evaluation based on pangenetic features. In another embodiment, non-pangenetic service information can be contained (i.e., previously stored) on the pangenetic server, thereby eliminating the need for the insurer server to execute steps 1314 and 1316 and having the pangenetic server perform those steps instead.

In access pangenetic data and success rates associated with services step 1318, the pangenetic server accesses service associated pangenetic information and one or more correlated measures of success contained in a database of the pangenetic server. In access consumer pangenetic data step 1320, the system accesses pangenetic data associated with the consumer, for example at least a portion of a pangenetic profile of the consumer. In compare consumer and service pangenetic data step 1322, the pangenetic based selection system compares service associated pangenetic data contained in the pangenetic database with the consumer associated pangenetic data. The comparison is designed to determine matches between features contained in the two sets of pangenetic data. Matching features can be defined as features that are identical between the two sets of data, or they can be defined somewhat more non-stringently as features that are equivalent between the two sets of data. Features that are equivalent can be those that are not identical, but have the same or essentially the same impact on an outcome, response or phenotype. In filter & rank-list services based on pangenetic data step 1324, the system filters and ranks candidate services based on the results of the pangenetic comparison and can transmit the services as a list or tabulation. With respect to filtering the services, if the consumer's pangenetic features are a poor match to those associated with a particular service, then that service can be eliminated (i.e., filtered out) during this step. Services which match a considerable portion of pangenetic features of the consumer can be evaluated with respect to the degree of similarity (i.e., percent identity of the set of features) shared with the consumer and then scored, ranked and/or ordered relative to each other, for example. Matching between certain pangenetic features can be given greater weight for the purpose of scoring, ranking and/or ordering, for example in circumstances where certain pangenetic features are known to have greater influence on the customer's condition or needs, or the desired outcome. The list can indicate categories or types of pangenetic features that matched and to what degree, and can also indicate the values of non-pangenetic features for services in the list and the extent of matching with the consumer's preferences with respect to those features. In one embodiment, the user can be provided with options to adjust parameters such as weighting and priority of features to influence the values for scores and ranks of the individual services or the order of the services as listed in the tabulation. In select service from rank listing step 1326, the user selects one or more of the services presented to them by the system based simply on rank or score, or based on a further evaluation of the type and extent of pangenetic and non-pangenetic features which matched between the consumer and each of the services. In another embodiment, the user can allow the system to make an automated selection of one or more services from the list (e.g., automated selection of the highest ranking or scoring service). In transmit selection, rank listing, and success rates step 1328, the one or more services selected by the user (or alternatively the system), along with the scores or ranks of the services and the success rates associated with the degree of pangenetic match of each service with the consumer, are transmitted to the insurer for approval. In approve selection step 1330, the insurer server can approve (or alternatively reject) one or more of the selected services. In record approval step 1332, the pangenetic server can save and/or transmit the insurer's approval (or rejection/denial) of services to the user. In logoff step 1334, the user logs out to end the session and terminates secure access to the system. This logoff step can be automated based on closing the application or moving out of range of an optical sensor or RFID sensor which detects the presence of the authorized user to ensure that an unauthorized user does not inadvertently gain access the consumer's pangenetic data or pangenetic based results, thereby ensuring that strict doctor-patient privacy can be maintained in a healthcare setting, or ensuring in a public setting that others do not gain access to an individual's pangenetic data through an easily captured mobile device for example.

In one embodiment of a computer based method for selecting a product, service, provider, or establishment, the system can access pangenetic data and outcome data associated with a plurality of consumers that received products and services, or interacted with service providers and establishments (service providers can be establishments). The identities of the consumers can be masked or anonymized for privacy or security purposes. The service provider can be a healthcare provider, a non-healthcare provider, a medical provider, a non-medical provider, a clinical provider, and a non-clinical provider.

Initially, the system can receive a request for a product, service or provider for a consumer. This request can originate from the consumer, a provider, or another type of user such as an insurer or claim adjuster. The system can then transmit a request for access to pangenetic data associated with the consumer. This request can be met with a variety of possible security/authorization procedures and inputs which then result in the system receiving access to the pangenetic data associated with the consumer. The pangenetic data may be contained in a single dataset or database (as with a single EHR, EMR or PHR containing pangenetic data), or it may be contained across multiple datasets or databases. The pangenetic data can be, for example, SNPs, nucleotides, base pairs, nucleotide sequences, gene sequences, genomic sequences, gene mutations, epigenetic modifications, epigenetic sequence patterns, and pangenetic based disorders, traits and conditions.

After receiving access to the pangenetic data associated with the consumer, the system can then proceed to determine the strength of correlation between the pangenetic data associated with the consumer and pangenetic based profiles corresponding to (i.e., associated with) products, services or providers. The determination of these correlations can be achieved by comparing the pangenetic data associated with the consumer with the pangenetic profiles associated with the products, services or providers and then employing statistical measures known to those of skill in the art to compute the values for pangenetic based statistical correlations between the consumer and the products, services or providers. The results of these statistical measures can provide an indication of the strength (degree) of the correlations as well as the statistical significance (confidence) of the correlations. Examples of statistical measures that provide values indicating the strength of correlations include probability, likelihood (odds), likelihood ratio (odds ratio), absolute risk and relative risk. Examples of statistical measures that provide values indicating statistical significance of correlations include standard deviation, standard error, confidence intervals, and p values. As mentioned previously, there are algorithms know to those of skill in the art for identifying large patterns of genetic and epigenetic features shared between individuals, after which statistical measures can be applied to determine correlation with outcomes. The determination of shared features requires determining the equivalence between features at the level of individual features and/or at the level of sub-combinations of features. The determination of equivalence between pangenetic shared features can be inflexible and require features to be identical, or it can be flexible and allow features to be non-identical if it is known that the difference between two non-identical pangenetic features or pangenetic feature subcombinations does not significantly affect an outcome such as a particular phenotype (e.g., trait, response) or success level. For example, pangenetic data can be identified as being equivalent if the pangenetic data are epigenetic or genetic variations that are silent with respect to their effect on outcome or phenotype (e.g., gene sequences which differ by one or more silent nucleotide substitutions, mutations, or polymorphisms). Pangenetic data can also be identified as being equivalent if the pangenetic data are conservative genetic variations (e.g., conservative nucleotide substitutions, mutations, or polymorphisms occurring within the protein encoding 'open reading frame' of a gene sequence) that have no effect on the outcome or phenotype of interest. Pangenetic data can also be identified as being equivalent if the pangenetic data are non-conservative genetic variations (e.g., non-conservative nucleotide substitutions, mutations, or polymorphisms) that have the same effect on the outcome (e.g., phenotype) of interest. The above variations may occur within one or more gene coding regions or they may occur outside of gene coding regions (e.g., in noncoding 'junk DNA' regions of the genome). In determining the correlation, greater weight can be given for pangenetic feature matches (i.e., matches between certain types of pangenetic features) that are known to have a stronger association with the product, service or provider and/or the level of success desired.

The pangenetic based profiles can contain at least one measure of success corresponding to pangenetic data contained within the pangenetic profile that are correlated with corresponding products, services or providers. The measures of success can be used to determine the most appropriate product, service or provider for the consumer in circumstances when the consumer is a reasonably strong pangenetic match to a plurality of pangenetic profiles corresponding to several products, services or providers.

Next, the system can transmit an indication that the service provider is appropriate (a match, recommended) for the consumer if the result of the correlation exceeds a predetermined threshold. The predetermined threshold can be determined by the system, or it can be specified by a user, for example. The system can automatically chose, or be user directed, to transmit the output to at least one destination—a user, a database, a dataset, a computer readable memory, a computer readable medium, a computer processor, a computer network, a printout device, a visual display, and a wireless receiver—for the purpose of display, storage, or further processing and evaluation. An indication that the product, service or provider is appropriate for the consumer can, in one embodiment, constitute an insurer based approval of the product, service or provider for the consumer. An indication that a particular service provider is appropriate for the consumer can, in another embodiment, can constitute or be used to generate an approval for rendering payment to that service provider.

In a further embodiment, the method can be repeated for a plurality of products, services or providers, and the results can be transmitted as a tabulation of products, services or providers determined to be appropriate for the consumer. In a further embodiment, ranking of the products, services or providers in the tabulation can be performed to generate a rank listing of the service providers determined to be appropriate for the consumer, wherein the rank of each of the service providers in the ranked listing can be based on the magnitude of the correlations, and if available, can also be based on the values of measures of success associated with each of the products, service or providers with respect to a particular desired outcome or phenotype of interest. A rank listing can enable a user, consumer or insurer, for example, to choose (or approve) the best product, service or provider for the consumer from several appropriate choices.

In a further embodiment of the method and system, the recommendation of a service provider for a consumer can be used by the pangenetic based system or another system to generate an approval for rendering payment to the service provider. In addition to being used to generate a payment approval, the indicated recommendation can also be used to generate a payment approval request, or to generate a financial transaction or insurance claim.

In another embodiment of the method and system, non-pangenetic data such as non-pangenetic features of the consumer, and/or non-pangenetic features that the consumer or user want the product, service or provider to possess, can be included in the selection process. In one embodiment for example, non-pangenetic features can be used in pre-selection steps to narrow down (filter) the candidate list of products, services or providers that are to be processed by pangenetic based selection, in post-selection steps to filter and refine the results produced by pangenetic based selection, and in steps simultaneous with pangenetic selection to influence the determination of strength of correlations between pangenetic based profiles and the ranking, scoring and/or ordering of the selected products, services or providers.

An embodiment of a computer database system for selecting a product, service or provider can comprise a memory having a first data structure containing pangenetic data associated with the consumer and a second data structure containing a pangenetic based profile corresponding to a service provider. The computer database system can further comprise a processor for receiving a request for a service provider for a consumer; transmitting a request for access to the pangenetic data associated with the consumer that is contained in the first data structure; receiving access to the pangenetic data; correlating the pangenetic data with the pangenetic based profile that is contained in the second data structure; and transmitting an indication that the service provider is appropriate (a match, recommended) for the consumer if the result of the correlation exceeds a predetermined threshold.

In one or more embodiments, data masks can be used to block access, reading and/or transmission of at least a portion of the data (i.e., data profile) associated with one or more consumers. Any type of pangenetic (genetic and epigenetic) and non-pangenetic data can potentially be masked using data masks. Pangenetic data that can be masked includes, but is not limited to, individual features such as nucleotide identities contained in full or partial genomic sequence, SNP identities contained in genome scans, individual epigenetic modifications, epigenetic patterns (i.e., motifs), genetic or epigenetic regulated gene expression patterns (which can be tissue specific), individual genetic mutations, genetic mutation rates, telomere length (a marker of age and the rate of senescence), and occurrences of genome integrated viruses and virus sequences (such as occurrences of integration of HIV virus into the human genome).

A consumer may want portions of their pangenetic data to be masked from (i.e., inaccessible to) an insurer, such as particular genetic sequences or epigenetic patterns that reveal the consumer's present health conditions, their susceptibilities toward acquiring particular diseases in the future (i.e., disease predispositions), or their predicted lifespan (i.e., longevity predisposition). The consumer may want to keep the majority of their pangenetic information private from the insurer and only permit access to the minimum amount of pangenetic data necessary for the insurer to approve coverage of a selected product or service, or to process an insurance claim. At the same time, the consumer may want these portions of their pangenetic data to be unmasked (i.e., non-masked and accessible) to their physician so that the physician can perform a comprehensive diagnosis and treatment selection, for example. To enable both individualized and application dependent control of pangenetic data access, one or more data masks (i.e., pangenetic data masks, non-pangenetic data masks) can be used to control access, reading and/or transmission of certain data features as specified by the consumer, or as specified by a user (e.g., a physician) on behalf of the consumer. In one embodiment, one or more data masks can be associated with (i.e., linked to) one or more sets of data or a data profile (i.e., a pangenetic profile or a non-pangenetic profile) associated with the consumer. The data masks can be further linked to identifiers of particular individuals and organizations, so that when those individuals and organizations attempt to acquire the consumer's data, the appropriate mask will be applied to ensure access or transmission of only those portions of the consumer's data for which permission is granted with respect to those individuals and organizations. In another embodiment, data masks can be stored in association with identifiers of particular products, services and providers and applied to the data of consumers when generating pangenetic profiles for those products, services or providers, or when making pangenetic based selections of those entities for the consumer, without regard to the particular individual or organization that is accessing the consumers' data to accomplish those tasks. Pangenetic data masks that are associated with products, services and providers can provide the added benefit of increasing processing efficiency of profiling and selection methods by streamlining access and/or reading of consumer data features to only the designated portions of their data considered relevant to the profiling or selection of those particular products, services and providers. In one embodiment, a data mask associated with a consumer or user and a data mask associated with a product, service, or provider can be applied simultaneously when accessing a consumer's data profile (i.e., one or more data records).

In one or more embodiments, a consensus mask (consensus data mask) can be generated from two or more data masks and used to limit access to a portion of the data represented by the intersection between those two or more data masks. In one embodiment, the consensus mask can be a data mask representing a consensus between a plurality of data masks with respect to which data should be unmasked. In another embodiment, a consensus mask can be a data mask that represents a set of features (i.e., feature positions or identifiers, data record positions or identifiers) that a plurality of data masks all agree are permissible for access, reading and/or transmission. In the embodiment disclosed above which describes the simultaneous application of two or more data masks—at least one data mask associated with a consumer or user and at least one data mask associated with one or more products, services or providers—a consensus mask can be generated from the intersection of those two or more data masks and applied when accessing and/or transmitting the consumer's data, effectively achieving the same result as the simultaneous application of the two or more separate data masks. In one embodiment, the simultaneous application of two of more data masks comprises the generation and application of a consensus mask. A consensus data mask can be applied to the pangenetic and non-pangenetic profiles of an individual consumer during the selection of products, services and providers for that consumer.

A consensus mask can also be generated and used in circumstances of pangenetic profiling where, for example, two or more consumers have chosen to make at least a portion of their pangenetic data inaccessible using pangenetic data masks, but those pangenetic masks differ from each other. A consensus mask can be generated from the intersection of the differing data masks and then applied to the data profiles of all of the consumers being considered in that particular instance. With respect to pangenetic data for example, this ensures that the same set of pangenetic features, a minimal shared set of features, will be accessed for all of the pangenetic profiles associated with a group of consumers. So, by generating and using a consensus mask with respect to a group of consumers, inadvertent access to confidential pangenetic data can be prevented for the entire group while at the same time ensuring uniform access to exactly the same pangenetic features within each of the consumer's pangenetic profiles, thereby providing consistent and valid results when determining statistical associations, as may be required when generating pangenetic based profiles of products, services or providers, for example.

FIG. 14 illustrates abstract representations of data masks, more specifically three data masks labeled as data masks #1, #2 and #3 and one consensus mask that was generated from those three data masks. Within each of the masks, the 'M' character represents a mask feature indicator which indicates that the corresponding feature is masked and therefore inaccessible for reading or transmission. Within each of the masks, each 'U' character represents an unmask feature indicator which indicates that the corresponding feature is unmasked and therefore accessible for reading or transmission. With respect to masking of pangenetic data, each 'M' and 'U' character that is illustrated can correspond to a pangenetic data feature constituting an individual nucleotide, a SNP, a string of nucleotides (i.e., a nucleotide sequence), one or more partial or complete genes, an epigenetic nucleotide modification, or one or more partial or complete epigenetic patterns, for example. With respect to masking of non-pangenetic data, each 'M' and 'U' character that is illustrated can correspond to a variety of non-pangenetic features or combinations of non-pangenetic features.

Referring again to FIG. 14, the consensus data mask can be generated by at least two approaches. In an embodiment of a first approach, which is based on determining the intersection of unmasked features of a set of data masks, every unmasked feature position that is common to all the data masks is compiled into a singular collective mask in which the remaining positions are designated as masked feature positions by default, thereby creating the consensus mask. In an embodiment of a second approach, which is based on determining the union of masked features of a set of data masks, masked feature positions that are present in at least one of the data masks are consolidated into a singular collective mask in which the remaining positions are designated as unmasked features by default, thereby creating the consensus mask.

Both data masks and consensus data masks should align appropriately to the respective data profiles of the consumers, to ensure that each data feature associated with each of the consumers is handled as masked or unmasked in accordance with the corresponding data mask. In one embodiment, this can be achieved by generating and using data masks (and consensus data masks) that cover the entire data profile of the consumer, from beginning to end, such that every feature or feature group (an associated set of features treated as a single unit) present within the data profile of the consumer has a corresponding indicator in the mask (e.g., either a 'M' and 'U' character) which indicates whether that data feature is to be treated as a masked feature or an unmasked feature with respect to access and/or transmission. In an alternative embodiment, a data mask does not cover the entire pangenetic or non-pangenetic profile of a consumer, but rather, is mapped to corresponding data features in the profile of the consumer using feature identifiers, indices, addresses, pointers or keys which ensure that the masked and unmasked data feature indicators point to (i.e., map to) the appropriate features (i.e., corresponding feature values) contained in the consumer's data profile. In one embodiment, only masked feature positions are represented in the data mask using feature identifiers, indices, addresses, pointers or keys which point to the corresponding data features of the consumer's data profile, the unmasked features being absent from the data mask. In another embodiment, only the unmasked feature positions are represented in the data mask using feature identifiers, indices, pointers or keys which point to the corresponding data features of the consumer's data profile, the masked features being absent from the data mask.

There are several different methods by which to apply a data mask to a data profile. In one embodiment, a data mask is merged with a data profile of the consumer to generate a temporary data profile (a masked hybrid data profile) of the consumer. This can be accomplished by generating a copy of a data profile of the consumer and replacing those feature values which the data mask indicates need to be masked with, for example, nondescriptive placeholders such as an alphanumeric character or a symbol (e.g., 'X', '#', '*', or '$'), or alternatively, deleting the masked feature values from the temporary data profile. The temporary data profile can then be made available in its entirety for reading or transmission without having to block access or transmission of any of the data features it contains.

In a different embodiment, a data mask can be applied to a data profile by accessing, reading or transmitting data from the data profile in accordance with the pattern of mask and unmask indicators contained in the data mask. As such, the data mask is executed as a set of instructions, wherein each unmask feature indicator is interpreted as a read/transmit (i.e., process feature) instruction with respect to the corresponding data feature value in the consumer's data profile, and wherein each mask feature indicator is interpreted as a non-read/non-transmit (i.e., skip feature) instruction with respect to the corresponding data feature value in the consumer's data profile. In one embodiment, the data mask contains only unmask feature indicators that provide read/transmit instructions with respect to the corresponding data feature values in the consumer's data profile, wherein the unmask feature indicators are mapped to the corresponding features of the consumer's data profile using feature identifiers, indices, addresses, pointers or keys. In another embodiment, the data mask contains only mask feature indicators that provide non-read/non-transmit instructions with respect to the corresponding data feature values in the consumer's data profile, wherein the mask feature indicators are mapped to the corresponding features of the consumer's data profile using feature identifiers, indices, addresses, pointers or keys.

Figure 15:
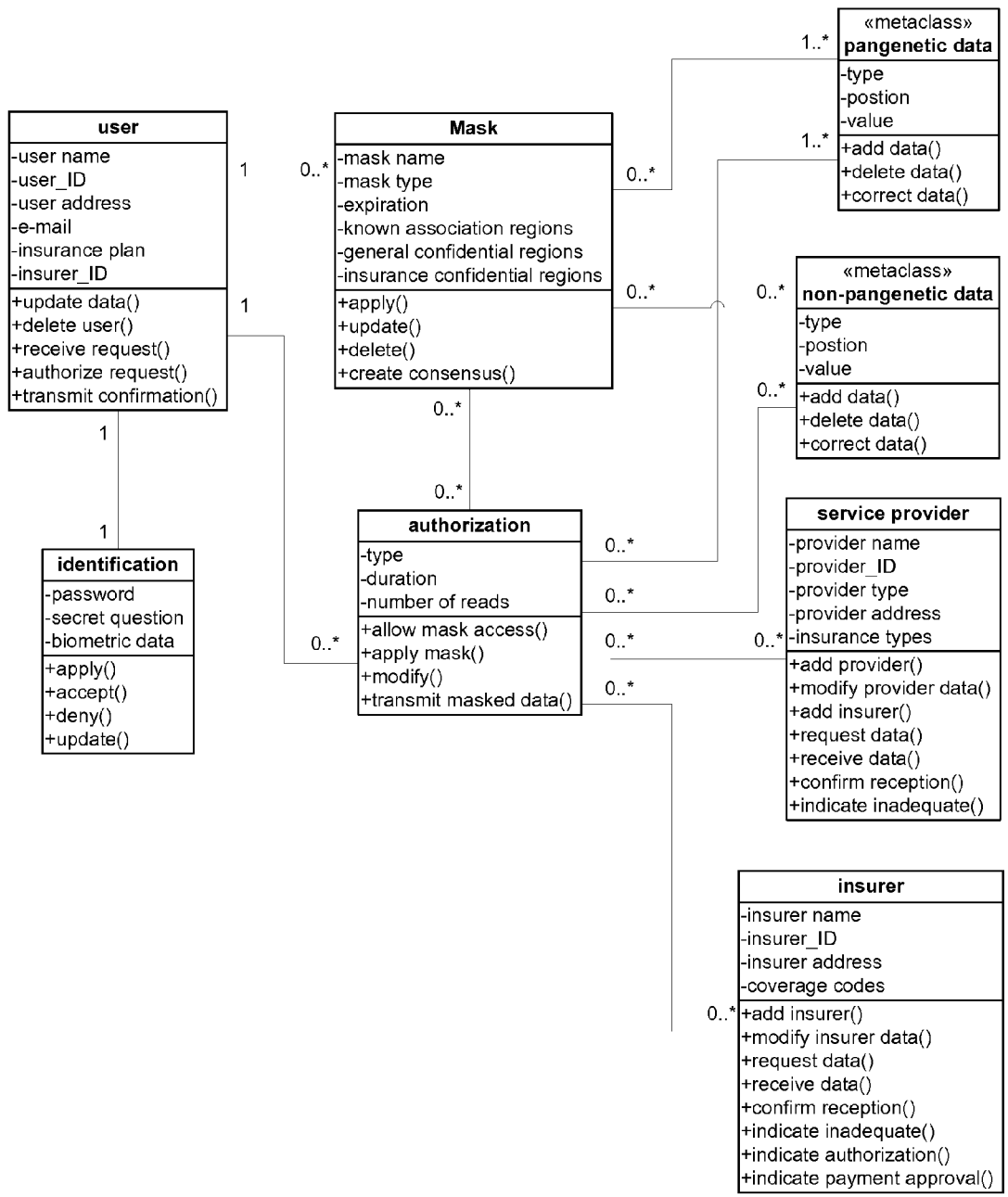
FIG. 15 illustrates a class diagram depicting a healthcare database.

FIG. 15 illustrates a UML class diagram depicting one embodiment of a healthcare database which incorporates masking of pangenetic and non-pangenetic data. The user class, service provider class, and insurer class can interact indirectly with a pangenetic metaclass and a non-pangenetic metaclass (each of which can contain many types of pangenetic data and non-pangenetic data respectively), through an authorization association which can apply masks to the pangenetic data and the non-pangenetic data to obtain appropriately masked data.

As can be seen from FIG. 15, a user that attempts to access the healthcare database system can be identified by the system to ensure that they receive the appropriate degree of access, and the ability to add and modify data as appropriate. As illustrated, an identification class which includes security related attributes such as a password, secret question, and biometric data (e.g., fingerprint scan, retinal scan, or facial recognition data) can be used by the system to identify the user provides when the user logs in to gain access to the system, for example. The various operations associated with the identification class can include an apply operation in which security related attributes are requested of and received from the user; an accept operation in which the identifying information provided by the user at the time of requested access are determined to match stored identification attributes of the user, resulting in granting of access; a deny operation in which identifying information provided by the user at the time of requested access are determined to differ from stored identification attributes of the user, resulting in denial of access; an update operation in which identifying information stored in association with the user (e.g., an identification profile of the user) can be updated to reflect changes in that information, for example user or system initiated password changes.

As further illustrated in FIG. 15, the user class attributes which characterize the user can include a user name, a user_ID, a user address (i.e., mailing, billing, business and/or residential address), an email address, an insurance plan number and type associated with one or more consumers, and an insurer_ID associated with the consumer's insurer and insurance plan. The user can be a consumer, a provider or an insurer, and the user class attributes can be recorded in a user profile contained in a database of the system. Various operations can be associated with the user class and, as illustrated, can include an update data operation that enables the system to update user attributes associated with the user; a delete user operation that enables the system to delete a user record from the system database; a receive request operation that enables the user to input a request for implement of a specific operation (i.e., functionality) of the system such as a request to create a mask or a request to select a service or provider; an authorize request operation that enables the system to authorize the user's request based on the identifying information associated with the user and any permission profiles and/or masks associated with the user, products, services, providers, and particular implementation requested, all of which can be used to determine the level and pattern of data access that is permissible for that user in that instance; and a transmit confirmation operation that enables the system to transmit an indication to the user and other components of the system that access is permitted in accordance with the permission profiles, masks, and the access determination generated for that user for the purpose requested.

As further illustrated in FIG. 15, the user class can interact with the mask class to create and modify various types of data masks. The user can, for example, initiate the creation of masks having attributes which, as illustrated, can include the mask name; the mask type (e.g., general mask types such as genetic, genetic coding, genetic regulatory, epigenetic, non-pangenetic, demographic, or more specific mask types such as those corresponding to and identified by gene name or corresponding trait/condition, for example); the expiration time/date of the mask; the known association regions (i.e., those portions/regions of the masked data that are known to associate with particular physical traits, behaviors, health conditions and/or predispositions); general confidential regions which indicate data that are to be kept private (masked) from others; and insurance confidential regions which indicate data that are to be masked specifically with respect to access and reading of the data by an insurer or in instances of transmission of the data for insurance or payment approval purposes. Various operations can be associated with the mask and, as illustrated, can include an apply operation in which a mask is applied to a set of data; an update operation in which a mask is updated based on user or system supplied information; a delete operation in which a user can implement deletion of a mask or the system can perform automated deletion of a mask that has reached its expiration date; and a create consensus operation in which a consensus data mask can be generated from two or more masks as disclosed previously and then applied to targeted data in accordance with the apply operation.

As further illustrated in FIG. 15, the user class interacts with the authorization class to control access, reading and transmission of consumer associated data (i.e., pangenetic and non-pangenetic data) through application of data masks to the data. The authorization class includes a type attribute which can indicate whether a particular authorization relates to access to pangenetic or non-pangenetic data types, and/or which individual or organization type is attempting to receive access to the data; a duration attribute which can specify the amount of time granted for accessing the data and/or can specify the length of time permissible for a user time-out, after which the system can execute an automated logout of the user from the system; and a number of reads attribute which indicates the number of times the data can be accessed during a each user session, or the number of times a particular portion of the data can be transmitted to a particular destination during each user session. Various operations can be associated with the authorization class and, as illustrated, an allow mask access operation can enable the user to access a mask for analysis, modification or deletion; an apply mask operation which enables a user to modify an existing mask; and a transmit masked data operation which enables the transmission of masked data to a destination such as an interface, workstation or server that is operated or accessed by a service provider or insurer.

FIG. 15 further illustrates a pangenetic data metaclass representing various pangenetic data classes, each of which can be characterized by attributes including a type attribute which indicates the type of pangenetic data; a position attribute which indicates the position of the corresponding genetic or epigenetic feature within the genome and/or within a mask; and a value attribute which indicates the value of the genetic or epigenetic feature, for example the value of a nucleotide feature (e.g., C, A, T or G). The pangenetic data metaclass can have various operations including an add data operation which enables the addition of new pangenetic data to a pangenetic profile of the user, product, service, or provider; a delete data operation which enables the deletion of pangenetic data from the pangenetic profile of a user, product, service or provider; and a correct data operation which enables the modification of pangenetic data contained in the pangenetic profile of a user, product, service or provider.

FIG. 15 further illustrates a non-pangenetic data metaclass representing various non-pangenetic data classes, each of which can be characterized by attributes including a type attribute which indicates the type of non-pangenetic data; a position attribute which indicates the position of the corresponding non-pangenetic feature within a dataset and/or a mask, and a value attribute which indicates the value of the non-pangenetic feature, for example a zip code value which indicates a location.

As illustrated in FIG. 15, attributes of the service provider class can include provider name; a provider_ID linked to the provider name as well as services offered and outcomes achieved; a provider type which can describe the specialty and/or type of services offered by the provider; provider address; and insurance types which can indicate the types of insurance or names of insurance providers that the provider is affiliated with or accepts for payment. The various operations of the service provider class, as illustrated, can include an add provider operation which enables new providers to be added to the system; a modify provider data operation which allows attributes associated with a provider to be updated and changed; an add insurer operation which enables additional insurers to be linked to the provider for purposes of service coverage; a request data operation which enables a service provider to make queries and request various analyses with respect to consumers, insurers, products, services and other service providers; a receive data operation which enables the service provider to receive pangenetic data and analyses results they requested in one of several forms to one of several possible computing devices and interfaces; a confirm reception operation which enables the service provider to confirm receipt of the pangenetic data, wherein the system can record the receipt; and an indicate inadequate operation which enables the service provider to indicate to the system that the pangenetic information provided is inadequate or the recommendation provided with respect to a product, service or provider is unsatisfactory, thereby initiating a reevaluation of the request or additional steps to correct the inadequacy.

As illustrated in FIG. 15, attributes of the insurer class can include insurer name; an insurer_ID linked to at least the insurer name and plans offered by the insurer; an insurer address; and coverage codes linked to products, services and providers covered under the insurer's various plans and customers' policies. The various operations of the insurer class, as illustrated, can include an add insurer operation which enables an insurer to be added to the database system; a modify insurer data operation which enables the attribute data of the insurer to be updated and changed; a request data operation which enables the insurer to make queries and request various analyses with respect to consumers, products, services and service providers; a receive data operation which enables the insurer to receive the data and analyses results they requested in one of several forms to one of several possible computing devices and interfaces; a confirm reception operation which enables the insurer to confirm receipt of the pangenetic data, and the system can record the receipt; an indicate inadequate operation which enables the insurer to indicate to the system that the pangenetic information provided is inadequate or the recommendation provided with respect to a product, service or provider is unsatisfactory; an indicate authorization operation which enables the insurer to indicate approval (i.e., authorize) of a product, service or service provider for a consumer; and an indicate payment approval operation which enables the insurer to authorize payment for a product or service received by a consumer or a service provider that provided services to the consumer.

Figure 16:
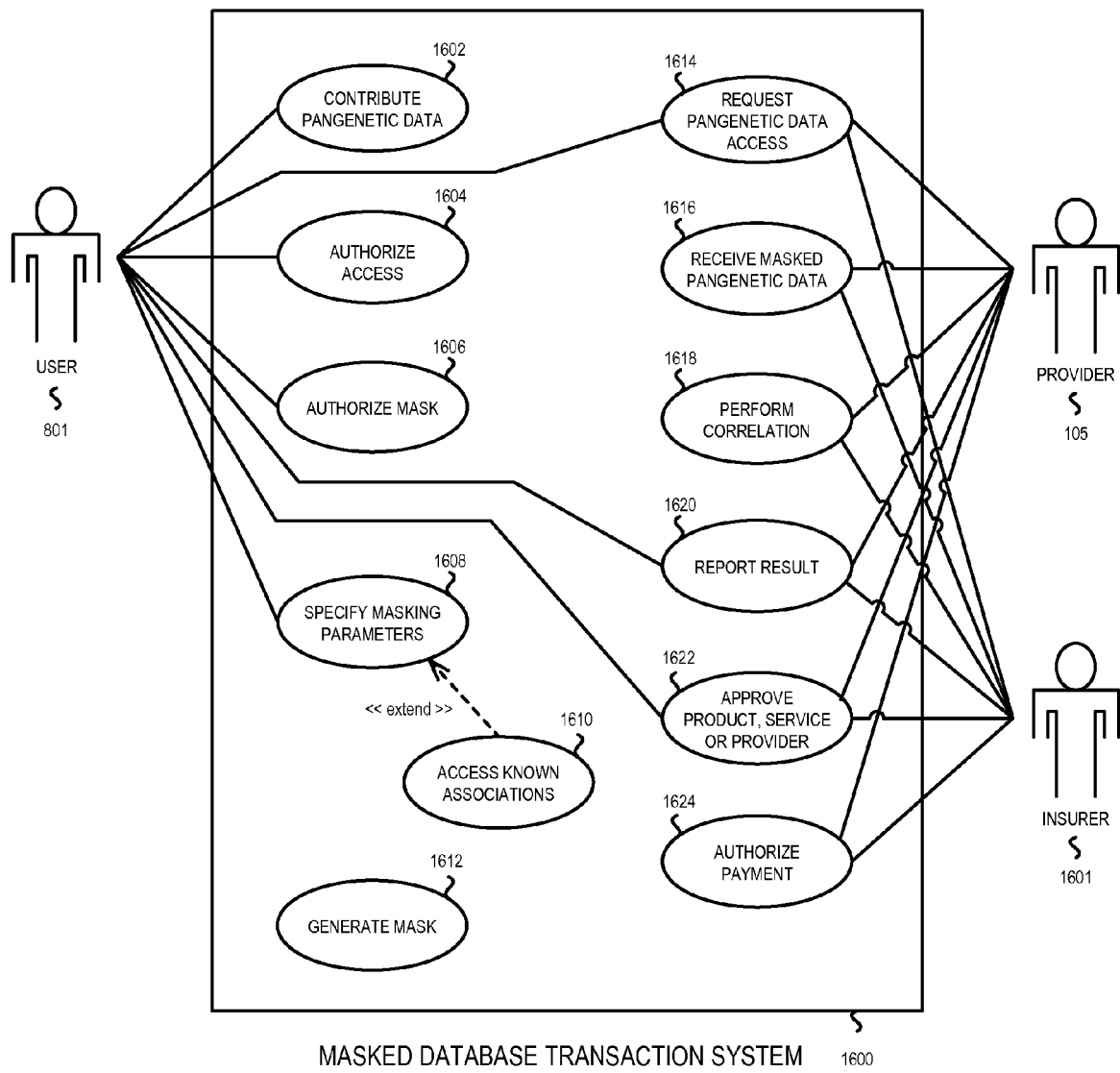
FIG. 16 illustrates a masked database transaction system.

FIG. 16 illustrates a UML use case diagram depicting one embodiment of a masked database transaction system 1600 in which a user, service provider and insurer can interact to select, authorize and approve payment for products, services and providers for a consumer. The user 801 (e.g., a consumer) can add pangenetic data to the masked database transaction system 1600 through contribute pangenetic data use case 1602 in which the user can request import of their pangenetic data from an EMR or another source, the authenticity of the pangenetic data can be verified, and the data reformatted, if necessary, to match a standardized format consistent with requirements for pangenetic masking and pangenetic based profiling and selection of products, services and providers. Through authorize access use case 1604, the user 801 can indicate other users, including providers and insurers, that are permitted at least some degree of access to the user's pangenetic and non-pangenetic data contained in the database of the system. In authorize mask use case 1604, the user 801 can authorize which masks the system should apply when particular providers and insurers attempt to access or receive the user's confidential (i.e., sensitive, private) pangenetic and non-pangenetic data. The user 801 can generate and/or modify masks for application to their pangenetic and non-pangenetic data by indicating which specific features they want concealed in each mask through specify masking parameters use case 1608. With respect to pangenetic features, specify masking parameters use case 1608 can further allow user 801 to specify particular pangenetic based diseases and traits for which they wish to keep the corresponding pangenetic features concealed from insurers, for example. The system can identify the pangenetic features associated with those specified disease and traits through access known associations use case 1610 and then designate those features as parameters to be masked through specify masking parameters use case 1608. In generate mask use case 1612, the system uses the specified masking parameters and mask authorizations to generate one or more masks that can be linked not only to the user, but to particular providers and insurers as authorized by the user and to particular products, services and providers as determined by the system, for performing pangenetic based profiling or selection of products, services and providers.

Further with respect to FIG. 16, user 801, provider 105 and insurer 1601 can submit their identifying information (e.g., user_ID and password) and queries for access to pangenetic data associated with a consumer (e.g., user 801) or queries for pangenetic based selection of products and services through request pangenetic data access use case 1614. Based on the identities of provider 105 and insurer 1601, the system can select and apply the appropriate mask to the pangenetic data associated with the consumer. Provider 105 and insurer 1601 can receive access to or transmission of the masked pangenetic data through receive masked pangenetic data use case 1616. If a query for profiling or selection of products, services or providers was submitted through request pangenetic data access use case 1614, the system can determine the correlation between the pangenetic data associated with the consumer and pangenetic data associated with the products, services or providers through perform correlation use case 1618. If selection of products, services or providers was requested, in perform correlation use case 1618 the system can also select the best product, service or provider, or alternatively, tabulate a rank listing of appropriate products, services or providers based on the determined correlation. The system can then transmit the result to user 801, provider 105 and/or insurer 1601 through a variety of possible interfaces and devices in report result use case 1620. In approve product, service or provider use case 1622, the user 801 and/or the provider 105 can indicate acceptance of a product, service or provider selection that was reported by the system or, if a rank listing was provided by the system, they can select one or more products, services or providers from the rank listing that they prefer over the others. Through authorize payment use case 1624, the insurer 1601 can authorize payment for a product, service or provider selection and the payment authorization can be transmitted to provider 105.

Figure 17:
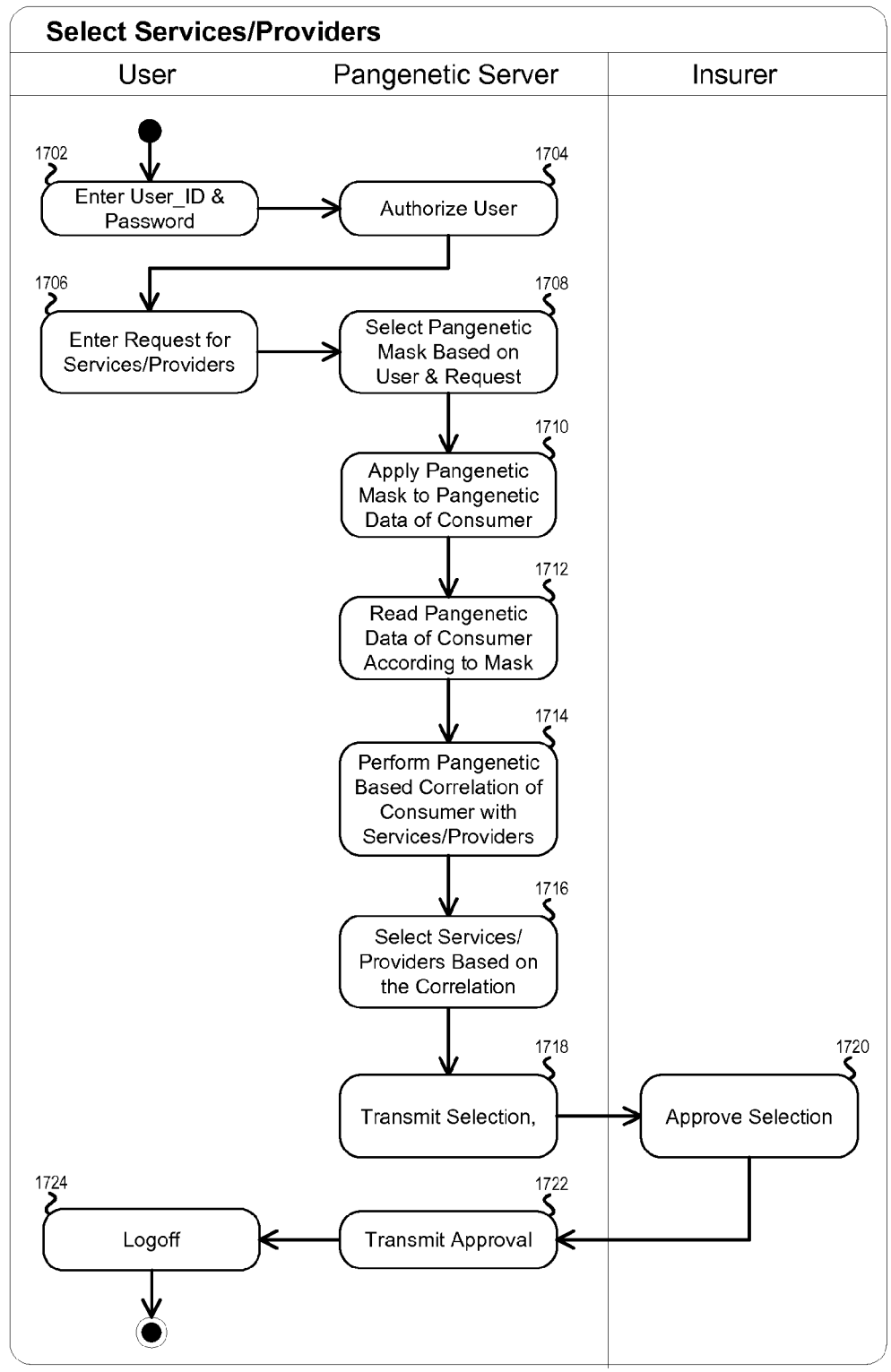
FIG. 17 illustrates a masked data transaction system for selection of services and providers.

FIG. 17 illustrates a UML activity diagram depicting one embodiment of a masked data transaction system for selection of services (including deliverable products) and providers for a consumer. In enter user_ID & password step 1702, a user such as a patient (i.e., consumer), healthcare professional, or insurer representative gains secure access to a pangenetic server (i.e., pangenetic based computer system) by logging on to the system with their secure personal login identifiers. This login information can alternatively be in the form of other secure login procedures such as retinal or fingerprint scan (i.e., biometric data), or a personal identification card that is based on magnetic or RFID technology. In authorize user step 1704, the user logon information is verified and access is granted if the security information passes verification. In one embodiment, the pangenetic server is under the administration of the insurer such that the pangenetic server is an insurer server. In enter request for services/providers step 1706, the user enters a request for selection of one or more services or providers. In select pangenetic mask based on user & request step 1708, the system selects a pangenetic mask based on the identity of the user and the type request entered by the user.

As previously disclosed, a completely different mask may be applied to the consumer's pangenetic data depending on whether user is a physician or an insurer, and whether the request results are to be transmitted as output to a physician as opposed to an insurer. The nature of the request can also determine the application of additional masks, for example, a mask associated with services or providers which reduce the number pangenetic features of the consumer that need to be read to only those which are considered by the system to be relevant to selection of those particular services and providers, or the particular request (e.g., selection versus profiling). In apply pangenetic mask to pangenetic data of consumer step 1710 of FIG. 17, one or more masks can be applied to the pangenetic data of the consumer for the purpose of concealing pangenetic features that are considered by the consumer and/or the system to be confidential with respect to the user and the particular request. In one embodiment this can involve the generation and application of a consensus mask created from two or more masks. In read pangenetic data of consumer according to mask step 1712, the pangenetic features associated with the consumer are read in accordance with the applied mask (i.e., only the unmasked pangenetic data features are read). In perform pangenetic based correlation of consumer with services/providers step 1714, the system compares the unmasked pangenetic features of the consumer with pangenetic data combinations contained in pangenetic based profiles of the services or providers, each pangenetic data combination associated with a particular outcome and a particular service or provider.

In one embodiment, the unmasked pangenetic data features associated with the consumer are correlated with the pangenetic data combinations by determining the percent match between each pangenetic data combination and the pangenetic data of the consumer, and then ranking the pangenetic data combinations based on the percent matching achieved relative to one another. In one embodiment, the rank is also based on levels of success (success levels) associated with the outcomes so that both success level and percent match are used to determine rank in a concurrent evaluation in which a pangenetic combination associated with a higher success level than another pangenetic combination will receive the higher rank when both have the same degree (i.e., percent) of pangenetic match to the consumer. In another embodiment, the percent match and the outcome success level associated with a correlation are both used to determine rank, but are differentially weighted for the purpose of making the determination. In select services/providers based on the correlation step 1716, the most highly ranked (i.e., the best matching) service or provider for the consumer can be selected by the system, or alternatively, several of the most highly ranking services or providers can be selected by the system. In one embodiment, the number of provider or services to be selected can be a predetermined parameter set by the user or system, or can be based on a predetermined threshold which specifies a minimum value for the quality or percentage of the match between the pangenetic data associated with the consumer and a pangenetic data combination associated with a service or provider. In transmit selection step 1718, the one or more selected services or providers are transmitted by the system to the user, and in this example, to an insurer. The destination of the transmission can also be to a database, a dataset, a computer readable memory, a computer readable medium, a computer processor, a computer network, a printout device, a visual display, and a wireless receiver. In one embodiment, the transmission can include ranks of the services or providers and/or the associated outcome success levels (this is applicable to several embodiments disclosed herein).

In approve selection step 1720 of FIG. 17, the insurer can determine whether the selected service or provider, or which of a plurality of selected services or providers, are acceptable for the consumer in the course of formulating a pre-authorization, pre-certification, pre-determination or final authorization of payment. In one embodiment, this determination of approval can be based on a cross-check of the current benefits remaining in the consumer's plan for the year or the consumer's remaining lifetime benefits, for example. In transmit approval step 1722, the determination of approval (or disapproval) of one or more services or providers can be transmitted to the user (e.g., consumer), and/or another individual (e.g., the consumer's doctor) or organization associated with the user. The destination of the transmission can also be to a database, a dataset, a computer readable memory, a computer readable medium, a computer processor, a computer network, a printout device, a visual display, and a wireless receiver. In logoff step 1724, the user logs out to end the session and terminates secure access to the system. This logoff step can be automated based on closing the application or moving out of range of an optical sensor or RFID sensor which detects the presence of the authorized user to ensure that an unauthorized user does not inadvertently gain access the consumer's pangenetic data or pangenetic based results, thereby ensuring that strict doctor-patient privacy can be maintained in a healthcare setting, or ensuring in a public setting that others do not gain access to an individual's pangenetic data through an easily captured mobile device for example.

In one embodiment of a computer based method of profiling products, services and providers, a pangenetic based database system can access a set of outcome data and a plurality of pangenetic data masks associated with a plurality of consumers that received a product or service from a provider. As previously disclosed, the system can generate a consensus pangenetic data mask based on the plurality of pangenetic data masks. The system can then receive access, in accordance with the consensus pangenetic data mask, to a plurality of pangenetic data associated with the plurality of consumers. The system can then generate, based on the accessed pangenetic data and the outcome data, a pangenetic profile containing pangenetic data correlated with outcomes experienced by the consumers with respect to the product, service or provider. The system can then transmit the pangenetic profile in association with an identifier of the product, service or provider in order to provide a pangenetic based profile of the product, service or provider.

In one embodiment of a computer based method for selecting products, services and providers, a pangenetic based database system can receive a request for product, service or provider selection for a consumer. The system can then transmit a request for access to pangenetic data associated with the consumer in accordance with a pangenetic data mask. After receiving access to the pangenetic data in accordance with the pangenetic data mask, the system can then determine the correlation of the pangenetic data with a pangenetic based profile corresponding to a product, service or provider. The system can then transmit an indication that the service is selected for the consumer if the result of the correlation exceeds a predetermined threshold, wherein the predetermined threshold can be set by the system or a user of the system.

Mobile devices (i.e., wireless computing and communications devices) can be utilized advantageously by consumers, providers and insurers for pangenetic based transactions because they can provide the ability to immediately request access to pangenetic information, authenticate themselves on the system, allow approval for access to the pangenetic information, and receive transmitted authorizations, approvals or denials with respect to selection of and payment for various products, services and service providers, for example. However, use of mobile devices place additional requirements on the system due to security concerns and memory limitations.

In terms of security and authentication, the mobile device may use any number of encryption techniques including but not limited to Wired Equivalent Privacy (WEP) encryption, Wi-Fi Protected Access (WPA), Temporal Key Integrity Protocol (TKIP), Lightweight Extensible Authentication Protocol (LEAP), Remote Authentication Dial In User Service (RADIUS), and WLAN Authentication and Privacy Infrastructure. In addition, the mobile devices may use one or more physical types of security including but not limited to smart cards and/or USB tokens. Software tokens may also be used as a form of security.

Additionally with respect to authentication, the mobile device may base authentication on simple password based authentication, biometric identification (e.g. fingerprint recognition or retinal scan) or combinations thereof. Additionally, hardware type solutions may be used in which smart cards, identification chips, or other devices personally associated with the user are utilized in part or wholly for identification and/or authentication. The authorization interface in the mobile device provides the appropriate combination of authentication protocols and procedures to insure that only an authorized individual is authenticated.

In addition to the secure connections, which may be established between the wireless devices and access nodes, pangenetic servers or provider servers, Virtual Private Networks (VPNs) can be used to establish secure end-to-end connections between devices. In one embodiment, wireless security is utilized to establish a secure connection to a server, and a VPN is subsequently established to ensure secure transmission along the entire data path. Similarly, a VPN may be established between the provider mobile device and the provider server, and a VPN may be established between the provider server and the insurer server.

In order to minimize data storage requirements at the mobile devices as well as to limit the amount of pangenetic data that is exposed to the wireless link, in one embodiment little or no pangenetic data is transmitted to the mobile units, but rather is transferred, after appropriate masking, from the pangenetic server to the provider server. In a further embodiment, a second "wireless mask" is utilized to allow the transmission of small amounts of critical pangenetic data to a mobile device. In one embodiment, the consumer or provider can view key segments of the pangenetic information through an appropriate presentation or Graphical User Interface (GUI). For example, a consumer may be seeking treatment for a particular ailment and want to know the overlap of key pangenetic data with other consumers treated with a particular healthcare service. In one embodiment, a comparison of a large amount of masked pangenetic data is performed and used by either the service provider, insurance company, or both, to determine the appropriateness of that healthcare service for the consumer. The consumer and provider may both then receive, on their wireless devices, a transmission of the key overlapping pangenetic features that represent the particular pangenetic features shared in common between the consumer making the inquiry (i.e., query, or request) and other consumers who were successfully treated with that particular healthcare service in the past. In one embodiment, a second wireless mask is used to reduce the amount of data transmitted. In an alternate embodiment, a mathematical or statistical method is used to determine what subset of pangenetic data should be transmitted to the mobile units.

Figure 18:
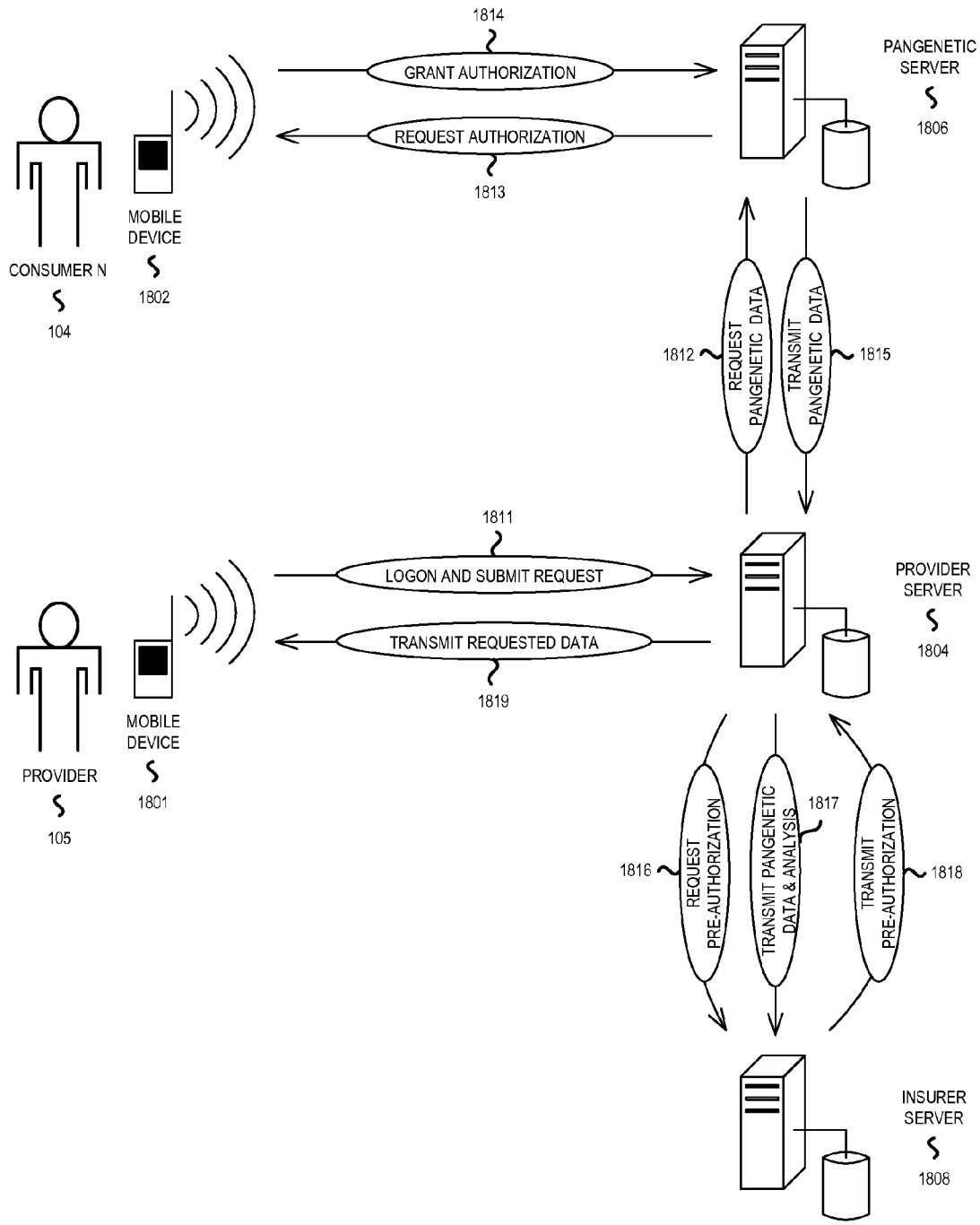
FIG. 18 illustrates a masked database transaction system for a mobile environment.

FIG. 18 illustrates a UML use case diagram depicting a secure masked data transaction system for a mobile environment. In logon and submit request use case 1811, provider 105 can use mobile device 1801 to login to provider server 1804 and either request access to pangenetic data of consumer N 104 stored in pangenetic server 1806, or request selection of products, services and providers for consumer N 104 based on the pangenetic data stored in pangenetic server 1806. In request pangenetic data use case 1812, provider server 1804 can transmit a request to pangenetic server 1806 for access to pangenetic data associated with consumer N 1802. In request authorization use case 1813, pangenetic server 1806 can transmit a request for authorization to mobile device 1802 operated by consumer N 104. Following an identity verification (authentication) procedure process through mobile device 1802 as disclosed previously, consumer N 104 can use mobile device 1802 to grant permission to pangenetic server 1806 for provider 105 to access their pangenetic data through grant authorization use case 1814. This authorization can also involve an automated or consumer initiated request for application of one or more data masks to the pangenetic data for transmission. The choice of masks can be influenced by the nature of the original request and whether the pangenetic data will be further transmitted to an insurer for approval of product or service selections or payment of a claim, for example. In transmit pangenetic data use case 1815, pangenetic server 1806 can transmit the requested pangenetic data to provider server 1804. The pangenetic data can be transmitted in masked form with masked features concealed, or it can be transmitted in accordance with the mask where only unmasked features are actually transmitted, for example. In transmit requested data use case 1819, if provider 105 simply requested pangenetic data associated with consumer 104, pangenetic data can be transmitted to mobile device 1801 for analysis and/or display to provider 105. Alternatively, an analysis of the pangenetic data can be performed on provider server 1804 and the results transmitted for display on mobile device 1801 through transmit requested data use case 1819. In circumstances where insurer approval of a selected product, service or provider is requested, or insurer approval of payment for an insurance claim directed to one or more of those entities is requested, the provider server 1804 can transmit such a request for approval to insurer server 1808 through request pre-authorization use case 1816. The request can constitute a request for a pre-authorization, pre-certification, pre-determination or claim payment, for example. In transmit pangenetic data & analysis use case 1817, provider server 1804 can transmit the pangenetic data and any preliminary analysis results required by the insurer to insurer server 1808. In certain circumstances the provider server 1804 may apply additional masks to the pangenetic data before transmitting the data to insurer server 1808. Following consideration of the pangenetic data and any analysis results derived therefrom, if insurer server 1808 determines that the submitted request should be approved, insurer server 1808 can transmit an approval through transmit pre-authorization use case 1818. Provider server 18084 can generate a record of the pre-authorization in association with consumer N 104 and transmit the pre-authorization to mobile device 1801 of provider 105 through transmit requested data use case 1819. In an alternative embodiment, provider 105 can interact essentially directly with insurer server 1808 using mobile device 1801, without having to go through provider server 1804 as an intermediary.

In one embodiment, a computer based method is provided for utilization of masked healthcare data records which include pangenetic data associated with a consumer. A request for at least one healthcare data record associated with the consumer can be transmitted by a computer server operated by a service provider or a pangenetic server system. Next, at least one healthcare data record, wherein the at least one healthcare data record contains pangenetic data associated with the consumer that has been masked at one or more locations, can be received by the server that made the request.

The server can correlate the at least one healthcare data record with at least one data record corresponding to a pangenetic based treatment to determine the strength of association (correlation) between the consumer's pangenetic makeup and the pangenetic based treatment, and thereby determine the degree of appropriateness of the treatment for the consumer. This correlation process can be repeated for a plurality of pangenetic based treatments, and the plurality of treatments then tabulated based on the results of the correlations (i.e., based on strength of association with the consumer's pangenetic makeup) as a rank listing of treatments which indicates those treatments that are most appropriate for the consumer, for example, in terms of highest likelihood of achieving the desired outcome with least side effects and highest consumer and provider satisfaction levels.

In one embodiment of a computer based method for utilization of masked healthcare data records, the results of the correlation can be used to approve a pangenetic based treatment when the correlation exceeds a predetermined threshold. This approval can also constitute an approval of payment for the pangenetic based treatment, or it can constitute an approval of an insurance claim for the pangenetic based treatment. The results of the correlation and/or the approval can be transmitted to at least one destination selected from the group consisting of a user, a database, a dataset, a computer readable memory, a computer readable medium, a computer processor, a computer network, a printout device, a visual display, and a wireless receiver.

In one embodiment of a computer based method for utilization of masked healthcare data records, determining the correlation between the at least one healthcare data record associated with the consumer and the at least one data record corresponding to a pangenetic based treatment can comprise determining the correlation between pangenetic data contained in the at least one healthcare data record and pangenetic data contained in the at least one data record. The determination of correlation can comprise identifying pangenetic data contained in the at least one healthcare data record that is equivalent to pangenetic data contained in the at least one data record. Identifying the amount and type of pangenetic data contained in the at least one healthcare data record that is equivalent to pangenetic data contained in the at least one data record can be used to determine the degree of correlation. The pangenetic data can be identified as being equivalent if they are identical, or if the pangenetic data are pangenetic features known to be statistically associated with the same outcome with respect to the pangenetic based treatment, or if the pangenetic data differ only with respect to one or more silent pangenetic variations (those that do not impact a phenotype or outcome of interest, for example). At least a portion of the pangenetic data identified as being equivalent can be transmitted along with results of the correlation or the determination of an approval. Assuming the at least one healthcare record also contains non-pangenetic data associated with the consumer, the determination of the correlation can further comprise determining the correlation between non-pangenetic data contained in the at least one healthcare data record and non-pangenetic data contained in the at least one data record corresponding to the pangenetic based treatment.

In one embodiment, a method is presented for providing access to consumer controlled pangenetic information in which a request for a pangenetic record associated with a consumer can be received by a pangenetic based system from a user or another system. The pangenetic based system can then access a data mask, wherein the data mask corresponds to record positions which convey pangenetic features associated with one or more health conditions. The pangenetic based system then applies the data mask to the pangenetic record associated with the consumer to generate a masked pangenetic record, and the masked pangenetic record is transmitted to the user or system that made the request, or to a database, a dataset, a computer readable memory, a computer readable medium, a computer processor, a computer network, a printout device, a visual display, and a wireless receiver.

In one embodiment, a method is presented for providing access to consumer controlled pangenetic information via a pangenetic based system, comprising receiving a request from a user or another system for access to a pangenetic record associated with a consumer; receiving authorization from the consumer for transmission of the pangenetic record (authorization can be provided by a consumer using a mobile device, for example); accessing a data mask that has been previously approved by at least the consumer, wherein the previously approved data mask corresponds to record positions which convey pangenetic features associated with one or more health conditions, disease predispositions or longevity predisposition; applying the previously approved data mask to the pangenetic record associated with the consumer to generate a masked pangenetic record; and transmitting the masked pangenetic record to the user or system that made the request.

In embodiments disclosed herein, the healthcare data record can be, for example, an EMR, EHR or PHR, and the pangenetic based treatment can be a healthcare service, a non-healthcare service, a clinical service, a medical procedure or a surgical procedure. In certain embodiments, the identity of the consumer can be masked or anonymized.

In one embodiment, a computer database system for supporting masked data transactions is provided which comprises 1) a first set of records containing at least one consumer approved data mask, 2) a second set of records containing confidential consumer data, and 3) an authorization module for performing the steps of: a) receiving a request requiring access to at least a portion of the confidential consumer data, b) applying at least one consumer approved data mask from the first set of records to the confidential consumer data from the second set of records, and c) accessing the confidential consumer data in accordance with the applied data mask. The system can also comprise a transaction module for generating pangenetic based profiles of products, services or service providers based on the confidential consumer data, or for selecting products, services or service providers based on the confidential consumer data. The transaction module can also be capable of generating a notification of payment approval, an insurance claim, or a financial transaction for products, services or service providers, for example. The products, services and service providers can be healthcare related or non-healthcare related, and the second set of records can comprise an EMR, EHR or PHR, for example.

In one embodiment of a computer database system for supporting masked data transactions, the application of at least one consumer approved data mask blocks access to and/or reading of at least one portion of the confidential consumer data (e.g., pangenetic data that reveal the consumer's present health conditions, disease predisposition, or predicted longevity). The computer database system can read the confidential consumer data in accordance with the applied data mask, by using the data mask as a set of data reading instructions. Similarly, the computer database system can also transmit the confidential consumer data in accordance with the applied data mask, or the application of the at least one consumer approved data mask can block transmission of at least one portion of the confidential consumer data. In one embodiment, the application of the data mask to the confidential consumer data can comprise generating a consensus mask from two or more data masks from the first set of records and applying the resulting consensus mask to the confidential consumer data.

In one embodiment, a computer database system for supporting masked data transactions is provided which comprises 1) pangenetic data associated with a consumer, 2) authorization records, 3) a data mask indicating one or more portions of the pangenetic data that are not to be transmitted, and 4) a processor for performing the steps of: a) receiving a request for at least a portion of the pangenetic data associated with the consumer, b) verifying the authenticity of the request against the authorization records, and c) transmitting the pangenetic data in accordance with the data mask. The one or more portions of the user pangenetic data that are not to be transmitted can correspond to pangenetic disease markers or longevity markers, for example.

In one embodiment, a computer database system for supporting masked data transactions is provided which comprises 1) a first data structure comprising records which contain consumer pangenetic data, 2) a second data structure comprising data masks which, when authorized for use, determine the transmission of selected subsets of the consumer pangenetic data from the records of the first data structure, and 3) a third data structure comprising authorization records which allow an authorized party to access masked consumer pangenetic data through application of at least one of the data masks of the second data structure to the consumer pangenetic data of the first data structure. In a further embodiment, the computer database system of claim can further comprise a user interface for accessing and modifying the data masks. In another embodiment, the computer database system can further comprise a user interface for accessing and modifying the authorization records. In one embodiment, the application of at least one of the data masks of the second data structure to the consumer pangenetic data of the first data structure can comprise generating a consensus mask from two or more of the data masks of the second data structure and applying the resulting consensus mask to the consumer pangenetic data of the first data structure.

In one embodiment, a computer based method for secure masked data utilization in a mobile environment is provided comprising 1) receiving, from a first mobile device, a request requiring access to pangenetic data (e.g., a request for pangenetic data, or a request requiring processing of pangenetic data) wherein the pangenetic data can be associated with a consumer, 2) receiving, from a second mobile device, an authorization granting access to the pangenetic data, 3) accessing a data mask, wherein the data mask's parameters are associated with the authorization, 4) applying the data mask to the pangenetic data, and 5) transmitting the masked pangenetic data to at least one destination selected from the group consisting of a user, a database, a dataset, a computer readable memory, a computer readable medium, a computer processor, a computer network, a printout device, a visual display, and a wireless receiver. As disclosed previously, the application of the data mask to the pangenetic data can be to conceal one or more pangenetic features associated with one or more health conditions or one or more disease predispositions. The first mobile device can be operated by a healthcare provider or insurer, for example, and the second mobile device can be operated by a consumer.

In a further embodiment of the computer based method for secure masked data utilization in a mobile environment, the masked pangenetic data that is transmitted can be correlated with pangenetic data contained in at least one data record corresponding to a pangenetic based treatment. This correlation step can be repeated for a plurality of pangenetic based treatments, and the plurality of pangenetic based treatments can then be rank listed based on the results of the correlations to indicated which treatments are most appropriate for the consumer. In one embodiment, an approval of the pangenetic based treatment can be transmitted when the correlation exceeds a predetermined threshold. The approval can serve as part of a pre-authorization or a pre-certification, or it can constitute an approval of payment for the pangenetic based treatment such as in a pre-determination or an insurance claim approval by a healthcare insurer. The pangenetic based treatment can be selected from the group consisting of a healthcare service, a non-healthcare service, a clinical service, a medical procedure and a surgical procedure, and the pangenetic data can be contained in a data record such as an EMR, EHR or PHR, for example.

In another embodiment of the computer based method for secure masked data utilization in a mobile environment, the masked pangenetic data that is transmitted can be correlated with pangenetic data contained in at least one data record associated with a health condition diagnosis, and if the strength of the correlation meets a predetermined threshold, for example, the diagnosis can be transmitted as a diagnosis of the consumer's health condition. In another embodiment, the masked pangenetic data that is transmitted can be correlated with pangenetic data contained in at least one data record associated with a health condition prognosis, and if the strength of the correlation meets a predetermined threshold, for example, the prognosis can be transmitted as a prognosis of the consumer's health condition. In another embodiment, the masked pangenetic data that is transmitted can be correlated with pangenetic data contained in at least one data record associated with a healthcare recommendation, and if the strength of the correlation meets a predetermined threshold, for example, the recommendation can be transmitted as a healthcare recommendation for the consumer's health condition. In another embodiment, the masked pangenetic data that is transmitted can be correlated with pangenetic data contained in at least one data record corresponding to a service, and if the strength of the correlation meets a predetermined threshold, for example, an indication that the service is selected for the consumer can be transmitted. In another embodiment, the masked pangenetic data that is transmitted can be correlated with pangenetic data contained in at least one data record corresponding to a service provider, and if the strength of the correlation meets a predetermined threshold, for example, an indication that the service provider is selected for the consumer can be transmitted.

In one embodiment, a computer based method for secure masked data utilization in a mobile environment is provided comprising 1) receiving, from a mobile device, a request requiring access to pangenetic data, 2) receiving an authorization granting access to the pangenetic data, 3) accessing a data mask, wherein the data mask's parameters are associated with the authorization, and 4) transmitting the pangenetic data in accordance with the data mask's parameters. In a further embodiment, transmitting the pangenetic data in accordance with the data mask's parameters can comprise transmitting the portion of the pangenetic data which is indicated by the data mask's parameters as being unmasked while not transmitting the portion of the pangenetic data which is indicated by the data mask's parameters as being masked.

In one embodiment, a computer based method for secure masked data utilization in a mobile environment is provided comprising 1) receiving a request requiring access to pangenetic data, 2) receiving, from a mobile device, an authorization granting access to the pangenetic data, 3) accessing a data mask, wherein the data mask's parameters are associated with the authorization, and 4) transmitting the pangenetic data in accordance with the data mask's parameters. In a further embodiment, transmitting the pangenetic data in accordance with the data mask's parameters can comprise transmitting the portion of the pangenetic data which is indicated by the data mask's parameters as being unmasked while not transmitting the portion of the pangenetic data which is indicated by the data mask's parameters as being masked. In another embodiment, transmitting the pangenetic data in accordance with the data mask's parameters can comprise transmitting a copy of the pangenetic data in which the portion of the pangenetic data indicated by the data mask's parameters as masked is replaced with one or more data placeholders. In another embodiment, transmitting the pangenetic data in accordance with the data mask's parameters can comprise transmitting a copy of the pangenetic data in which the portion of the pangenetic data indicated by the data mask's parameters as masked is omitted.

In one embodiment, a computer based method for accessing masked data in a mobile environment is provided comprising 1) receiving a request requiring access to pangenetic data, 2) generating an authorization associated with at least one pre-approved data mask to grant access to the pangenetic data, and 3) transmitting the authorization associated with the at least one pre-approved data mask. The authorization can be transmitted to at least one destination selected from the group consisting of a user, a database, a dataset, a computer readable memory, a computer readable medium, a computer processor, a computer network, a printout device, a visual display, and a wireless receiver. The data mask can be pre-approved by the consumer associated with the pangenetic data being masked, or the data mask can be pre-approved by a pangenetic based system that had previously identified a minimum set of pangenetic features required for valid pangenetic based selection of products, services or service providers for the consumer. In one embodiment, the authorization granting access to the pangenetic data can be generated if user input is supplied in the form of at least one combination of characters that matches at least one combination of characters (e.g., a user_ID, password, passphrase, passcode, or PIN) previously stored in association with the user, each of the characters being selected from the group consisting of alphanumeric characters and non-alphanumeric characters. For additional security, the combination of characters stored in association with the user can be stored as a cryptographic hash. In another embodiment, the authorization granting access to the pangenetic data can be generated if user input is supplied in the form of at least one combination of characters that matches at least one combination of randomly selected characters (e.g., automatically generated single-use passwords, and CAPTCHA and reCAPTCHA passwords) by software that interacts with the authorization interface, each of the characters being selected from the group consisting of alphanumeric characters and non-alphanumeric characters. In another embodiment, the authorization granting access to the pangenetic data can be generated if user input is supplied in the form of biometric data that matches biometric data previously stored in association with the user.

In one embodiment, a mobile device for providing access to masked data is provided which comprises 1) a receiver for receiving a request requiring access to pangenetic data, 2) an authorization interface for granting access to the pangenetic data by generating an authorization associated with at least one pre-approved data mask, and 3) a transmitter for transmitting the authorization associated with the at least one pre-approved data mask. In one embodiment, the authorization interface can generate the authorization for granting access to the pangenetic data if supplied with user input comprising at least one combination of characters that matches at least one combination of characters (e.g., a user_ID, password, passphrase, passcode, or PIN) previously stored in association with the user, each of the characters being selected from the group consisting of alphanumeric characters and non-alphanumeric characters. For additional security, the combination of characters stored in association with the user can be stored as a cryptographic hash. In another embodiment, the authorization interface generates the authorization if supplied with user input comprising at least one combination of characters that matches at least one combination of randomly selected characters (e.g., automatically generated single-use passwords, and CAPTCHA and reCAPTCHA passwords) by software that interacts with the authorization interface, each of the characters being selected from the group consisting of alphanumeric characters and non-alphanumeric characters. In another embodiment, the authorization interface generates the authorization if supplied with user input comprising biometric data that matches biometric data previously stored in association with the user.

In one embodiment, a computer based method for providing access to masked pangenetic data in a mobile environment is provided comprising 1) receiving a request for pangenetic data, 2) establishing a secure connection with a mobile device, 3) verifying the identity of a user of the mobile device, and 4) authorizing transmission of pangenetic data to which a data mask has been applied based on the request and the verified identity of the user of the mobile device. In one embodiment, verifying the identity of the user of the mobile device can comprise receiving at least one combination of characters input by the user and determining whether the at least one combination of characters input by the user matches at least one combination of characters previously stored in association with the user, each of the characters being selected from the group consisting of alphanumeric characters and non-alphanumeric characters. In another embodiment, verifying the identity of the user of the mobile device can comprise receiving at least one combination of characters input by the user and determining whether the at least one combination of characters input by the user matches at least one combination of characters randomly selected by software that interacts with the authorization interface, each of the characters being selected from the group consisting of alphanumeric characters and non-alphanumeric characters. In another embodiment, verifying the identity of the user of the mobile device can comprise receiving biometric data input by the user and determining whether the biometric data input by the user matches biometric data previously stored in association with the user. In a further embodiment of a computer based method for providing access to masked pangenetic data in a mobile environment, the method can further comprise a step of selecting the data mask for application to the pangenetic data based on the request and the verified identity of the user of the mobile device. In another embodiment, the method can further comprise a step of applying the data mask to the pangenetic data based on the request and the verified identity of the user of the mobile device. In one embodiment, the method can further comprise verifying the application of the data mask to the pangenetic data. For example, a consumer may require application of a particular mask they have pre-approved for use when allowing an insurer to access their pangenetic information. The insurer on the other hand (who is associated with the request) may require the use of particular mask for approval of a service for a particular health condition of the consumer, the mask limiting access to only the relevant pangenetic features that are associated with the service and/or health condition. In one embodiment, this can be achieved by applying the two or more masks in separate operations. In another embodiment, this can be achieved by using the two or more masks to generate a consensus mask which is then applied to the pangenetic data in a single operation.

In one embodiment, a computer system for providing access to masked pangenetic data in a mobile environment is provided comprising 1) a receiving module for receiving a request requiring access to pangenetic data, 2) an authorization module for establishing a secure connection with a mobile device and for verifying the identity of a user of the mobile device, and 3) a communications module for authorizing transmission of pangenetic data to which a data mask has been applied based on the request and the verified identity of the user of the mobile device. In one embodiment, the computer system can further comprise a data mask selection module for selecting the data mask for application to the pangenetic data based on the request and the verified identity of the user of the mobile device. In another embodiment, the system can further comprise a data mask application module for applying the data mask to the pangenetic data based on the request and the verified identity of the user of the mobile device. In one embodiment, the authorization module of the system can also verify the application of the data mask to the pangenetic data.

Figure 19:
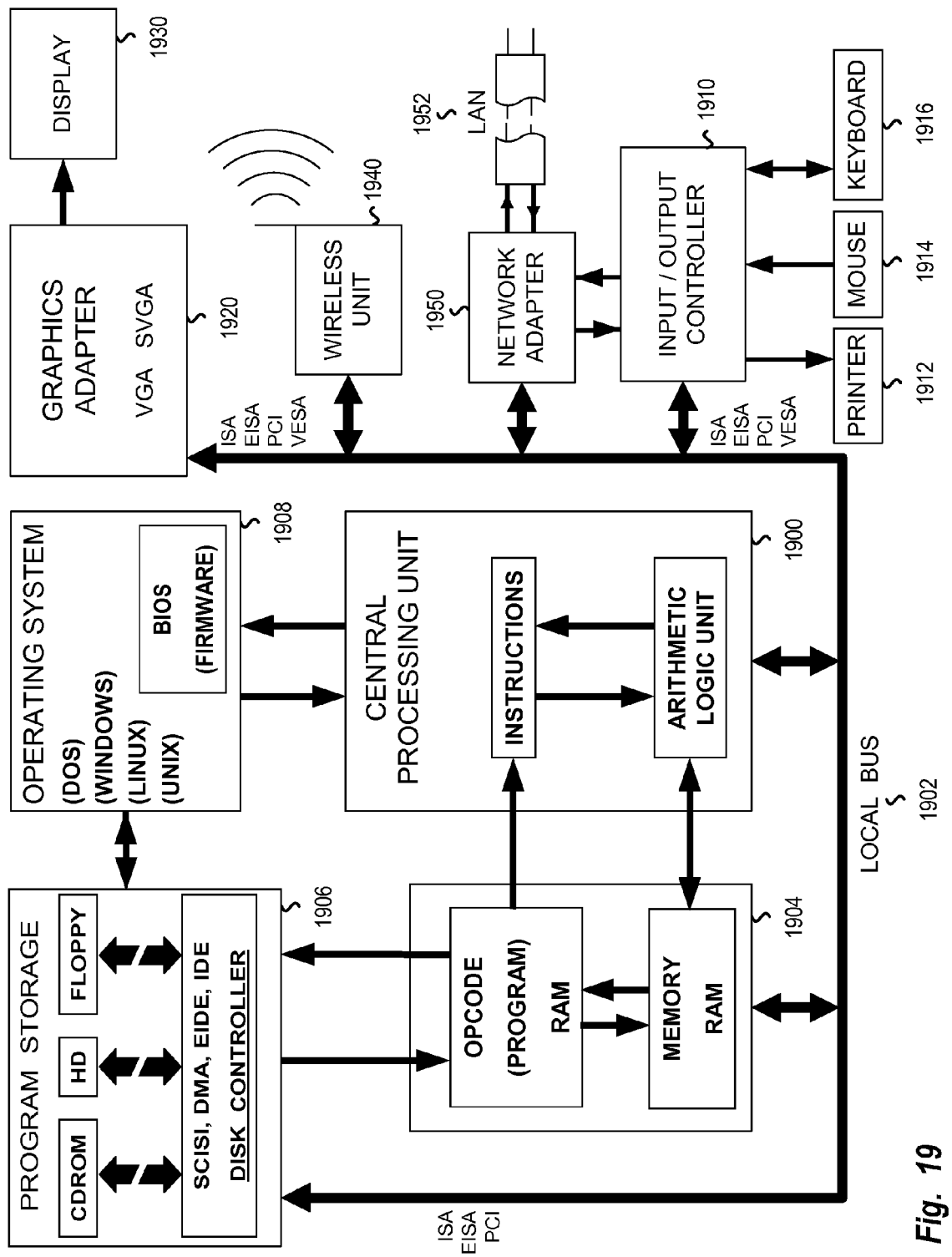
FIG. 19 illustrates a computing system on which the present method and system can be implemented.

FIG. 19 illustrates a representative computing system on which embodiments of the present method and system can be implemented. With respect to FIG. 19, a Central Processing Unit (CPU) 1900 is connected to a local bus 1902 which is also connected to Random Access Memory (RAM) 1904 and disk controller and storage system 1906. CPU 1900 is also connected to an operating system including BIOS 1908 which contains boot code and which can access disk controller and storage system 1906 to provide an operational environment and to run an application (e.g. service profiling or selection). The representative computing system includes a graphics adaptor 1920, display 1930, a wireless unit 1940 (i.e., a data receiver/transmitter device), a network adapter 1950 that can be connected to a LAN 1952 (Local Area Network), and an I/O controller 1910 that can be connected to a printer 1912, mouse 1914, and keyboard 1916.

It will be appreciated by one of skill in the art that the present methods, systems, software and databases can be implemented on a number of computing platforms, and that FIG. 19 is only a representative computing platform, and is not intended to limit the scope of the claimed invention. For example, multiprocessor units with multiple CPUs or cores can be used, as well as distributed computing platforms in which computations are made across a network by a plurality of computing units working in conjunction using a specified algorithm. The computing platforms may be fixed or portable, and data collection can be performed by one unit (e.g. a handheld unit) with the collected information being reported to a fixed workstation or database which is formed by a computer in conjunction with mass storage. Similarly, a number of programming languages can be used to implement the methods and to create the systems disclosed herein, those programming languages including but not limited to C, Java, php, C++, perl, visual basic, SQL and other languages which can be used to cause the representative computing system of FIG. 19 to perform the steps disclosed herein.

Figure 20:
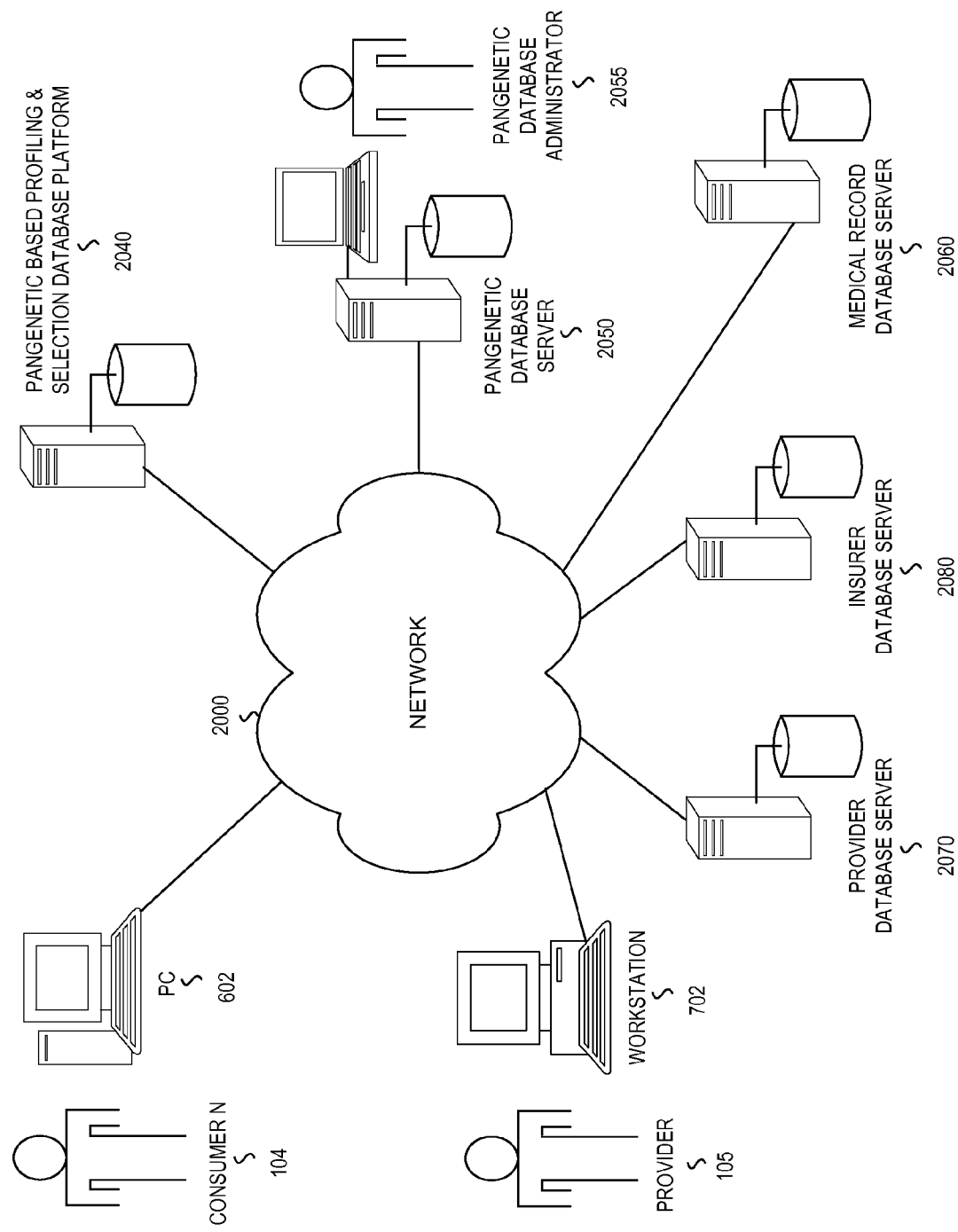
FIG. 20 illustrates a representative deployment diagram for a pangenetic based profiling, selection & approval system.
Figure 15:
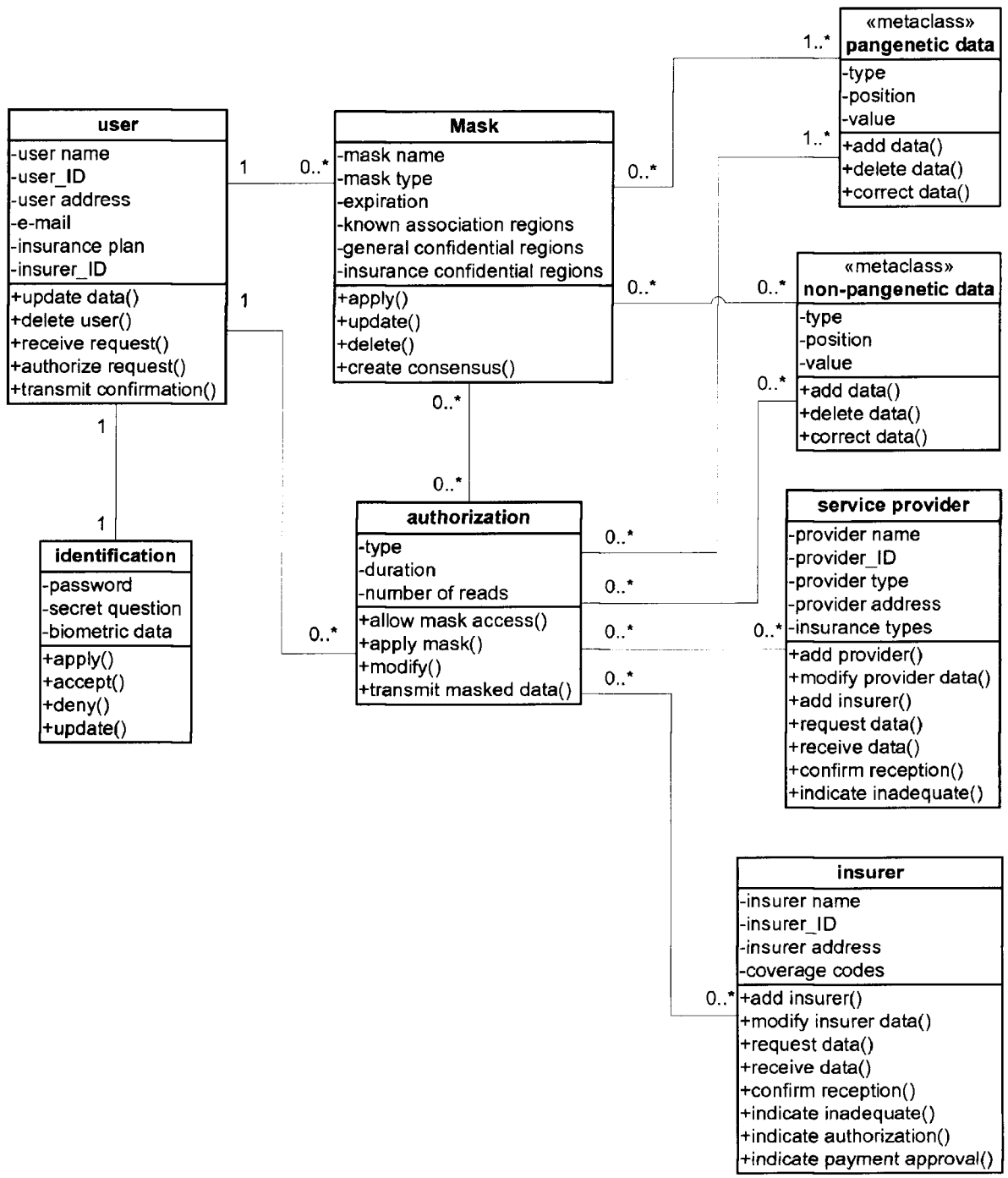

FIG. 20. illustrates a representative deployment diagram for a pangenetic based profiling, selection and approval system. With respect to FIG. 20, the interconnection of various computing systems over a network 2000 to realize the pangenetic based profiling and selection systems of FIGS. 1, 6, 7 and 8, and the masked database transaction systems of FIGS. 16 and 18 is illustrated. In one embodiment, consumer N 104 uses the PC 602 to interface with the system and more specifically to enter and receive data. Similarly, the provider 105 uses the workstation 702 to interface with the system and more specifically to enter and receive data. Pangenetic database administrator 2055 uses an external pangenetic database server 2050 for the storage of pangenetic data in the form of pangenetic EMRs, EHRs, or PHRs for large populations. Pangenetic data can also be stored in medical record database server 2060 in the form of an EMR, EHR or PHR. Consumer N 104 can interact via network 2000 with provider database server 2070 to request and schedule appointments with provider 105 for products, services and provider referrals. Provider 105 can interact via network 2000 with provider database server 2070 to request selection of products, services and providers for consumer N 104, and provider database server 2070 can request access to pangenetic data associated with consumer N 104 as well as other consumers that is stored, for example, on pangenetic database server 2050, with the selection process performed through interaction with pangenetic based profiling & selection database platform 2040. Additionally, provider database server 2080 can interact via network 2000 with insurer database server 2070 to obtain insurer approval and/or payment for selected products, services and providers for consumer N 104. In one embodiment, workstation 702 can provide the same functionality as provider data server 2070 for example. All of the aforementioned computing systems are interconnected via network 2000. Pangenetic database server 2050 can be the same as pangenetic server 1806 of FIG. 18, provider database server 2070 can be the same as provider server 1804 of FIG. 18, and insurer database server 2080 can be the same as insurer server 1808 of FIG. 18. Furthermore, consumer N 104 can use mobile device 1802 of FIG. 18 instead of PC 602 to interface with the system, and provider 105 can use mobile device 1801 of FIG. 18 instead of workstation 702 to interface with the system.

In one embodiment, and as illustrated in FIG. 20, a pangenetic based profiling and selection database platform 2040 is utilized to host the software-based components of pangenetic based profiling and selection systems 100, 600, 700 and 800, and data is collected as illustrated in FIGS. 2, 6, 7 and 8. Once product, service, service provider or establishment selections are determined, they can be displayed to consumer N 104, provider 105, or both. In an alternate embodiment, the software-based components of pangenetic based profiling and selection systems 100, 600, 700 and 800 can reside on workstation 702 operated by provider 105 or on PC 602 operated by consumer N 104. Pangenetic database administrator 2055 may also maintain and operate pangenetic based profiling and selection systems 100, 600, 700 and 800 and host their software-based components on external pangenetic database server 2050 or medical record database server 2060. Another embodiment is also possible in which the software-based components of the pangenetic based profiling and selection systems 100, 600, 700 and 800 are distributed across the various computing platforms. Similarly, other parties and hosting machines not illustrated in FIG. 20 may also be used to create pangenetic based profiling and selection systems 100, 600, 700 and 800.

The methods, systems and databases described herein can also be implemented on one or more specialized computing platforms, those platforms having been customized to provide the services and products described herein. The specialized computing platforms may have specialized operating systems, database tools, graphical user interfaces, communications facilities and other customized hardware and/or software which allow use for the specific application which could not be run on a general purpose computing platform.

Although the systems and methods described herein are frequently described in reference to one or more computers which are typically owned and operated by the actors in the system (e.g., user, service provider, insurance company and pangenetic database administrator), the determination of appropriate products, services and providers can be made through the use of distributed computing systems or cloud computing, wherein the actor requests an action through an interface (typically a web page) and the determination is made using computing resources at one or more server farms, those resources obtaining the appropriate information (e.g. pangenetic information and product, service or provider information and corresponding pangenetic based success rates) from a variety of sources, and combining that information to make the required calculations and determinations. When using a cloud computing system, the subsequent calculations may be performed at alternate locations.

Pangenetic information may be stored in a number of formats, on a variety of media, and in a centralized or distributed manner. In one embodiment, the data is stored in one location with a label associating that data with a particular user, and one or more indices marking or identifying segments of pangenetic data. In an alternate embodiment, the pangenetic data is stored at a plurality of locations with one or more identifiers or labels associating that information with a particular user. In this embodiment, secure communications protocols can be used to allow the system to access all necessary portions of the data and to compile the data in a way that allows the determination of correspondences and applicability to be made. For example, an insurance company may be authorized to compile certain segments of genetic or epigenetic sequences stored in one location with lifestyle information stored in another location to determine which products and services are most appropriate for a consumer. By collecting the relevant information from a plurality of sources, the system is able to construct an appropriate file for the determination of products, services and providers that are most appropriate. In one embodiment, the datasets of the methods of the present invention may be combined into a single dataset. In another embodiment the datasets may be kept separated. Separate datasets may be stored on a single computing device or distributed across a plurality of devices. As such, a memory for storing such datasets, while referred to as a singular memory, may in reality be a distributed memory comprising a plurality of separate physical or virtual memory locations distributed over a plurality of devices such as over a computer network. Data, datasets, databases, methods and software of the present invention can be embodied on a computer-readable media (medium), computer-readable memory (including computer readable memory devices), and program storage devices readable by a machine.

In one embodiment, at least a portion of the data for one or more individuals is obtained from medical records. In one embodiment, at least a portion of the data for one or more individuals is accessed, retrieved or obtained (directly or indirectly) from a centralized medical records database. In one embodiment, at least a portion of the data for one or more individuals is accessed or retrieved from a centralized medical records database over a computer network.

A number of interfaces can be used to support access by users, physicians, insurance companies, and other parties requiring access to the system. In one embodiment an interface is presented over the web, using protocols such as http and https in combination with Hypertext Markup Language (HTML), Java, and other programming and data description/presentation tools which allow information to be presented to and received from the user or users. The interface may contain a number of active elements such as applets or other code which actively constructs display elements and which prompts the user for specific information and which actively creates queries or formulates or formats results for presentation, transmission (e.g. downloading), or storage. In one embodiment the interface allows users to sort data such that products, service and providers can be listed by a particular parameter or sets of parameters. For example, in one embodiment the user can request a presentation of most appropriate (highly matched) service providers which are sub-ranked according to proximity. In an alternate embodiment, a graphical presentation (map) is presented which indicates the most appropriate (highly matched) service providers by color or icon. The interface can allow authorized queries to the different databases in the system, and, within the constraints of the authorizations and permissions, make the determinations of applicability (appropriateness) of products, services and providers based on the pangenetic data of the user. In one embodiment, the user interface at one location (e.g. subscriber location) works in conjunction with a user interface in another location (e.g. insurance company or physician) to allow pangenetic data to be accessed for making a determination of appropriateness of a product, service or provider.

The embodiments of the present invention may be implemented with any combination of hardware and software. If implemented as a computer-implemented apparatus, the present invention is implemented using means for performing all of the steps and functions disclosed above.

The embodiments of the present invention can be included in an article of manufacture (e.g., one or more computer program products) having, for instance, computer useable (i.e., readable) media. The media has embodied therein, for instance, computer readable program code means for providing and facilitating the mechanisms of the present invention. The article of manufacture can be included as part of a computer system or sold separately.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of the present invention is not limited to the particular examples and implementations disclosed herein, but is intended to cover modifications within the spirit and scope thereof as defined by the appended claims and any and all equivalents thereof.

The invention claimed is:

1. A networked computing system for enabling a user to determine the likelihood of success of a treatment comprising:
   a) a first computer or processor which authorizes access to said user's pangenetic data;
   b) a second computer or processor which is programmed to access the user's pangenetic information and, based on authorization received from the first computer or processor, is capable of transmitting at least a portion of the pangenetic data; and
   c) a third computer or processor programmed to receive the at least a portion of the pangenetic data and conduct a comparative assessment of said at least a portion of the pangenetic data with previously stored treatment provider related data to determine likely outcomes or success rates of said user for a treatment and providing said success rates to said user based on prior success rates of treatment of prior users of said treatment with correlated degrees of pangenetic data match of said user.

2. The networked computing system of claim 1 wherein the first computer or processor is a handheld mobile device.

3. The networked computing system of claim 1 wherein the at least a portion of the pangenetic data is generated using a data mask as applied to the pangenetic data.

4. The networked computing system of claim 3 wherein the data mask is predetermined.

5. The networked computing system of claim 1, wherein the pangenetic data are selected from the group consisting of single nucleotide polymorphisms, nucleotides, base pairs, nucleotide sequences, gene sequences, genomic sequences, gene mutations, epigenetic modifications, epigenetic sequence patterns, and pangenetic based disorders, traits and conditions.

6. A computer based method for providing access to pangenetic data of a user to provide said user with data as to the likelihood of a useful therapeutic relationship being possible with respect to said user and a treatment provider comprising:
 a) transmitting a request from a first computer or processor having therapy data stored therein to a second computer or processor, wherein the request includes requiring access to at least a portion of the pangenetic data of said user;
 b) receiving an authorization associated with said user from said second computer or processor, wherein the authorization associated with said user authorizes access to said least a portion of the user's pangenetic data;
 c) receiving said at least a portion of the user's pangenetic data at the first computer or processor; and,
 d) conducting a comparative assessment of said at least a portion of the user's pangenetic data with previously stored treatment provider related data to determine likely outcomes or success rates of said user with said treatment provider and providing said success rates to said user based on prior success rates of treatment of prior users having correlated degrees of pangenetic data match with said user.

7. The computer based method of claim 6 wherein the second computer or processor is a handheld mobile device.

8. The computer based method of claim 6 wherein the at least a portion of the pangenetic data of the user is generated based on the use of a data mask.

9. The computer based method of claim 8 wherein the data mask is predetermined.

10. The method of claim 6 wherein the user's pangenetic data is stored at the second computer or processor.

11. The method of claim 6 wherein the user's pangenetic data is stored at a third computer or processor.

12. A program storage device readable by a machine and containing a set of instructions which, when read by the machine, causes execution of a computer based method for providing access to pangenetic data of a user to provide said user with data as to the likelihood of a useful therapeutic relationship being possible with respect to said user and a therapy provider, comprising:
 a) transmitting a request from a first computer or processor having therapy data stored therein to a second computer or processor, wherein the request includes requiring access to at least a portion of the pangenetic data of said user;
 b) processing an authorization associated with said user from said second computer or processor, wherein the authorization associated with said user authorizes access to said least a portion of the user's pangenetic data;
 c) receiving and storing said at least a portion of the user's pangenetic data at the first computer or processor; and
 d) conducting a comparative assessment of said at least a portion of the user's pangenetic data with previously stored treatment provider related data to determine likely outcomes or success rates of said user with said treatment provider and providing said success rates to said user based on prior success rates of treatment of prior users having correlated degrees of pangenetic data match with said user.

13. The program storage device of claim 12 wherein the processing of said authorization includes the application of a data mask.

14. The program storage device of claim 13 wherein the processing of said authorization includes the application of a predetermined data mask.

* * * * *

UNITED STATES PATENT AND TRADEMARK OFFICE
CERTIFICATE OF CORRECTION

PATENT NO.       : 8,458,097 B2
APPLICATION NO.  : 13/037917
DATED            : June 4, 2013
INVENTOR(S)      : Kenedy et al.

It is certified that error appears in the above-identified patent and that said Letters Patent is hereby corrected as shown below:

Title Page 3, in Item (56), under "OTHER PUBLICATIONS", in Column 1, Line 4, delete "Leveraing" and insert -- Leveraging --, therefor.

Title Page 3, in Item (56), under "OTHER PUBLICATIONS", in Column 1, Line 5, delete "experiental" and insert -- experiential --, therefor.

Title Page 3, in Item (56), under "OTHER PUBLICATIONS", in Column 1, Line 5, delete "Anautomated" and insert -- An automated --, therefor.

Title Page 3, in Item (56), under "OTHER PUBLICATIONS", in Column 1, Line 7, delete "InformationJournal" and insert -- Information Journal --, therefor.

Title Page 3, in Item (56), under "OTHER PUBLICATIONS", in Column 2, Line 9, delete "ECML/PKDD04" and insert -- ECML/PKDD '04 --, therefor.

Title Page 3, in Item (56), under "OTHER PUBLICATIONS", in Column 2, Line 33, delete "Persoanlized" and insert -- Personalized --, therefor.

Title Page 3, in Item (56), under "OTHER PUBLICATIONS", in Column 2, Line 34, delete "Maerican" and insert -- American --, therefor.

Title Page 3, in Item (56), under "OTHER PUBLICATIONS", in Column 2, Line 41, delete "Genome Research. 2000 10: 950-958." and insert -- Genome Research 2000 Jul; 10(7): 950-958, --, therefor.

Title Page 3, in Item (56), under "OTHER PUBLICATIONS", in Column 2, Line 45, delete "167-1 70" and insert -- 167-170 --, therefor.

Signed and Sealed this
Fifth Day of November, 2013

Teresa Stanek Rea
*Deputy Director of the United States Patent and Trademark Office*

CERTIFICATE OF CORRECTION (continued)
U.S. Pat. No. 8,458,097 B2

In the Drawings

In Fig. 15, Sheet 15 of 20, delete Figure 15 and insert the attached Replacement Sheet herewith.

In Fig. 17, Sheet 17 of 20, for Tag "1718", in Line 1, delete "Selection," and insert -- Selection --, therefor.

In the Specifications

In Column 1, Line 5, delete "in a" and insert -- is a --, therefor.

In Column 11, Line 41, delete "FIG. 2. as" and insert -- FIG. 2 as --, therefor.

In Column 16, Line 60, delete "User 802 via PC 804" and insert -- User 801 via PC 802 --, therefor.

In Column 28, Line 65, delete "provider" and insert -- service --, therefor.

In Column 39, Line 46, delete "mask use case 1604," and insert -- mask use case 1606, --, therefor.

In Column 44, Lines 4-5, delete "consumer N 1802." and insert -- consumer N 104. --, therefor.

In Column 44, Line 26, delete "consumer 104," and insert -- consumer N 104, --, therefor.

In Column 44, Line 50, delete "Provider server 18084" and insert -- Provider server 1804 --, therefor.

In Column 51, Line 39, delete "adaptor" and insert -- adapter --, therefor.

In Column 51, Line 64, delete "FIG. 20." and insert -- FIG. 20 --, therefor.

In Column 52, Line 24, delete "provider database server 2080" and insert -- provider database server 2070 --, therefor.

In Column 52, Line 25, delete "insurer database server 2070" and insert -- insurer database server 2080 --, therefor.

In Column 52, Line 28, delete "provider data" and insert -- provider database --, therefor.

In the Claims

In Column 55, Line 30, in Claim 6, delete "said least" and insert -- said at least --, therefor.

In Column 56, Line 6, in Claim 10, delete "method" and insert -- computer based method --, therefor.

In Column 56, Line 8, in Claim 11, delete "method" and insert -- computer based method --, therefor.

In Column 56, Line 25, in Claim 12, delete "said least" and insert -- said at least --, therefor.